United States Patent
Ballamy

(10) Patent No.: US 11,865,192 B2
(45) Date of Patent: Jan. 9, 2024

(54) MODIFIED WOUND DRESSINGS

(71) Applicant: CONVATEC TECHNOLOGIES INC., Las Vegas, NV (US)

(72) Inventor: Lucy Ballamy, Llangollen (GB)

(73) Assignee: ConvaTec Technologies, Inc., Las Vegas, NV (US)

( * ) Notice: Subject to any disclaimer, the term of this patent is extended or adjusted under 35 U.S.C. 154(b) by 105 days.

(21) Appl. No.: 17/201,898

(22) Filed: Mar. 15, 2021

(65) Prior Publication Data

US 2021/0275693 A1 Sep. 9, 2021

Related U.S. Application Data

(63) Continuation of application No. 16/090,103, filed as application No. PCT/US2017/024915 on Mar. 30, 2017, now abandoned.

(Continued)

(51) Int. Cl.
*A61K 49/00* (2006.01)
*A61L 15/44* (2006.01)
(Continued)

(52) U.S. Cl.
CPC ...... *A61K 49/0043* (2013.01); *A61K 49/0021* (2013.01); *A61K 49/0054* (2013.01);
(Continued)

(58) Field of Classification Search
CPC .. A61K 9/06; A61K 49/0056; A61K 49/0073; A61K 49/0054; A61K 49/0043;
(Continued)

(56) References Cited

U.S. PATENT DOCUMENTS 5,362,628 A 11/1994 Haugland et al.
5,558,861 A 9/1996 Yamanaka et al.
(Continued)

FOREIGN PATENT DOCUMENTS

EP 0243151 A2 10/1987
EP 1577316 A1 9/2005
(Continued)

OTHER PUBLICATIONS

Plyduang et al., "Carboxymethylcellulose-tetrahydrocurcumin conjugates for colon-specific delivery of a novel anti-cancer agent, 4-aminotetrahydrocurcumin", European Journal of Pharmaceutics and Biopharmaceutics 88 (2014) 351-360. (Year: 2014).*
(Continued)

*Primary Examiner* — Jianfeng Song
(74) *Attorney, Agent, or Firm* — Taft Stettinius & Hollister LLP; Ryan O. White; Derek B. Lavender

(57) ABSTRACT

Embodiments described herein relate to compounds for the detection of wounds, e.g., chronic wounds or infected wounds, including compositions, substrates, kits, dressing materials, and articles, and systems containing such compounds. Further embodiments relate to methods of using these compositions, kits and systems in diagnostic assays, and in the diagnosis and/or detection of chronic or infected wounds based on enzymatic conversion of specific substrates which are contained in the compositions. Additional embodiments relate to methods of characterizing wounds based on expression of a plurality of markers and using such information to treat, manage, and follow-up patients suffering from chronic or infected wounds.

1 Claim, 15 Drawing Sheets

Related U.S. Application Data

(60) Provisional application No. 62/315,567, filed on Mar. 30, 2016.

(51) Int. Cl.
*A61L 15/56* (2006.01)
*A61L 15/60* (2006.01)
*A61L 15/42* (2006.01)
*A61K 9/06* (2006.01)
*A61L 15/46* (2006.01)

(52) U.S. Cl.
CPC ...... *A61K 49/0056* (2013.01); *A61K 49/0073* (2013.01); *A61L 15/42* (2013.01); *A61L 15/44* (2013.01); *A61L 15/56* (2013.01); *A61L 15/60* (2013.01); *A61K 9/06* (2013.01); *A61L 15/46* (2013.01); *A61L 2300/406* (2013.01); *A61L 2300/414* (2013.01); *A61L 2300/442* (2013.01)

(58) Field of Classification Search
CPC ..... A61K 49/0021; A61L 15/46; A61L 15/44; A61L 2300/442; A61L 15/56; A61L 2300/414; A61L 15/42; A61L 15/60; A61L 2300/406
See application file for complete search history.

(56) References Cited

U.S. PATENT DOCUMENTS

| 7,550,154 | B2 * | 6/2009 | Saltzman | A61P 27/02 |
|---|---|---|---|---|
| | | | | 977/773 |
| 2004/0101547 | A1 | 5/2004 | Pendharkar et al. | |
| 2006/0166929 | A1 | 7/2006 | Kajihara et al. | |
| 2012/0183585 | A1 | 7/2012 | Dinavand et al. | |
| 2013/0309286 | A1 | 11/2013 | Engstad et al. | |
| 2014/0045761 | A1 | 2/2014 | Gibson | |
| 2014/0179913 | A1 | 6/2014 | Paullin et al. | |
| 2016/0022730 | A1 | 1/2016 | Baker et al. | |
| 2016/0129150 | A1 | 5/2016 | Saijo et al. | |
| 2021/0275693 | A1 | 9/2021 | Ballamy | |
| 2022/0096704 | A1 | 3/2022 | Ballamy et al. | |

FOREIGN PATENT DOCUMENTS

| EP | 3936095 | A1 | 1/2022 |
|---|---|---|---|
| EP | 2902068 | B2 | 9/2022 |
| EP | 4104869 | A1 | 12/2022 |
| EP | 3662876 | B1 | 3/2023 |
| GB | 2381452 | A | 5/2003 |
| JP | 2012527225 | A | 11/2012 |
| JP | 2013-544817 | A | 12/2013 |
| JP | 2014503252 | A | 2/2014 |
| WO | 9304192 | A1 | 3/1993 |
| WO | 1577316 | A1 | 9/2005 |
| WO | 2010133589 | A1 | 11/2010 |
| WO | 2012073020 | A1 | 6/2012 |
| WO | 2012074509 | A1 | 6/2012 |
| WO | 2014162906 | A1 | 10/2014 |

OTHER PUBLICATIONS

Ravindran Girija Aswathy et al.; Multifunctional Biocompatible Fluorescent Carboxymethyl Cellulose Nanoparticles; Journal of Biomaterials and Nanobiotechnology; 2012; 8 pages; vol. 3.

Qian Garrett et al.; Carboxymethylcellulose Binds to Human Corneal Epithelial Cells and is a Modulator of Corneal Epithelial Wound Healing; Investigative Ophthamology & Visual Science; Apr. 2007; 9 pages; vol. 48, No. 4.

Su Yeon Lee et al.; Synthesis and In Vitro Characterizations of Porous Carboxymethyl Cellulose-poly(ethylene oxide) Hydrogel Film; Biomaterials Research; 2015; 11 pages; vol. 19, No. 12.

Mike Orcutt; "Smart Bandage Signals Infection by Turning Fluorescent—MIT Technology Review"; MIT Technology Review, Dec. 4, 2015; 8 pages.

Anonymous; "Glowing bandages 'could show infections'—NHS". NHS, Sep. 16, 2011; 5 pages.

Saswati Ghosh Roy et al; "Tryptophan containing covalently cross-linked polymeric gels with fluorescence and pH-induced reversible sol-gel transition properties", Polymer Chemistry, vol. 5, No. 11, Jan. 1, 2014, p. 3624.

Anonymous; "Gel shines bright to spot bacteria—Futurity"; Futurity, Sep. 19, 2011, 6 pages; retrieved from the Internet on Sep. 2, 2019: https://www.futurity.org/ge;-shines-bright-to-spot-bacteria/.

Gayathri Srinivasan: "PEG-base Fluorescent Hydrogel for Glucose Biosensing"; Masters Thesis; Jan. 1, 2014, 62 pages.

European Search Report; dated Sep. 10, 2019; 9 pages.

Communication pursuant to Article 94(3) EPC; European Patent Office; European Patent Application No. 17776619.3; dated Apr. 30, 2020; 5 pages.

Communication pursuant to Article 94(3) EPC; European Patent Office; European Patent Application No. 17776619.3; Jun. 25, 2020; 5 pages.

International Search Report; International Searching Authority; International Application No. PCT/US2017/024915; dated Aug. 29, 2017; 3 pages.

Japanese Office Action, Japan Patent Office, Japanese Patent Application No. 2018-551313, Feb. 16, 2021, 4 pages.

Singaporean Written Opinion, Intellectual Property Office of Singapore, Singaporean Patent Application No. 11201808528V, dated Jan. 12, 2021, 7 pages.

Fatemeh Derikvand et al.; Cellulose-Based Biosensors for Esterase Detection; Analytical Chemistry; 2016; 4 pages; vol. 88.

Korean Office Action; Korean Intellectual Property Office; Korean Patent Application No. 10-2018-7031425; Sep. 8, 2021; 6 pages.

Japanese Office Action; Japan Patent Office; Japanese Patent Application No. 2018-551313; dated Oct. 19, 2021; 5 pages.

Japanese Office Action, Japan Patent Office, Japanese Patent Application No. 2022-023906, dated May 9, 2023, 4 pages.

Canadian Office Action, Canadian Intellectual Property Office, Canadian Patent Application No. 3,019,548, dated May 11, 2023, 6 pages.

Japanese Office Action, Japan Patent Office, Japanese Patent Application No. 2018-551313, dated Jun. 20, 2023, 10 pages.

Kagami, Dissertation Thesis "Development of Asymmetric Si Rhodamine Fluorescent Dyes and Their Application to Ratio-Type pH-Sensitive Fluorescent Probes", 2016 <URL; https://repository.dl.itc.u-tokyo.ac.jp/record/48730/files/A32851.pdf.

Edwards et al., A Bio-Sensor for Human Neutrophil Elastase Employs Peptide-p-Nitroanilide Cellulose Conjugates, Sensor Letters, 2008, vol. 6, No. 4, pp. 518-523.

\* cited by examiner 01 hour 30 hours 50 hours 68 hours 01 hour 30 hours 50 hours 68 hours

| Sample | DAY 3 | DAY 7 | Note |
|---|---|---|---|
| Control |  |  | Collagen diameter decreased |
| 12 |  |  | Collagen diameter decreased |
| 83 |  |  | No effect on collagen diameter |
| 81 |  |  | Collagen diameter decreased |
| 74 |  |  | Collagen diameter decreased |
| 78 |  |  | Collagen diameter slightly decreased |
| 80 |  |  | Collagen diameter decreased |
| CMC powder |  |  | Collagen diameter decreased |
| CMC fibre |  |  | Collagen diameter decreased |

| Sample | DAY 3 | DAY 7 | Note |
|---|---|---|---|
| Control |  |  | Collagen diameter decreased |
| 12 |  |  | Collagen diameter decreased |
| 83 |  |  | No effect on collagen diameter |
| 81 |  |  | Collagen diameter decreased |
| 74 |  |  | Collagen diameter decreased |
| 78 |  |  | Collagen diameter decreased |
| 80 |  |  | Collagen diameter decreased |
| CMC powder |  |  | Collagen diameter decreased |
| CMC fibre |  |  | Collagen diameter decreased |

| Sample | DAY 3 | DAY 7 | Note |
|---|---|---|---|
| Control |  |  | Collagen diameter decreased |
| 12 |  |  | Collagen diameter decreased |
| 83 |  |  | No effect on collagen diameter |
| 81 |  |  | Collagen diameter decreased |
| 74 |  |  | Collagen diameter decreased |
| 78 |  |  | Collagen diameter decreased |
| 80 |  |  | Collagen diameter decreased |
| CMC powder |  |  | Collagen diameter decreased |
| CMC fibre |  |  | Collagen diameter decreased |

MODIFIED WOUND DRESSINGS

CROSS-REFERENCE TO RELATED APPLICATIONS

This application is a continuation application of, and claims the benefit of, U.S. application Ser. No. 16/090,103, which was filed on Sep. 28, 2018, and which is a U.S. National Phase entry of International Application No. PCT/US2017/024915, which was filed on Mar. 30, 2017, and which claims the benefit of U.S. Provisional Application No. 62/315,567, which was filed on Mar. 30, 2016. The contents of those applications are incorporated by reference herein in their entireties.

TECHNICAL FIELD

Embodiments described herein generally relate to wound healing, and in particular to compositions and methods for the detection and treatment of wounds.

BACKGROUND OF THE INVENTION

In mammals, dermal injury triggers an organized complex cascade of cellular and biochemical events that result in a healed wound. Wound healing is a complex dynamic process that results in the restoration of anatomic continuity and function: an ideally healed wound is one that has returned to normal anatomic structure, function, and appearance. A typical wound heals via a model consisting of four stages— 'exudative' phase, proliferative phase, reparative phase and epithelial maturation (Hatz et al., *Wound Healing and Wound Management*, Springer-Verlag, Munich, 1994) or hemostatic, inflammatory, proliferative and remodeling phase (Nwomeh et al., *Clin. Plast. Surg.* 1998, 25, 341).

Unfortunately, chronic and 'infected" wounds are typically hard to heal. Chronic wounds include, e.g., venous leg ulcers, diabetic foot ulcers and pressure sores (Krasner et al., *Chronic Wound Care: A Clinical Source Book for Healthcare Professionals*, HMP Communications, 2001). Patients with chronic wounds require a great deal of care and the wound often leads to a reduction in quality of life; a chronic wound can become a problem that some patients must deal with throughout the rest of their life. Patient co-morbidities can also have a significant effect on the wound healing process, limiting and even halting the process as well as being contributing factors to the loss of quality of life. Factors which can lead to a wound being difficult to heal include pathophysiological issues, infection by microorganisms, presence of non-viable tissue, poor tissue perfusion, chronic inflammatory conditions and other underlying conditions such as diabetes (Bowler et al., *Annals of Medicine* 2002, 34, 419-427).

In many instances, chronic wounds are colonized by bacterial flora and/or pathogens such as fungi and viruses, in which case they may become infected. Infection of wounds by bacteria delays the healing process, since bacteria produce enzymes and toxins and also compete for nutrients and oxygen with macrophages and fibroblasts whose activities are essential for the healing of the wound. Infection is therefore a manifestation of a disturbed host/bacteria equilibrium in favor of the invading bacteria. This elicits a systemic septic response, and also inhibits the multiple processes involved in wound healing. The granulation phase of healing will only begin after the infection has subsided.

The inflammatory phase is particularly important to the wound healing process, wherein biochemical reactions at the wound situs facilitate healing but also cause tissue breakdown due to production of excess proteases. Although proteases play an important role in breaking down dead tissue, in excess, they also have a detrimental effect on viable tissue, cause additional inflammation. The release of these proteolytic enzymes, such as matrix metalloproteases (MMP), elastase, and cathepsin G, is often associated with excessive stimulation of neutrophils.

Elevated protease activity appears to be responsible for delaying wound repair and may be predictive of wound infection. For instance, the extracellular matrix (ECM), a collection of extracellular molecules secreted by cells that provides structural and biochemical support to the surrounding cells, is frequently depleted at the wound site due to excess protease (e.g., MMP) activity and concomitantly due to attenuated fibrinogen levels. Increased protease activity also leads to degradation of growth factors, thus inhibiting the healing process. Accordingly, infection and other problems are exacerbated in chronic wounds and the wound remains difficult to treat (Yager et al., *Wound Repair Regen* 1997, 5, 23-32; Widgerow et al., *Wound Repair Regen* 2011, 19, 287-291).

Current methods of assessing a wound rely on the training and experience of the practitioner. A wound is likely to be assessed visually, length and depth measurements may be taken, and digital photography may be used where available to track the visual condition and size of a wound (Krasner et al., supra). In clinical practice, diagnosis of infection is based on indirect parameters, such as, presence of local pain, heat, swelling, discharge, and redness. Many of these clinical indicators, such as inflammation and discharge have a low predictive value of infection in wounds. Swabbing of a wound followed by microbiology testing in the hospital laboratory is an option for confirmation of bacterial colonization and identification of the strain in order to prescribe the correct antibiotic course; however, this process is time consuming and labor intensive. Delay in diagnosis of infection can delay the administration of antibiotics and may increase the risk of developing sepsis.

Additionally, there are few objective techniques for measurement of wound healing. Although there are reports that MMP protease levels and activity are present in the fluid of chronic wounds when compared to the fluid in healing wounds (Liu et al., Diabetes Care 2009, 32, 117-119; Bullen et al., *J. Investig. Dermatol.* 1995, 104, 236-240), these reports do not suggest the limit at which the wound becomes chronic.

Thus, there is an imminent but unmet need for sensitive and specific reagents, kits and assay techniques for identifying chronic and infected wounds in humans and veterinary subjects, including, using such reagents and/or kits for scientific studies and also in clinical applications, for example, in the efficient and accurate diagnosis and treatment of diseases that are characterized by such wounds, e.g., venous ulcers, decubitis ulcers and diabetic ulcers.

SUMMARY OF THE INVENTION

The technology disclosed herein provides for compositions and methods of detecting infected and/or chronic wounds. The disclosed technology improves upon exiting assays by: increasing the sensitivity, precision and specificity of detection of infected wounds; providing for the ability of qualitative and quantitative measurements; and, increasing the speed of detection of infected wounds in situ and in real-time. The assays and methods described herein are partly based on the use of specific reagents that detect biomarkers and/or probes which are present in infected or chronic wounds. The detection process may involve use of reagents that are specific to the markers present in infected wounds but not non-infected or non-chronic wounds and the detection step may involve qualitative or quantitative measurements of the signal(s) that are generated when the probe is acted upon by the marker. In embodiments wherein the detection method involves detection of enzymes present in wounds, the probes preferably comprise modified enzyme substrates that are specific to the enzyme, which generate signals that may be optionally amplified. This greatly improves efficiency and specificity of detection. Moreover, a plurality of detection probes, each specific for one or more targets, e.g., enzymes that are specific to the wounds, may be employed. This greatly helps to maximize both efficiency and accuracy of diagnostic assays while minimizing the incidence of false positives (e.g., due non-specific interactions and/or target redundancy). Furthermore, the experimental results disclosed herein confirm that the novel probes and the assay techniques based thereon are capable of detecting and characterizing various types of wounds. Finally, the reagents of the disclosed technology may be used together with therapeutic molecules such as antibiotics, antifungal agents, etc. to monitor and evaluate treatment and management of chronic wounds.

In one embodiment, provided herein is a wound-dressing material comprising a compound of Formula I comprising the structure M-L-R, wherein M is a gel-forming polymer; R is a reporter molecule; and L is a linker that is either absent or present, and L, when present, connects M and R. In another embodiment, provided herein is a compound comprising the structure M-R, wherein M is a gel-forming polymer and R is a reporter molecule.

In another embodiment, provided herein is a compound comprising the structure M-R, wherein M is a gel-forming polymer and R is a reporter molecule and wherein M is covalently or non-covalently conjugated with R.

In another embodiment, provided herein is a wound-dressing material comprising a compound of Formula I comprising the structure M-L-R, wherein M is a gel-forming polymer; R is a reporter molecule; and L is a linker that is covalently or non-covalently conjugated, independently of each other, with M and R.

In another embodiment, provided herein is a wound-dressing material comprising a compound of Formula I comprising the structure M-L-R, wherein M is a gel-forming polymer; R is a reporter molecule; and L is a linker, wherein the reporter R comprises an enzyme substrate.

In another embodiment, provided herein is a wound-dressing material comprising a compound of Formula I comprising the structure M-L-R, wherein M is a gel-forming polymer; R is a reporter molecule; and L is a linker, wherein the reporter R comprises an enzyme substrate which is a sugar, a polysaccharide, a nucleic acid, an amide, a peptide, a protein, a lipid, or a derivative thereof or a combination thereof. Particularly under this embodiment, the substrate is a sugar, a polysaccharide, an amide, a peptide or a protein, or a derivative thereof. Especially under this embodiment, the substrate is a peptide substrate (PEP) comprising an amino acid or a peptide comprising a plurality of amino acids.

In another embodiment, provided herein is a wound-dressing material comprising a compound of Formula I comprising the structure M-L-R, wherein M is a gel-forming polymer; R is a reporter molecule; and L is a linker that is either absent or present, and L, when present, connects M and R, wherein M is selected from cellulose, carboxymethylcellulose, pectin, alginate, chitosan, hyaluronic acid, polysaccharide, or gum-derived polymer, or a derivative thereof or any mixture or a combination thereof. Particularly under this embodiment, the polymer is carboxymethylcellulose (CMC) or a salt thereof.

In another embodiment, provided herein is a wound-dressing material comprising a compound of Formula I comprising the structure M-L-R, wherein M is a gel-forming polymer; R is a reporter molecule; and L is a linker that is either absent or present, and L, when present, connects M and R, wherein M comprises about 200 to about 4000 monomeric units. Particularly under this embodiment, M comprises about 500 to about 2000 monomeric units.

In another embodiment, provided herein is a wound-dressing material comprising a compound of Formula I comprising the structure M-L-R, wherein M is a gel-forming polymer; R is a reporter molecule; and L is a linker that is either absent or present, and L, when present, connects M and R, wherein L comprises a monomer or a neutral polymer which is an ethoxylated polyhydric alcohol, a polyvinyl pyrrolidone polymer, a polypropylene, a polyalkylene glycol, a polyamine or an ether, an amide, or an ester thereof. Particularly under this embodiment, L comprises 1-10 monomeric units of an ethoxylated polyhydric alcohol, a polyvinyl pyrrolidone polymer, a polypropylene, a polyalkylene glycol, a polyamine or an ether, an amide, or an ester thereof. More specifically under this embodiment, L comprises at least one polypropylene glycol subunit.

In another embodiment, provided herein is a wound-dressing material comprising a compound of Formula I comprising the structure M-L-R, wherein M is a gel-forming polymer; R is a reporter molecule; and L is a linker that is either absent or present, and L, when present, connects M and R, wherein R comprises a detectable label. Particularly under this embodiment, the detectable label is selected from the group consisting of a luminescent molecule, a chemiluminescent molecule, a fluorochrome, a fluorescent quenching agent, a lipid, a colored molecule, a radioisotope, a scintillant, biotin, avidin, streptavidin, protein A, protein G, an antibody or a fragment thereof, a polyhistidine, Ni2+, a Flag tag, a myc tag, a heavy metal, and an enzyme.

In another embodiment, provided herein is a wound-dressing material comprising a compound of Formula I comprising the structure M-L-R, wherein M is a gel-forming polymer; R is a reporter molecule; and L is a linker that is either absent or present, and L, when present, connects M and R, wherein R comprises a fluorescent molecule selected from the group consisting of fluorescein, rhodamine, tetramethylrhodamine, R-phycoerythrin, Cy-3, Cy-5, Cy-7, Texas Red, Phar-Red, allophycocyanin (APC), fluorescein amine, eosin, dansyl, umbelliferone, 5-carboxyfluorescein (FAM), 2'7'-dimethoxy-4'5'-dichloro-6-carboxyfluorescein (JOE), 6 carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), 5-(2'-aminoethyl)aminonaphthalene-1-sulfonic acid (EDANS), 4-acetamido-4'-isothiocyanatostilbene-2,2'disulfonic acid, acridine, acridine isothiocyanate, r-amino-N-β-vinylsulfonyl)phenylnaphthalimide-3,5, disulfonate (Lucifer Yellow VS), N-(4-anilino-1-naphthyl)maleimide, anthranilamide, Brilliant Yellow, coumarin, 7-amino-4-methylcoumarin, 7-amino-4-trifluoromethylcouluarin (Coumarin 151), cyanosine, 4', 6-diaminidino-2-phenylindole (DAPI), 5',5"-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 4-dimethylaminophenylazophenyl-4'-isothiocyanate (DABITC), eosin isothiocyanate, erythrosin B, erythrosin isothiocyanate, ethidium, 5-(4,6-dichlorotriazin-2-yl)aminofluorescein (DTAF), QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4, lissamine rhodamine B sulfonyl chloride, rhodamine B, rhodamine 123, rhodamine X, sulforhodamine B, sulforhodamine 101, sulfonyl chloride derivative of sulforhodamine 101, tetramethyl rhodamine, riboflavin, rosolic acid, and terbium chelate derivatives.

In another embodiment, provided herein is a wound-dressing material comprising a compound of Formula I comprising the structure M-L-R, wherein M is a gel-forming polymer; R is a reporter molecule; and L is a linker that is either absent or present, and L, when present, connects M and R, wherein R comprises a detectable label and a quencher molecule. Particularly under this embodiment, the reporter comprising the quencher molecule is activated by an enzyme or a product thereof.

In another embodiment, provided herein is a wound-dressing material comprising a compound of Formula I comprising the structure M-L-R, wherein M is a gel-forming polymer; R is a reporter molecule; and L is a linker that is either absent or present, and L, when present, connects M and R, wherein the reporter molecule or a portion thereof is released upon interaction with an enzyme. Particularly under this embodiment, the reporter molecule comprises a detectable label which is released upon interaction with the enzyme.

In another embodiment, provided herein is a wound-dressing material comprising a compound of Formula I comprising the structure M-L-R, wherein M is a gel-forming polymer; R is a reporter molecule; and L is a linker that is either absent or present, and L, when present, connects M and R, wherein the reporter molecule comprises a substrate that is specific for a wound-specific enzyme, which forms a product when acted upon by the enzyme. Particularly under this embodiment, the wound-specific enzyme is a protease. More particularly under this embodiment, the reporter comprises a substrate that is specific for a wound-specific enzyme selected from the group consisting of MMP-1 (collagenase), MMP-2 (gelatinase A), MMP-3 (stomelysin 1), MMP-8 (neutrophil collagenase), MMP-9 (gelatinase B), human neutrophil elastase (HNE), cathepsin G, urokinase-type plasminogen activator (uPA), and lysozyme. Especially under this embodiment, the reporter comprises a substrate that is specific for MMP-2 and MMP-9 or a combination thereof.

In another embodiment, provided herein is composition comprising a carrier and a wound-dressing material comprising a compound of Formula I comprising the structure M-L-R, wherein M is a gel-forming polymer; R is a reporter molecule; and L is a linker that is either absent or present, and L, when present, connects M and R. Particularly under this embodiment, the composition is a pharmaceutical composition. More particularly under this embodiment, the pharmaceutical composition comprises an antibiotic compound or a wound-healing peptide. Especially under this embodiment, the antibiotic is selected from the group consisting of β-lactams, fluoroquinolones, aminoglycosides, tetracyclines, glycylcyclines and polymyxins and/or the wound-healing peptide is fibroblast growth factor (FGF) or platelet derived growth factor (PDGF).

In another embodiment, provided herein is composition comprising an article comprising a wound dressing material as hereinbefore described.

In another embodiment, provided herein is a method of diagnosing a status of a wound in a subject in need thereof, comprising, contacting the wound with the wound dressing material as hereinbefore described to permit conversion of the reporter molecule into a detectable signal and detecting the signal. Particularly under this embodiment, the conversion of the reporter molecule into a detectable signal is carried out by a wound-specific protease, e.g., a wound specific protease selected from the group consisting of MMP-1 (collagenase), MMP-2 (gelatinase A), MMP-3 (stomelysin 1), MMP-8 (neutrophil collagenase), MMP-9 (gelatinase B), human neutrophil elastase (HNE), cathepsin G, urokinase-type plasminogen activator (uPA), and lysozyme. Especially under this embodiment, the method comprises diagnosing a chronic wound or an infected wound.

In another embodiment, provided herein is a method of diagnosing a status of a wound in a subject in need thereof, comprising, contacting the wound with the wound dressing material as hereinbefore described to permit conversion of the reporter molecule into a detectable signal and detecting the signal; assessing a parameter which is an activity or level of a wound-specific enzyme in the wound; comparing the parameter to a threshold level; and making a determination that the wound is chronic or infected if the level of the parameter in the wound is higher than the threshold level. Under this embodiment, the parameter is an amount or activity of a wound-specific protease is selected from the group consisting of MMP-1 (collagenase), MMP-2 (gelatinase A), MMP-3 (stomelysin 1), MMP-8 (neutrophil collagenase), MMP-9 (gelatinase B), human neutrophil elastase (HNE), cathepsin G, urokinase-type plasminogen activator (uPA), and lysozyme. Particularly under this embodiment, the diagnostic method is performed in situ.

In another embodiment, provided herein is a method of treating a wound in a subject in need thereof, comprising, contacting the wound with the wound dressing material as hereinbefore described. Particularly under this embodiment, the dressing material is topically or dermally applied at the site of the wound.

In another embodiment, provided herein is a method for making a compound of Formula I according to the foregoing, wherein L is absent, comprising, conjugating the gel-forming polymer M with the reporter region R, wherein M and R are each, individually, as described previously. Particularly under this embodiment, the gel-forming polymer M is conjugated to the reporter region R via a covalent linkage selected from the group consisting of a peptide linkage, a glycosidic linkage, an ester linkage, an oxyester linkage, an amide linkage, an amido linkage, an oxyamido linkage, an ether linkage, a sulfonyl linkage, a sulfinyl linkage, a sulfonamide linkage, an alkoxy linkage, an alkylthio linkage, an alkylamino linkage, or a combination thereof. Especially under this embodiment, the gel-forming polymer M is conjugated to the reporter region R via a glycosidic linkage or a peptide linkage.

In another embodiment, provided herein is a method for making a compound of Formula I according the foregoing, wherein L is present, comprising, conjugating the gel-forming polymer M with the linker L to generate a precursor molecule M-L; conjugating the precursor molecule M-L to a reporter region R, wherein M, L and R are each, individually, as described previously. Particularly under this embodiment, the gel-forming polymer M is conjugated to linker L and/or the linker L is conjugated to the reporter region R via a covalent linkage selected from the group consisting of an ester linkage, an oxyester linkage, an amide linkage, an amido linkage, an oxyamido linkage, an ether linkage, a sulfonyl linkage, a sulfinyl linkage, a sulfonamide linkage, an alkoxy linkage, an alkylthio linkage, an alkylamino linkage, or a combination thereof.

In another embodiment, provided herein is a method for making a compound of Formula I according to the foregoing, wherein L is present, comprising, conjugating the linker L with the reporter R to generate a precursor molecule L-R; conjugating the precursor molecule L-R to a gel-forming polymer M, wherein M, L and R are each, individually, as described previously. Particularly under this embodiment, the gel-forming polymer M is conjugated to linker L and/or the linker L is conjugated to the reporter region R via a covalent linkage selected from the group consisting of an ester linkage, an oxyester linkage, an amide linkage, an amido linkage, an oxyamido linkage, an ether linkage, a sulfonyl linkage, a sulfinyl linkage, a sulfonamide linkage, an alkoxy linkage, an alkylthio linkage, an alkylamino linkage, or a combination thereof.

In another embodiment, provided herein are wound dressing materials comprising a compound comprising the structure M-L-PEP (Formula II), wherein M is a gel-forming polymer; PEP is a peptide and at least one amino acid; and L is a linker that is either absent or present, and L, when present, connects M and PEP.

In another embodiment, provided herein are wound dressing materials selected from the group consisting of:

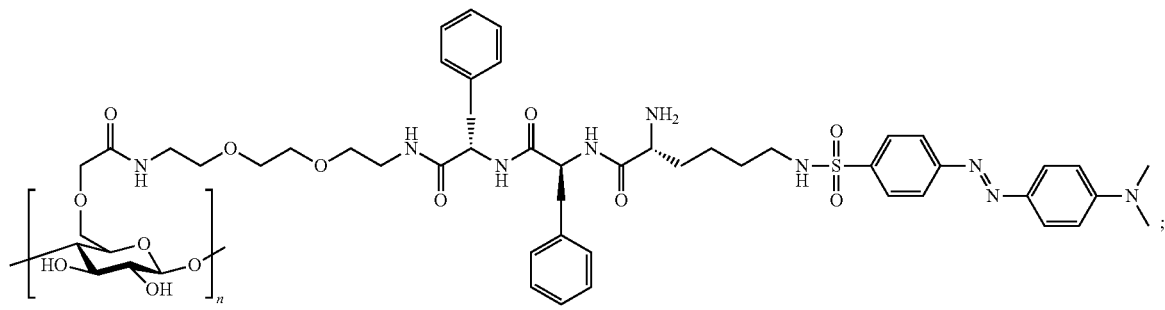

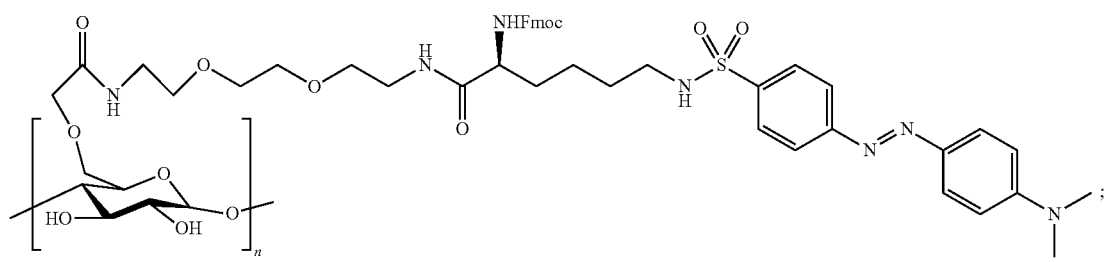

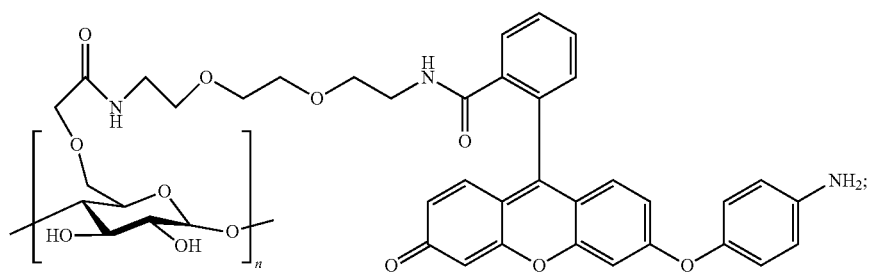

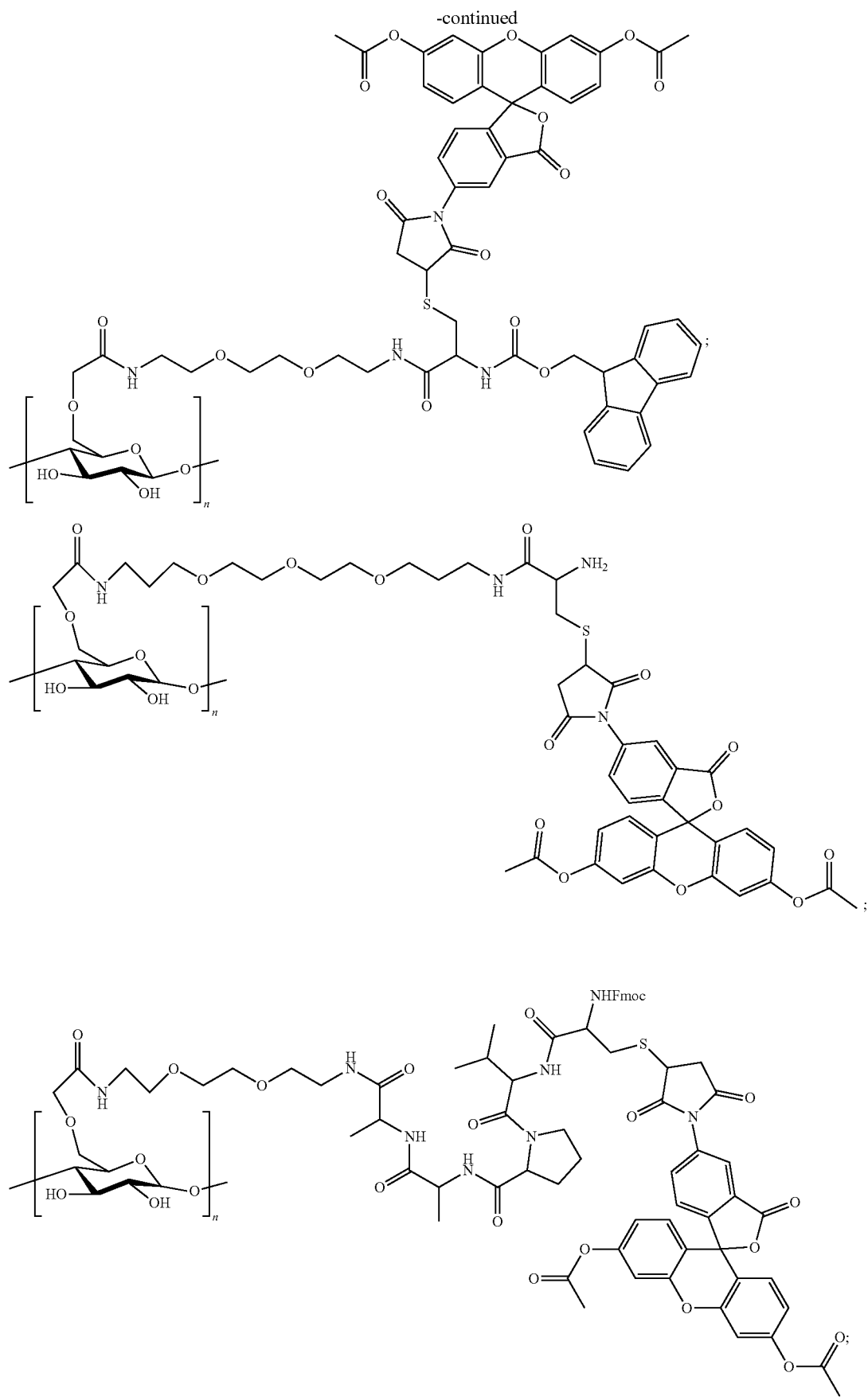

11
12
-continued
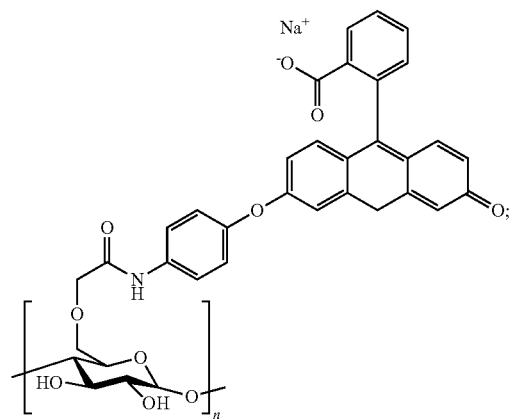
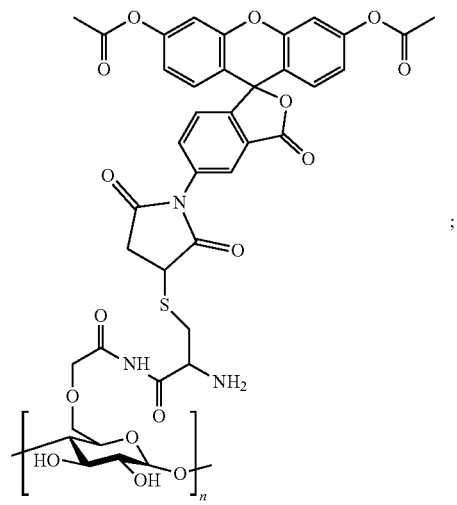
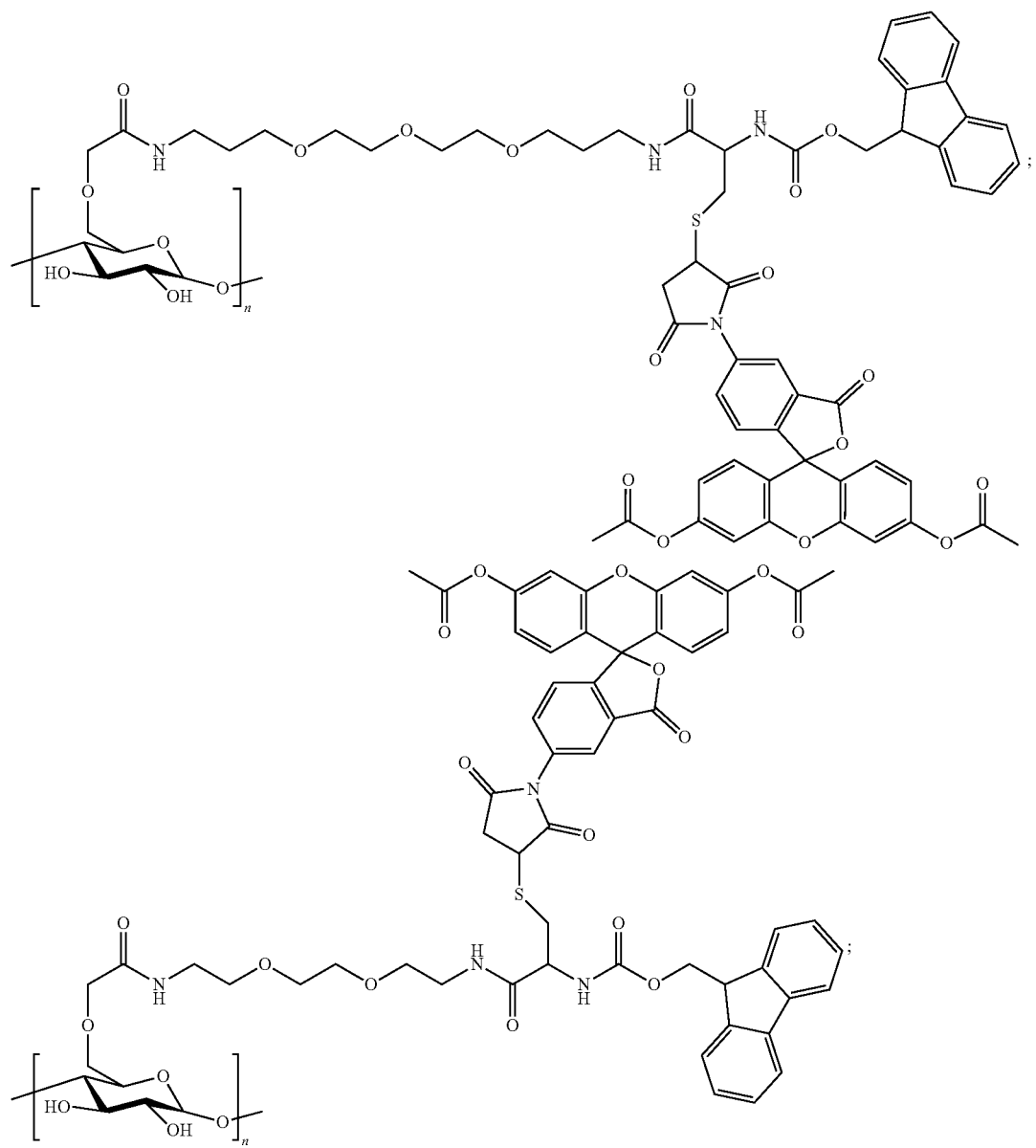

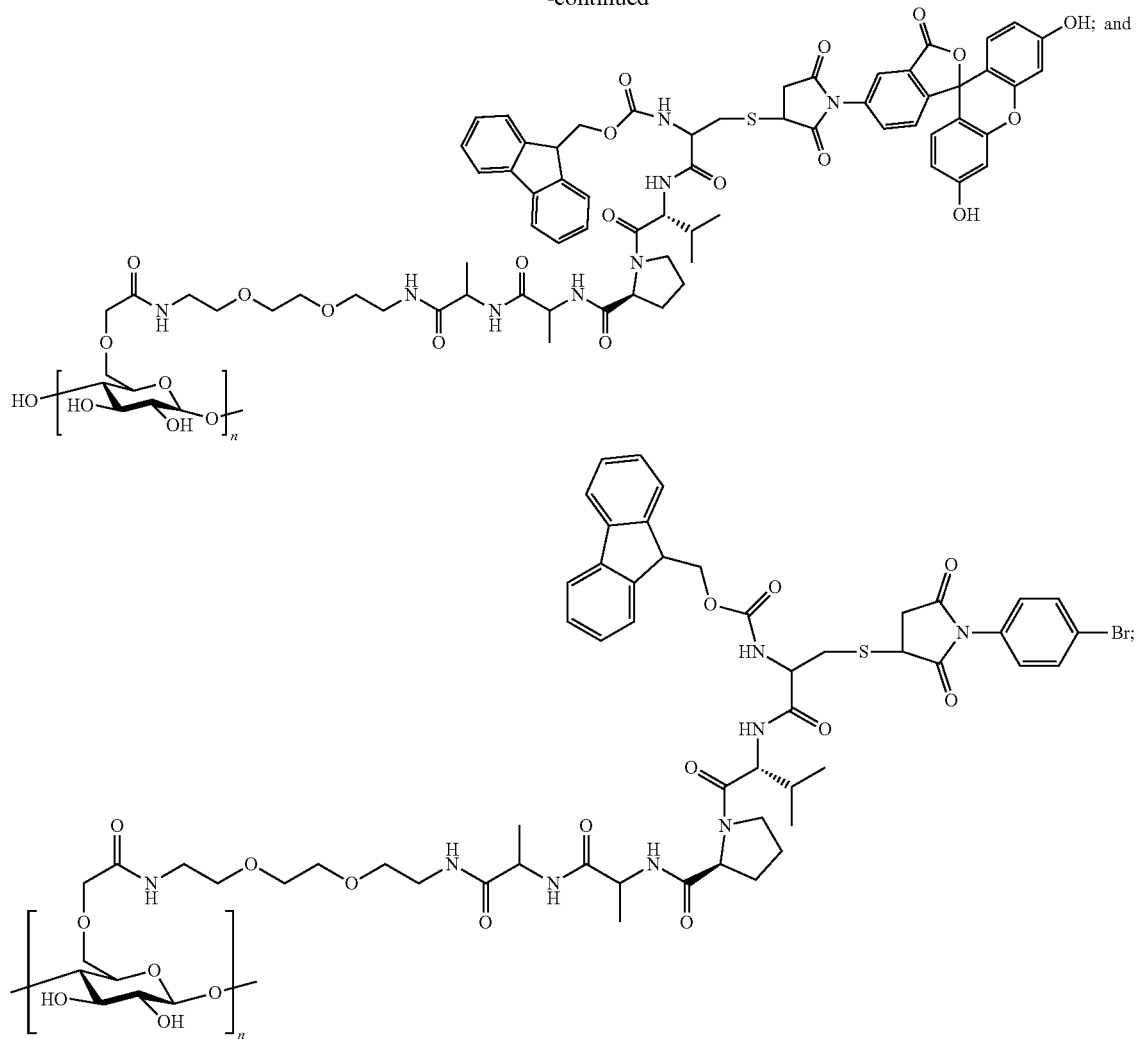

wherein n=200-4000.

It is understood that other embodiments and configurations of the subject technology will become readily apparent to those skilled in the art from the following detailed description, wherein various configurations of the subject technology are shown and described by way of example or illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

To understand the present disclosure, it will now be described by way of example, with reference to the accompanying drawings in which embodiments and examples of the disclosures are illustrated and, together with the descriptions below, serve to explain the principles of the disclosure.

DETAILED DESCRIPTION

Figure 1:
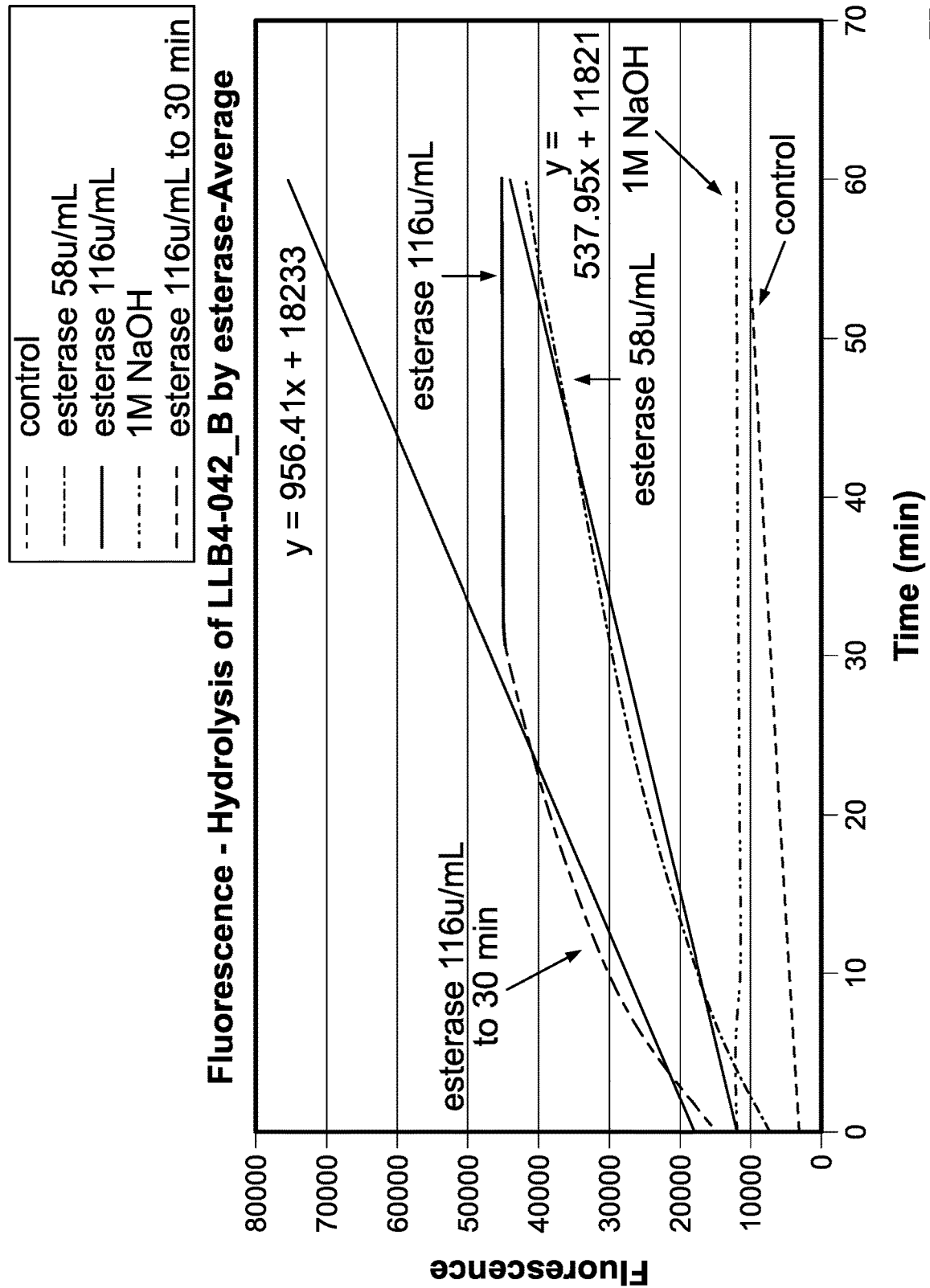
FIG. 1 shows quantitation of enzyme efficacy of Polymer 12 using a fluorescence-based study.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

I. Definitions

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

"Substantially" or "essentially" means nearly totally or completely, for instance, 80%-95% or greater of some given quantity, e.g., at least 85%, at least 87%, at least 88%, at least 89%, at least 90%, at least 91%, at least 92%, at least 93%, at least 94%, at least 95%, at least 96%, at least 97%, at least 98%, at least 99%, at least 99.9%, or more % by weight or volume or any other parameter being measured. "Substantially free" means nearly totally or completely absent of some given quantity such as being present at a level of less than about 1% to about 20% of some given quantity, e.g., less than 10%, less than 9%, less than 8%, less than 7%, less than 6%, less than 5%, less than 4%, less than 3%, less than 2%, less than 1%, less than 0.5%, less than 0.1%, or less % by weight or volume or any other parameter being measured. In some embodiments, "substantially free" means presence at a level of less than or equal to 1-5% by weight of the pharmaceutical composition.

II. Compositions and Systems for Use in a Wound Dressing

Provided herein are modified wound dressing materials to be used in wound dressings for the therapy and diagnosis of wounds and wound management, wherein the wound dressing materials when in use indicate the presence of elevated enzyme levels in a wound in situ.

As used herein, a "wound" refers to physical disruption of the continuity or integrity of tissue structure. "Wound healing" refers to the restoration of tissue integrity. It will be understood that this can refer to a partial or a full restoration of tissue integrity. Treatment of a wound thus refers to the promotion, improvement, progression, acceleration, or otherwise advancement of one or more stages or processes associated with the wound healing process.

The wound may be acute or chronic. Chronic wounds, including pressure sores, venous leg ulcers and diabetic foot ulcers, can simply be described as wounds that fail to heal. Whilst the exact molecular pathogenesis of chronic wounds is not fully understood, it is acknowledged to be multifactorial. As the normal responses of resident and migratory cells during acute injury become impaired, these wounds are characterized by a prolonged inflammatory response, defective wound extracellular matrix (ECM) remodeling and a failure of re-epithelialization.

The wound may be any internal wound, e.g., where the external structural integrity of the skin is maintained, such as in bruising or internal ulceration, or external wounds, particularly cutaneous wounds, and consequently the tissue may be any internal or external bodily tissue. In one embodiment the tissue is skin (such as human skin), i.e. the wound is a cutaneous wound, such as a dermal or epidermal wound.

The human skin is composed of two distinct layers, the epidermis and the dermis, below which lies the subcutaneous tissue. The primary functions of the skin are to provide protection to the internal organs and tissues from external trauma and pathogenic infection, sensation and thermoregulation.

The outermost layer of skin, the epidermis, is approximately 0.04 mm thick, is avascular, is comprised of four cell types (keratinocytes, melanocytes, Langerhans cells, and Merkel cells), and is stratified into several epithelial cell layers. The inner-most epithelial layer of the epidermis is the basement membrane, which is in direct contact with, and anchors the epidermis to, the dermis. All epithelial cell division occurring in skin takes place at the basement membrane. After cell division, the epithelial cells migrate towards the outer surface of the epidermis. During this migration, the cells undergo a process known as keratinization, whereby nuclei are lost and the cells are transformed into tough, flat, resistant non-living cells. Migration is completed when the cells reach the outermost epidermal structure, the stratum corneum, a dry, waterproof squamous cell layer which helps to prevent desiccation of the underlying tissue. This layer of dead epithelial cells is continuously being sloughed off and replaced by keratinized cells moving to the surface from the basement membrane. Because the epidermal epithelium is avascular, the basement membrane is dependent upon the dermis for its nutrient supply.

The dermis is a highly vascularized tissue layer supplying nutrients to the epidermis. In addition, the dermis contains nerve endings, lymphatics, collagen protein, and connective tissue. The dermis is approximately 0.5 mm thick and is composed predominantly of fibroblasts and macrophages. These cell types are largely responsible for the production and maintenance of collagen, the protein found in all animal connective tissue, including the skin. Collagen is primarily responsible for the skin's resilient, elastic nature. The subcutaneous tissue, found beneath the collagen-rich dermis, provides for skin mobility, insulation, calorie storage, and blood to the tissues above it.

Wounds can be classified in one of two general categories, partial thickness wounds or full thickness wounds. A partial thickness wound is limited to the epidermis and superficial dermis with no damage to the dermal blood vessels. A full thickness wound involves disruption of the dermis and extends to deeper tissue layers, involving disruption of the dermal blood vessels. The healing of the partial thickness wound occurs by simple regeneration of epithelial tissue. Wound healing in full thickness wounds is more complex. Cutaneous wounds contemplated herein may be either partial thickness or full thickness wounds.

Wounds contemplated herein include cuts and lacerations, surgical incisions or wounds, punctures, grazes, scratches, compression wounds, abrasions, friction wounds (e.g., nappy rash, friction blisters), decubitus ulcers (e.g., pressure or bed sores); thermal effect wounds (burns from cold and heat sources, either directly or through conduction, convection, or radiation, and electrical sources), chemical wounds (e.g. acid or alkali burns) or pathogenic infections (e.g., viral, bacterial or fungal) including open or intact boils, skin eruptions, blemishes and acne, ulcers, chronic wounds, (including diabetic-associated wounds such as lower leg and foot ulcers, venous leg ulcers and pressure sores), skin graft/transplant donor and recipient sites, immune response conditions, e.g., psoriasis and eczema, stomach or intestinal ulcers, oral wounds, including a ulcers of the mouth, damaged cartilage or bone, amputation wounds and corneal lesions.

Wound dressing materials and formulations thereof:

Embodiments described herein provide modified wound dressings, which may be used to diagnose and/or treat chronic wounds. The dressings may comprise gel-forming polymers, non-gel-forming fibers, or a combination thereof. The wound dressing materials described herein are used in methods to detect the level of one or more enzymes in a mammalian wound. In some embodiments, the wound dressing materials described herein are used in methods to diagnose a chronic wound in a mammal. In some embodiments, the wound dressing materials described herein are used in methods to diagnose an infected wound in a mammal. In other embodiments, the wound dressing materials described herein are used in methods to treat a wound in a mammal. In further embodiments, the wound dressing materials described herein are used in methods to treat a chronic wound in a mammal.

In some embodiments, the wound dressing material has the structure of Formula I:

M-L-R  Formula I wherein M is a gel-forming polymer; R is a region comprising a reporter molecule; and L is a linker that connects M and R. In one embodiment, the linker (L) is present. In another embodiment, the linker (L) is absent, in which case, the wound dressing material comprises a compound of formula M-R, wherein M and R are each, individually, as described above.

In some embodiments, the wound dressing material has the structure of Formula II:

M-L-PEP  Formula II wherein M is a gel-forming polymer; PEP is a peptide region comprising a reporter molecule and at least one amino acid; and L is a linker that connects M and PEP. In one embodiment, the linker (L) is present. In another embodiment, the linker (L) is absent, in which case, the wound dressing material comprises a compound of formula M-R, wherein M and R are each, individually, as described above.

In specific embodiments, the wound dressing material of Formula I or Formula II contains no linkers, wherein the reporter (R) or the peptide (PEP) is associated, either covalently or non-covalently, directly with the gel-forming polymer. As is understood in the art, covalent bonds involve sharing of electrons between the bonded atoms. In contrast, non-covalent bonds may include, for example, ionic interactions, electrostatic interactions, hydrogen bonding interactions, physiochemical interactions, van der Waal forces, Lewis-acid/Lewis-base interactions, or combinations thereof. Particularly, in such instance where the linker is absent, the peptide is attached or conjugated to the gel-forming polymer via covalent interaction.

The term "peptide" includes the peptide as well as pharmaceutically acceptable salts of the peptide. Typically, a peptide comprises a plurality of amino acid residues, e.g., 2, 3, 4, 5, 6, 8, 10, or more amino acid residues which are bonded to each other via covalent bonds, e.g., a peptide bond. "Amino acid residue" means the individual amino acid units incorporated into the peptides of the disclosure. As used herein, the term "amino acid" means a naturally occurring or synthetic amino acid, as well as amino acid analogs, stereoisomers, and amino acid mimetics that function similarly to the naturally occurring amino acids. Included by this definition are natural amino acids such as: 1. Histidine (His) 2. Isoleucine (Ile) 3. Leucine (Leu) 4. Lysine (Lys) 5. Methionine (Met) 6. Phenylalanine (Phe) 7. Threonine (Thr) 8. Tryptophan (Trp) 9. Valine (Val) 10. Arginine (Arg) 11. Cysteine (Cys) 12. Glutamine (Gln) 13. Glycine (Gly) 14. Proline (Pro) 15. Serine (Ser) 16. Tyrosine (Tyr) 17. Alanine (Ala) 18. Asparagine (Asn) 19. Aspartic acid (Asp) 20. Glutamic acid (Glu) 21. Selenocysteine (Sec); Unnatural Amino Acids: Citrulline; Cystine; Gama-amino butyric acid (GABA); Ornithine; Theanine and Amino Acid Derivatives such as Betaine; Carnitine; Carnosine Creatine; Hydroxytryptophan; Hydroxyproline; N-acetyl cysteine; S-Adenosyl methionine (SAM-e); Taurine; Tyramine. Amino acids containing reactive side chains, e.g., cysteine, serine, threonine, lysine, arginine, aspartate/asparagine, glutamate/glutamine, glycine, alanine, etc. are particularly employed.

In certain embodiments, the peptide may be modified, e.g., via addition, deletion, substitution of one or more amino acids, via derivatization of one or more amino acids, or cyclization, etc. In particular, the peptides are modified at the carboxy-terminal (C-terminus) or the amino-terminus (N-terminus) by adding, deleting or substituting one or more amino acids. Particularly, the peptides are modified at the C-terminus by adding at least one amino acid, especially, an amino acid containing reactive side chains, e.g., cysteine, serine, threonine, lysine, arginine, aspartate/asparagine, glutamate/glutamine, glycine, alanine, etc., wherein the reactive side chain may be employed in the conjugation with a label such as a dye. Especially under this embodiment, the peptides are modified to contain additional cysteine or serine residues at the C-terminus, the sulfur group of cysteine or the hydroxyl group of serine being used to couple with fluorescent dyes.

In a specific embodiment, the peptide containing an additional amino acid comprising a reactive side chain, e.g., SH group of cysteine may be coupled to a dye via click chemistry. Herein, the reaction between a 1,2-aminothiol and a 2-cyanobenzothiazole (CBT) may be used to make luciferin, which is fluorescent. The luciferin fluorescence can be then quantified by spectrometry following a wash, and used to determine the relative presence of the molecule bearing the 1,2-aminothiol. If the quantification of non-1,2-aminothiol-bearing protein is desired, the protein of interest can be cleaved to yield a fragment with a N' Cys that is vulnerable to the 2-CBT. See Liang et al., *J. Angew. Chem.*, Int. Ed., 48, 965, 2009.

Gel-Forming Polymer (M):

In some embodiments of a wound dressing material of Formula I or Formula II, the gel-forming polymer is a compound selected from cellulose, chemically modified cellulose, pectin, alginate, chitosan, modified chitosan, hyaluronic acid, polysaccharide, or gum-derived polymer, or a derivative thereof or any mixture or a combination thereof.

In some embodiments of a wound dressing material of Formula I or Formula II, the gel-forming polymer is selected from cellulose, carboxymethylcellulose (CMC), oxidized cellulose (or a derivative thereof), cellulose ethyl sulfonate (CES), pectin, alginate, chitosan, modified chitosan, hyaluronic acid, polysaccharide, or gum-derived polymer, or any combination or mixture thereof.

In some embodiments of a wound dressing material of Formula I or Formula II, the gel-forming polymer is cellulose or chemically modified cellulose, e.g., carboxymethylcellulose, an oxidized cellulose or a derivative thereof, cellulose ethyl sulfonate.

In one embodiment, the gel forming polymer is a derivative of a polymeric compound, e.g., cellulose derivative. The term "derivative" as used herein includes salts, amides, esters, enol ethers, enol esters, acetals, ketals, orthoesters, hemiacetals, hemiketals, acids, bases, solvates, hydrates or prodrugs of the gel forming polymer. For instance, wherein the polymer is cellulose, the hydroxyl groups (—OH) of cellulose can be partially or fully reacted with various reagents to form derivatives with useful properties, e.g., cellulose esters and cellulose ethers (—OR). In one embodiment, the derivative of cellulose is selected from carboxymethylcellulose, methylcellulose, ethylcellulose, methylethylcellulose, hydroxyethyl cellulose, hydroxypropylmethylcellulose and hydroxypropylcellulose. Such derivatives may be readily prepared by those of skill in this art using known methods for such derivatization. In certain embodiments, the derivatives may be administered to animals or humans without substantial toxic effects and either are pharmaceutically active or are prodrugs. Representative types of cellulosic derivatives are described in U.S. Pat. Nos. 7,544,640 and 9,561,188.

In another embodiment, the derivative is a salt of the polymeric compound, e.g., salts of $Li^+$, $Na^+$, $K^+$, $Rb^+$, $Mg^{2+}$, $Ca^{2+}$, $Sr^{2+}$, or $Ba^{2+}$, preferably Nat, $Mg^{2+}$, $Ca^{2+}$. Salts of cellulose, cellulose esters and cellulose ethers, such as sodium or calcium salts, are known in the art.

In some embodiments, the gel-forming polymeric compound may contain a combination or mixture of one or more of the aforementioned compounds. The term "combination" includes compounds containing more than one component, which may be conjugated or non-conjugated to one another. In one embodiment, the gel-forming polymeric compound comprises a combination of one or more of the aforementioned compounds which are conjugated to each other, e.g., via covalent or non-covalent interaction. As a particular example, the gel-forming polymer may comprise a combination of pectin and carboxymethylcellulose. See, Ninan et al., *Carbohydr Polym.* 2013 Oct. 15; 98(1):877-85; PMID: 23987424.

In some embodiments, the compounds include mixtures of the aforementioned polymeric compounds. The term "mixture" refers to a mingling together of two or more substances without the occurrence of a reaction by which they would lose their individual properties. For instance, a mixture of compound A and compound B may contain any weight ratio of compound A and compound B, such that the total weight of the mixture would amount to 100%, e.g., 99:1 weight ratio of compound A/compound B or 1:99 weight ratio of compound A/compound B. A typical mixture may contain about 2, 3, 4, 5, or more of the aforementioned polymer compounds.

In some embodiments of a wound dressing material of Formula I or Formula II, the gel-forming polymer is in the form of powder or fiber, or a combination thereof. In some embodiments of a wound dressing material of Formula I or Formula II, the gel-forming polymer is in the form of fiber. Gel-forming fibers are hygroscopic fibers which upon the uptake of wound exudate become moist, slippery, or gelatinous and thus reduces the tendency for the surrounding fibers to adhere to the wound. The gel-forming fibers can be of the type which retain their structural integrity on absorption of exudate or can be of the type which lose their fibrous form and become a structureless gel. Gel-forming fibers preferably have an absorbency of at least 2 grams 0.9% saline solution per gram of fiber (as measured by the free swell method).

In some embodiments, the wound dressing material may comprise non-gel-forming fibers. In some embodiments, the non-gel-forming fibers are selected from cellulose fiber (e.g., cotton or lyocell/TENCEL), polyester, nylon, viscose, aramid, acrylic, elastane (LYCRA), polyolefin, polylactide, silk, and natural or synthetic wool. In some embodiments, the wound dressing material comprises gel-forming polymers and non-gel-forming fibers.

In some embodiments of a wound dressing material of Formula I or Formula II, the gel-forming polymer is in the form of powder. In certain embodiments of a wound dressing material of Formula I or Formula II, powder gel-forming polymer is preferred over fibrous gel-forming fiber because of the higher degree of substitution (DoS) of the powder gel-forming polymer. In some embodiments of a wound dressing material of Formula I or Formula II, fibrous gel-forming fiber is preferred over powder gel-forming polymer.

In some embodiments of a wound dressing material of Formula I or Formula II, the gel-forming polymer has a DoS of at least 0.2, at least 0.3, at least 0.4, at least 0.5, at least 0.6, at least 0.7, at least 0.8, at least 0.9, at least 1.0, at least 1.1, at least 1.2, at least 1.3, at least 1.4, at least 1.5, at least 2.0, or more. The term DoS is understood in the art. For instance, in the context of cellulose chemistry where each anhydroglucose (β-glucopyranose) unit has three reactive (hydroxyl) groups; DoS may therefore range from zero (cellulose) to three (fully substituted cellulose).

Linker (L):

In some embodiments, wherein the wound-dressing material comprises a linker, the linker may be attached to the gel-forming polymer covalently or non-covalently. As is understood in the art, covalent bonds involve sharing of electrons. In contrast, non-covalent bonds may include, for example, ionic interactions, electrostatic interactions, hydrogen bonding interactions, physiochemical interactions, van der Waal forces, Lewis-acid/Lewis-base interactions, or combinations thereof. Particularly, the linker is attached or conjugated to the gel-forming polymer via covalent interaction.

In one embodiment, the chemical linker is a carboxylic acid having 2 to 10 carbon atoms, particularly 4 to 8 carbon atoms or especially about 4 to 6 carbon atoms.

In another embodiment, the linker is a monomer or a neutral polymer selected from the group consisting of an ethoxylated polyhydric alcohol, a polyvinyl pyrrolidone polymer, a polypropylene, a polyalkylene glycol, a polyamine, including, ethers, amides, and esters thereof.

In one embodiment, the neutral polymer is polypropylene, although a monomer thereof comprising propylene may also be used. Polypropylene (PP) is one of the most important and widely used polyolefins as matrix material because of its low density, low production costs, design flexibility and recyclability. Because polyproylene is hydrophobic, it may be incompatible with polar surfaces, such as cellulose. This issue can be resolved by incorporating functionalized polypropylene, such as poly(propylene-graft-maleic anhydride) (PP-g-MA), into the composite, wherein the carboxylic anhydride groups can provide covalent bonding to the cellulose. See, Spoljaric et al., Composites: Part A 40, 791-799, 2009.

In one embodiment, the neutral polymer linker is a polyalkylene glycol, although a monomer thereof comprising alkylene glycol may also be used. The term "polyalkylene glycol" refers to straight or branched polyalkylene glycol polymers such as polyethylene glycol, polypropylene glycol, and polybutylene glycol. A polyalkylene glycol subunit is a single polyalkylene glycol unit. For example, an example of a polyethylene glycol subunit would be an ethylene glycol, —O—CH2-CH2-O—, or propylene glycol, —O—CH2-CH2-CH2-O—, capped with a hydrogen at the chain termination point. Other examples of poly(alkylene glycol) include, but are not limited to, PEG, PEG derivatives such as methoxypoly(ethylene glycol) (mPEG), poly(ethylene oxide), PPG, poly(tetramethylene glycol), poly(ethylene oxide-co-propylene oxide), or copolymers and combinations thereof.

In another embodiment, the neutral polymer is a polyamine, although a monomer thereof comprising an amine may also be used. The term "polyamine" refers to polymers having an amine functionality in the monomer unit, either incorporated into the backbone, as in polyalkyleneimines, or in a pendant group as in polyvinyl amines.

Particularly, the linker is a PEG or a PEG derivative such as methoxypoly(ethylene glycol) (mPEG), poly(ethylene oxide), PPG, poly(tetramethylene glycol), poly(ethylene oxide-co-propylene oxide), or copolymers and combinations thereof.

In another embodiment, other hydrophilic or hydrophobic linkers may also be used as linkers, as long as they are flexible, e.g., linkers that do not contain double bonds or cyclic structures or which contain only a few double bonds or cyclic structure. Representative examples include, e.g., polyalkylene, polyhydroxyalkylene, polyalkylene succinate, polylactide, etc., with chain lengths from about 2 to about 20 chain atoms. The chain length of the polyalkyleneglycols may vary from edgy 3 units (MW about 150 Da) up to e.g., about 100 (MW about 5000). The relative amount of polyalkyleneglycol with respect to the polysaccharide may vary from about 1/200 to about 1/1, especially from about 1/50 to about 1/1.5, depending on the required thickness and the required flexibility of the product. See, U.S. Pat. No. 9,089, 614 and US PGPUB No. 2005-0079155.

In some embodiments of a wound dressing material of Formula I or Formula II, the linker L comprises 1 to about 20 monomeric units, e.g., of the natural polymer, e.g., 1, 2, 3, 4, 5, 6, 7, 8, 9, 10, 11, 12, 13, 14, 15, 16, 17, 18, 19, 20 or more monomer units. In specific embodiments, the linker comprises from 1 to about 5 ethylene glycol units or a derivative thereof, from 2 to about 5 ethylene glycol units or a derivative thereof, from 2 to about 8 ethylene glycol units or a derivative thereof, from 2 to about 10 ethylene glycol units or a derivative thereof or from 5 to about 10 ethylene glycol units or a derivative thereof.

In some embodiments, the linker L comprises a chemical moiety that is a product of a nucleophilic reaction. In general, the term "nucleophile" is art-recognized to mean a chemical group having a reactive pair of electrons that reacts with a compound by displacing a leaving group (commonly another nucleophile), such as commonly occur in aliphatic chemistry as unimolecular (known as "SN1") or bimolecular ("SN2") reactions. Examples of nucleophiles include uncharged compounds such as amines, mercaptans, and alcohols, and charged groups such as alkoxides, thiols, thiolates, carbanions, and a variety of organic and inorganic anions. Illustrative anionic nucleophiles include, inter alia, simple anions such as azide, cyanide, thiocyanate, acetate, formate, or chloroformate, and bisulfite.

In some embodiments, the linker L comprises a maleimide-thiol adduct. Maleimides are particularly useful for conjugation to thiol-containing substances, e.g., thiol-containing amino acids such as cysteine. A thiol group reacts with a maleimides by added across the double bond to form a thioether. Maleimides are selective for the thiol of cysteine over methionine, histidine, or tyrosine. Reaction of maleimides with amines usually requires a higher pH than reaction of maleimides with thiols. Hydrolysis of maleimides competes significantly with thiol modification, particularly above pH 8. See, US PGPUB No. 2007-0087446.

In some embodiments, L comprises a haloacetamide-thiol conjugation product.

Haloacetamides, e.g., iodoacetamide or bromoacetamide, may also be used to bind covalently with the thiol group of amino acids, e.g., cysteine.

In some embodiments, the linker L comprises a compound containing a thiol or a disulfide, which can be used analogously to maleimide. See, Zalipsky et al., Bioconjug. Chem. 6, 150-165, 1995; Greenwald et al. Crit. Rev. Ther. Drug Carrier Syst. 17, 101-161, 2000; and Herman et al., Macromol. Chem. Phys. 195, 203-209, 1994. See also, U.S. Pat. No. 7,432,330.

Reporters and Markers:

In some embodiments, the wound dressing materials comprise a region comprising a reporter molecule. Particularly, the reporter is a substrate for one or more wound-specific markers, e.g., enzymes found in a wound environment. As used herein, a "wound specific enzyme" is an enzyme that is differentially expressed in a wound. By "differential expression" it is meant that the level or the activity of the enzyme is higher or lower in the wound microenvironment compared to other sites, e.g., normal tissue or surrounding tissue. Particularly, differential expression implies higher level of expression or activity of the enzyme in the wound microenvironment compared to normal or unwounded tissue. Differential expression of enzyme may be analyzed by routine means. For example, levels of enzyme in a sample may be analyzed by ELISA assays or other immunoassays. Activities of the enzyme may be analyzed by measuring rates of loss of a substrate and/or rates of formation of the product, e.g., using mass spectroscopy or HPLC. Such techniques are known in the art and are described in the Examples section.

In one embodiment, the marker is an enzyme selected from the group consisting of hydrolases, proteases, esterases, and peroxidases.

In one embodiment, the marker is a hydrolase. As used herein, a "hydrolase" or "hydrolytic enzyme" is an enzyme that catalyzes the hydrolysis of a chemical bond, e.g., esterases and nucleases (break ester bonds); glycolases (break glycosidic linkers); peptidases (break peptide bonds), etc.

In one embodiment, the marker is a protease enzyme. The protease may be a sequence-specific or a generic protease. Particularly, the term "sequence-specific protease" means a protease recognizing a specific sequence of a peptide for its digesting (for example, caspase), and is distinguished from a generic protease (for example, trypsin) that sequentially decomposes a peptide from one end thereof or digest a peptide in a sequence-nonspecific manner. For sequence specificity, the amino acid sequence of the peptide substrate may comprise four or more amino acid (a.a.) residues. The recognition site and the digestion site may be close to each other.

As used herein, the term "substrate peptide for a protease" means a peptide comprising an amino acid sequence of a protein, which is recognized by the protease as a substrate for its protease activity, e.g., as a substrate that can be cleaved into one or more products. In some embodiments, the wound dressing materials comprise a peptide region comprising a peptide sequence comprising a plurality of amino acids. The term "plurality" means two or more units, e.g., amino acids, although the individual units need not be structurally and/or functionally different.

In one embodiment, the peptide comprises natural amino acids. In other embodiments, synthetic peptides containing one or more non-natural amino acids may also be used.

In certain embodiments, a plurality of substrates, each of which is specific for a particular enzyme, may be used. In other embodiments, a plurality of substrates, each of which is specific for a plurality of enzymes, may also be used.

In one embodiment, the protease enzyme is an exopeptidase or an endopeptidase. Exopeptidases degrade the structure only near the ends of the peptide chain; endopeptidases are able to cleave internal bonds within the peptide. These classes are also split into the subgroups: cysteine-protease, a serine-protease, a threonine-protease, aspartic-protease, a glutamic-protease, a metallo-protease etc. Each are able to digest specific protein linkages by hydrolysis of the peptide bond.

In one embodiment, the protease is specific to a wound. As used herein, a "wound specific protease" is a protease that is differentially expressed in a wound. By "differential expression" it is meant that the level or the activity of the protease is higher or lower in the wound microenvironment compared to other sites, e.g., normal tissue or surrounding tissue. Particularly, differential expression implies higher level of expression or activity of the protease in the wound microenvironment compared to unwounded tissue. Differential expression of proteases may be analyzed by routine means. For example, levels of proteases in a sample may be analyzed by ELISA assays or other immunoassays. Activities of the proteases may be analyzed by measuring rates of loss of a peptide substrate and/or rates of formation of the product, e.g., using mass spectroscopy or HPLC. Such techniques are known in the art and are described in the Examples section.

In one embodiment, the wound specific protease is selected from the group consisting of MMP-1 (collagenase), MMP-2 (gelatinase A), MMP-3 (stomelysin 1), MMP-8 (neutrophil collagenase), MMP-9 (gelatinase B), human neutrophil elastase (HNE), cathepsin G, urokinase-type plasminogen activator (uPA), and lysozyme.

In some embodiments, the substrate is a peptide sequence specific for collagenase. In some embodiments, the substrate is a peptide sequence specific for MMP-2. In some embodiments, the substrate is a peptide sequence specific for MMP-3. In some embodiments, the substrate is a peptide sequence specific for neutrophil collagenase. In some embodiments, the substrate is a peptide sequence specific for gelatinase. In some embodiments, the substrate is a peptide sequence specific for human neutrophil elastase. In some embodiments, the substrate is a peptide sequence specific for cathepsin G. In some embodiments, the substrate is a peptide sequence specific for urokinase-type plasminogen activator. In some embodiments, the substrate is a peptide sequence specific for lysozyme. In some embodiments, the substrate is a sugar that is cleavable by lysozyme.

In one specific embodiment, the wound-specific protease is a matrix metalloproteinase (MMP) selected from the group consisting of MMP-1, MMP-2, MMP-8 and MMP-9 (collagenase), or a combination thereof. MMP-1 (UNIPROT accession Nos. P03956 [human] and Q9EPL5 [mouse]) is also known as interstitial collagenase and fibroblast collagenase. MMP-2 (UNIPROT accession Nos. P08253 [human] and P33434 [mouse]) is also known as gelatinase. MMP-8 (UNIPROT accession Nos. P22894 [human] and 070138 [mouse]) is also known as PMNL collagenase (MNL-CL). MMP-9 (UNIPROT accession Nos. P14780 [human] and P41245 [mouse]) is also known as gelatinase B (GELB).

In one specific embodiment, the MMP is MMP-2 or MMP-9, or a combination thereof.

In some embodiments, matrix metalloproteinase (MMP) activity levels of about 5 U/mL to about 30 U/mL, including all values in between, e.g., about 6 U/mL, about 7 U/mL, about 8 U/mL, about 9 U/mL, about 10 U/mL, about 11 U/mL, about 12 U/mL, about 13 U/mL, about 14 U/mL, about 15 U/mL, about 16 U/mL, about 17 U/mL, about 18 U/mL, about 19 U/mL, about 20 U/mL, about 21 U/mL, about 22 U/mL, about 23 U/mL, about 24 U/mL, about 25 U/mL, or more, indicate chronic wound infection. As is understood in the art, Units of activity (U) are typically used to describe enzyme catalytic activity, where a unit (U) refers to the amount of enzyme that catalyzes the conversion of 1 micromole (μmole) of substrate per minute. Thus, 1 enzyme unit (U)=1 μmol/min, where μmol refers to the amount of substrate converted.

In one specific embodiment, the MMP is MMP-2 or MMP-9, wherein MMP-2 and MMP-9 activity levels of at least 10.5 U/mL indicate chronic wound infection.

Any peptide cleavable by MMP may be used in accordance with the embodiment described herein. For instance, See Table 1 of U.S. Pat. No. 7,148,194, herein incorporated by reference for this subject matter.

Table 1 shows the various substrates and their specificity to different isoforms of human MMPs. The data are presented in Table 3 of Nagase et al. ("Substrate specificity of MMPs," in Matrix Metalloproteinase Inhibitors in Cancer Therapy, Clendeninn & Appelt Eds., Springer Science Media New York, 2001), which is incorporated by reference herein.

TABLE 1

| Peptide sequence | Relative rate | | | | | |
|---|---|---|---|---|---|---|
| | MMP-1 | MMP-8 | MMP-2 | MMP-9 | MMP-3 | MMP-7 |
| Gly-Pro-Gln-Gly#Ile-Ala-Gly-Gln | 100 | 100 | 100 | 100 | 100 | 100 |
| Gly-Pro-Gln-Gly#Leu-Ala-Gly-Gln | 130 | 180 | 88 | 80 | 110 | 300 |
| Gly-Pro-Gln-Gly#Trp-Ala-Gly-Gln | <0.5 | 49 | <5.0 | <5.0 | 120 | <5.0 |
| Gly-Pro-Gln-Gly#Pro-Ala-Gly-Gln | <0.5 | <0.5 | <5.0 | <5.0 | <0.5 | <5.0 |
| Gly-Pro-Gln-Gly#Glu-Ala-Gly-Gln | <0.5 | <0.5 | <5.0 | <5.0 | <0.5 | 8.0 |
| Gly-Pro-Gln-Gly#Tyr-Ala-Gly-Gln | 50 | 390 | 50 | 96 | 150 | 21 |
| Gly-Pro-Gln-Gly#Phe-Ala-Gly-Gln | 20 | 46 | 55 | 24 | 140 | 74 |
| Gly-Pro-Gln-Gly#Met-Ala-Gly-Gln | 110 | 84 | 230 | 170 | 60 | 89 |
| Gly-Pro-Gln-Gly#Val-Ala-Gly-Gln | 9.1 | 9.0 | 30 | 25 | 53 | 17 |
| Gly-Pro-Gln-Gly#Gln-Ala-Gly-Gln | 28 | 10 | 34 | 20 | 38 | <5.0 |
| Gly-Pro-Gln-Gly#Ser-Ala-Gly-Gln | 5.9 | 1.6 | 15 | <5.0 | 45 | 5.5 |
| Gly-Pro-Gln-Gly#Arg-Ala-Gly-Gln | <0.5 | <0.5 | <5.0 | <5.0 | <4.9 | <5.0 |
| Gly-Pro-Gln-Gly#Ile-Phe-Gly-Gln | 369 | 510 | 380 | 390 | 130 | 140 |
| Gly-Pro-Gln-Gly#Ile-Trp-Gly-Gln | 840 | 930 | 310 | 140 | 280 | 330 |
| Gly-Pro-Gln-Gly#Ile-Leu-Gly-Gln | 430 | 400 | 400 | 240 | 280 | 250 |
| Gly-Pro-Gln-Gly#Ile-Hyp-Gly-Gln | 7.3 | 1.5 | 32 | 11 | 42 | 8.0 |
| Gly-Pro-Gln-Gly4Ile-Arg-Gly-Gln | 180 | 170 | 180 | 200 | 250 | 270 |
| Gly-Pro-Gln-Gly#Ile-Glu-Gly-Gln | 35 | 59 | 85 | 130 | 58 | 86 |
| Gly-Pro-Gln-Gly#Ile-Ala-Val-Gln | 100 | 57 | 26 | 49 | 170 | 170 |
| Gly-Pro-Gln-Gly#Ile-Ala-Arg-Gln | 55 | 34 | 35 | 45 | 490 | 220 |
| Gly-Pro-Gln-Gly#Ile-Ala-Met-Gln | 130 | 34 | 40 | 35 | 810 | 450 |
| Gly-Pro-Gln-Gly#Ile-Ala-Ala-Gln | 220 | 120 | 180 | 140 | 280 | 300 |
| Gly-Pro-Gln-Gly#Ile-Ala-Ser-Gln | 91 | 58 | 320 | 130 | 230 | 150 |
| Gly-Pro-Gln-Gly#Ile-Ala-Gly-Ala | 86 | 110 | 85 | 110 | 130 | 91 |
| Gly-Pro-Gln-Gly#Ile-Ala-Gly His | 91 | 145 | 150 | 120 | 110 | 87 |
| Gly-Pro-Gln-Gly#Ile-Ala-Gly-Thr | 160 | 145 | 59 | 160 | 72 | 100 |
| Gly-Pro-Gln-Met#Ile-Ain-Gly-Gln | 200 | 140 | 22 | 12 | 110 | 150 |

TABLE 1-continued

| Peptide sequence | Relative rate | | | | | |
|---|---|---|---|---|---|---|
| | MMP-1 | MMP-8 | MMP-2 | MMP-9 | MMP-3 | MMP-7 |
| Gly-Pro-Gln-Glu#Ile-Ala-Gly-Gln | 28 | 330 | 15 | 29 | 190 | 170 |
| Gly-Pro-Gln-Tyr#Ile-Ala-Gly-Gln | 130 | 180 | 58 | 30 | 68 | 34 |
| Gly-Pro-Gln-Ala#Ile-Ala-Gly-Gln | 600 | 320 | 96 | 110 | 300 | 530 |
| Gly-Pro-Gln-Pro#Ile-Ala-Gly-Gln | 260 | 190 | 32 | 46 | 170 | 140 |
| Gly-Pro-Gln-Gln#Ile-Ala-Gly-Gln | 140 | 150 | 25 | 13 | 140 | 180 |
| Gly-Pro-Gln-Phe#Ile-Ala-Gly-Gln | 95 | 170 | 15 | 26 | 68 | 63 |
| Gly-Pro-Gln-Leu#Ile-Ala-Gly-Gln | 27 | 54 | 21 | 8.8 | 170 | 49 |
| Gly-Pro-Gln-Val#Ile-Ala-GLy-Gln | 5.5 | 7.9 | <5.0 | <5.0 | 32 | <5.0 |
| Gly-Pro-Gln-His#Ile-Ala-Gly-Gln | 190 | 50 | 65 | 44 | 87 | ND |
| Gly-Pro-Hyp-Gly#Ile-Ala-Gly-Gln | 11 | 15 | 32 | 15 | 83 | 17 |
| Gly-Pro-Asp-Gly#Ile-Ala-Gly-Gln | 30 | 44 | 11 | 10 | 89 | 7.0 |
| Gly-Pro-Val-Gly#Ile-Ala-Gly-Gln | 32 | 30 | 130 | 110 | 160 | 57 |
| Gly-Pro-Leu-Gly#Ile-Ala-Gly-Gln | 150 | 260 | 330 | 290 | 190 | 420 |
| Gly-Pto-Arg-Gly#Ile-Ala-Gly-Gln | 17 | 32 | 160 | 83 | 99 | 13 |
| Gly-Pto-Met-Gly#Ile-Ala-Gly-Gln | 160 | 160 | 120 | 180 | 120 | 400 |
| Gly-Pro-Tyr-Gly#Ile-Ala-Gly-Gln | 200 | 110 | 200 | 150 | 230 | 240 |
| Gly-Asn-Gln-Gly#Ile-Ala-Gly-Gln | 17 | 45 | 60 | <5.0 | 68 | 25 |
| Gly-Ala-Gln-Gly#Ile-Ala-Gly-Gln | 50 | 23 | 22 | 9.4 | 62 | ND |

*ND: Not determined

In another embodiment, the wound-specific protease of the invention is human neutrophil elastase (HNE) (UNIPROT accession Nos. P08246 [human] and Q3UP87 [mouse]) is a serine proteinase in the same family as chymotrypsin and has broad substrate specificity. Secreted by neutrophils and macrophages during inflammation, it destroys bacteria and host tissue. In one embodiment, the substrate for detecting HNE has a core sequence Alanine-Alanine-Proline-Valine (AAPV). In another embodiment, the substrate for HNE is Ala-Pro-Glu-Glu-Ile/Met-Arg-Arg-Gln (APEEI/MRRQ) (Kasperkiewicz et al., *PNAS USA*, 111(7): 2518-2523, 2014; Korkmaz et al., *Methods Mol Biol.*, 844:125-138, 2012).

In some embodiments, human neutrophil elastase activity levels of about 5 U/mL to about 30 U/mL, including all values in between, e.g., about 6 U/mL, about 7 U/mL, about 8 U/mL, about 9 U/mL, about 10 U/mL, about 11 U/mL, about 12 U/mL, about 13 U/mL, about 14 U/mL, about 15 U/mL, about 16 U/mL, about 17 U/mL, about 18 U/mL, about 19 U/mL, about 20 U/mL, about 21 U/mL, about 22 U/mL, about 23 U/mL, about 24 U/mL, about 25 U/mL, or more, indicate chronic wound infection. In some embodiments, human neutrophil elastase activity levels of at least 9.6 indicate chronic wound infection. In some embodiments, human neutrophil elastase activity levels of at least 22.9 U/mL indicate chronic wound infection.

The MMP and the HNE subgroups have different mechanisms when interacting with the proteins in a wound and therefore as one would expect, each has a different method of inhibition of wound healing.

In another embodiment, the wound-specific enzyme is lysozyme. Lysozyme (UNIPROT accession Nos. P61626 [human] and P08905 [mouse]) is a glycoside hydrolase and its main function is to destroy the cell walls of bacteria. It hydrolyses the (1→4)-β-linkages between N-acetylmuramic acid and N-acetyl-D-glucosamine residues in peptidoglycan and also between N-acetyl-D glucosamine residues in chitodextrin. The natural substrate for lysozyme is the peptidoglycan layer of bacterial cell walls. However, a variety of low molecular mass substrates including murein degradation products as well as synthetic compounds have been used for various photometric, isotopic, and immunological lysozyme assays. Höltje et al., *EXS*, 75: 105-10, 1996. The following low molecular mass lysozyme substrates are available from Sigma Aldrich, Saint Louis, MO: 4-Methylumbelliferyl β-D-N,N',N''-triacetyl-chitotrioside (Sigma Catalog Number M5639) and 4-Nitrophenyl β-D-N,N',N''-triacetyl-chitotrioside (Sigma Catalog Number N8638).

In some embodiments, lysozyme activity levels of about 1000 U/mL to about 10000 U/mL, including all values in between, e.g., about 1100 U/mL, about 1200 U/mL, about 1300 U/mL, about 1400 U/mL, about 1500 U/mL, about 1600 U/mL, about 1700 U/mL, about 1800 U/mL, about 1900 U/mL, about 2000 U/mL, about 2100 U/mL, about 2200 U/mL, about 2300 U/mL, about 2400 U/mL, about 2500 U/mL, about 2600 U/mL, about 2700 U/mL, about 2800 U/mL, about 2900 U/mL, about 3000 U/mL, about 3250 U/mL, about 3500 U/mL, about 3750 U/mL, about 4000 U/mL, about 4250 U/mL, about 4500 U/mL, about 4750 U/mL, about 5000 U/mL, about 5250 U/mL, about 5500 U/mL, about 5750 U/mL, about 6000 U/mL, or more, indicate chronic wound infection. In some embodiments, lysozyme activity levels of at least 4800 U/mL indicate chronic wound infection.

Still in a further embodiment, the wound-specific enzyme is peroxidase, more specifically, a myeloperoxidase (MPO). MPO (UNIPROT accession Nos. P05164 [human] and P11247 [mouse]) is a peroxidase found in neutrophil granulocytes. In the presence of hydrogen peroxide ($H_2O_2$) and a halide (most commonly chloride) it produces the antimicrobial substances hypochlorite, singlet oxygen (1O2), chlorine (C12) and hydroxyl radicals (OH·). MPO can be detected using tetramethylbenzidine or 4-Benzoylamino-2,5-dimethoxyaniline. See, Andrews et al., *Anal Biochem*, 127(2): 346-50, 1982; Klebanoff et al., *J. Leukocyte Biol.*, 77, 598-625, 2005.

Still in a further embodiment, the wound-specific enzyme is cathepsin G (UNIPROT accession Nos. P08311 [human] and P28293 [mouse]), which is one of the three serine proteases of the chymotrypsin family that are stored in the azurophil granules. Cathepsin G-specific substrates have the sequence Ala-Ala-Pro-Phe or Ala-Ala-Pro-Met (Sigma Aldrich Catalog Nos. S7388 and M7771).

In some embodiments, cathepsin G activity levels of about 10 U/mL to about 100 U/mL, including all values in between, e.g., about 15 U/mL, about 20 U/mL, about 25 U/mL, about 30 U/mL, about 35 U/mL, about 40 U/mL, about 45 U/mL, about 50 U/mL, about 55 U/mL, about 60

U/mL, about 65 U/mL, about 70 U/mL, about 75 U/mL, about 80 U/mL, about 85 U/mL, about 90 U/mL, about 95 U/mL, about 100 U/mL, about 110 U/mL, about 120 U/mL, or more, indicate chronic wound infection. In some embodiments, cathepsin G activity levels of at least 50 U/mL, at least 40 U/mL, at least 30 U/mL, at least 20 U/mL, at least 15 U/mL or at least 10 U/mL indicates chronic wound infection.

In some embodiments, the wound-specific enzyme is urokinase-type plasminogen activator (UNIPROT accession Nos. P00749 [human] and P06869 [mouse]), which is a serine protease involved in degradation of the extracellular matrix and possibly tumor cell migration and proliferation. A substrate specific for urokinase has a basic motif Arg-Val or Lys-Val. See, Rijken et al., *Biochem Biophys Res Commun.*, 174(2):432-8, 1991.

In some embodiments, the one or more enzymes are esterases. An esterase is a hydrolase that splits esters into an acid and an alcohol in a chemical reaction with water. In one specific embodiment, the substrate for esterase is fluorescein diacetate-5-maleimide.

In some embodiments, the compositions comprise substrates that are capable of detecting a plurality of enzymes, e.g., at least 2, at least 3, at least 4, or more of the aforementioned enzymes. Such compositions may include, for example, a plurality of substrates conjugated to the same gel polymer or different gel polymers.

In certain embodiments, the substrates are labeled. The term "label," as used herein, refers to any substance attached to an epitope binding agent, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, streptavidin, protein A, protein G, antibodies or fragments thereof, polyhistidine, $Ni2^+$, Flag tags, myc tags, heavy metals, and enzymes (including alkaline phosphatase, peroxidase, and luciferase). Such methods are well-known in the art.

In certain embodiments, the substrates are labeled with label which is a detectable label. A detectable label is a moiety, the presence of which can be ascertained directly or indirectly. Generally, detection of the label involves the creation of a detectable signal such as for example an emission of energy. The label may be of a chemical, peptide or nucleic acid nature although it is not so limited. The nature of label used will depend on a variety of factors, including the nature of the analysis being conducted, the type of the energy source and detector used and the type of polymer, analyte, probe and primary and secondary analyte-specific binding partners. The label should be sterically and chemically compatible with the constituents to which it is bound.

The label can be detected directly for example by its ability to emit and/or absorb electromagnetic radiation of a particular wavelength. A label can be detected indirectly for example by its ability to bind, recruit and, in some cases, cleave another moiety which itself may emit or absorb light of a particular wavelength (e.g., an epitope tag such as the FLAG epitope, an enzyme tag such as horseradish peroxidase, etc.). Generally the detectable label can be selected from the group consisting of directly detectable labels such as a fluorescent molecule (e.g., fluorescein, rhodamine, tetramethylrhodamine, R-phycoerythrin, Cy-3, Cy-5, Cy-7, Texas Red, Phar-Red, allophycocyanin (APC), fluorescein amine, eosin, dansyl, umbelliferone, 5-carboxyfluorescein (FAM), 2'7'-dimethoxy-4'5'-dichloro-6-carboxyfluorescein (JOE), 6 carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), 5-(2'-aminoethyl)aminonaphthalene-1-sulfonic acid (EDANS), 4-acetamido-4'-isothiocyanatostilbene-2, 2'disulfonic acid, acridine, acridine isothiocyanate, r-amino-N-β-vinylsulfonyl)phenylnaphthalimide-3,5, disulfonate (Lucifer Yellow VS), N-(4-anilino-1-naphthyl)maleimide, anthranilamide, Brilliant Yellow, coumarin, 7-amino-4-methylcoumarin, 7-amino-4-trifluoromethylcouluarin (Coumarin 151), cyanosine, 4', 6-diaminidino-2-phenylindole (DAPI), 5',5"-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 4-dimethylaminophenylazophenyl-4'-isothiocyanate (DABITC), eosin isothiocyanate, erythrosin B, erythrosin isothiocyanate, ethidium, 5-(4,6-dichlorotriazin-2-yl)aminofluorescein (DTAF), QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron® Brilliant Red 3B-A), lissamine rhodamine B sulfonyl chloride, rhodamine B, rhodamine 123, rhodamine X, sulforhodamine B, sulforhodamine 101, sulfonyl chloride derivative of sulforhodamine 101, tetramethyl rhodamine, riboflavin, rosolic acid, and terbium chelate derivatives), a chemiluminescent molecule, a bioluminescent molecule, a chromogenic molecule, a radioisotope (e.g., P32 or H3, 14C, 125I and 131I), an electron spin resonance molecule (such as for example nitroxyl radicals), an optical or electron density molecule, an electrical charge transducing or transferring molecule, an electromagnetic molecule such as a magnetic or paramagnetic bead or particle, a semiconductor nanocrystal or nanoparticle (such as quantum dots described for example in U.S. Pat. No. 6,207,392 and commercially available from Quantum Dot Corporation and Evident Technologies), a colloidal metal, a colloid gold nanocrystal, a nuclear magnetic resonance molecule, and the like.

The detectable label can also be selected from the group consisting of indirectly detectable labels such as an enzyme (e.g., alkaline phosphatase, horseradish peroxidase, p-galactosidase, glucoamylase, lysozyme, luciferases such as firefly luciferase and bacterial luciferase (U.S. Pat. No. 4,737,456); saccharide oxidases such as glucose oxidase, galactose oxidase, and glucose-6-phosphate dehydrogenase; heterocyclic oxidases such as uricase and xanthine oxidase coupled to an enzyme that uses hydrogen peroxide to oxidize a dye precursor such as HRP, lactoperoxidase, or microperoxidase), an enzyme substrate, an affinity molecule, a ligand, a receptor, a biotin molecule, an avidin molecule, a streptavidin molecule, an antigen (e.g., epitope tags such as the FLAG or HA epitope), a hapten (e.g., biotin, pyridoxal, digoxigenin fluorescein and dinitrophenol), an antibody, an antibody fragment, a microbead, etc. Antibody fragments include Fab, F(ab)2, Fd and antibody fragments which include a CDR3 region.

In some embodiments, the substrates are conjugated with donor and acceptor fluorophores, respectively, that form a FRET pair. FRET can be used, for example, in an array format in order to determine if a particular secondary antibody is bound regardless of the identity of the analyte to which it binds. Alternatively, the secondary binding partner may be labeled detectably without labeling of the primary binding partner. Labeling of the secondary binding partner is also useful for establishing the orientation of the nucleic acid attached thereto. FRET alone generally requires only one excitation source (and thus wavelength) and usually only one detector. The detector may be set to either the emission spectrum of the donor or acceptor fluorophore. It is set to the donor fluorophore emission spectrum if FRET is detected by quenching of donor fluorescence. Alternatively, it is set to the acceptor fluorophore emission spectrum if FRET is detected by acceptor fluorophore emission. In some embodiments, FRET emissions of both donor and acceptor fluorophores can be detected. In still other embodiments, the donor is excited with polarized light and polarization of both emission spectra is detected.

In one embodiment, the detectable label is compatible with FRET-based assays. FRET requires the use of a FRET fluorophore pair. FRET fluorophore pairs are two fluorophores that are capable of undergoing FRET to produce or eliminate a detectable signal when positioned in proximity to one another. Examples of donors include Alexa 488, Alexa 546, BODIPY 493, Oyster 556, Fluor (FAM), Cy3 and TMR (Tamra). Examples of acceptors include Cy5, Alexa 594, Alexa 647 and Oyster 656. Cy5 can work as a donor with Cy3, TMR or Alexa 546, as an example. FRET should be possible with any fluorophore pair having fluorescence maxima spaced at 50-100 nm from each other.

The substrate may be labeled in a sequence non-specific manner in addition to the barcode labeling discussed herein. For example, if the polymer is a nucleic acid such as DNA, then its backbone may be stained with a backbone label. Examples of backbone stains that label nucleic acids in a sequence non-specific manner include intercalating dyes such as phenanthridines and acridines (e.g., ethidium bromide, propidium iodide, hexidium iodide, dihydroethidium, ethidium homodimer-1 and -2, ethidium monoazide, and ACMA); minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes.

Still other examples of nucleic acid stains include the following dyes from Molecular Probes: cyanine dyes such as SYTOX BLUE, SYTOX GREEN, SYTOX ORANGE, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PICOGREEN, OLIGREEN, RIBOGREEN, SYBR GOLD, SYBR GREEN I, SYBR GREEN II, SYBR DX, SYTO-40, -41, -42, -43, -44, -45 (BLUE), SYTO-13, -16, -24, -21, -23, -12, -11, -20, -22, -15, -14, -25 (GREEN), SYTO-81, -80, -82, -83, -84, -85 (orange), SYTO-64, -17, -59, -61, -62, -60, -63 (red).

In some embodiments, the reporter molecule comprises a chromophore or a fluorophore. In further embodiments, the chromophore is an azo moiety, a nitro moiety, a triarylmethane moiety, a methine, anthraquinone, a polyene moiety, or phthalocyanine. In some embodiments, the reporter molecule is a dye. It is envisioned that the dye can be, but is not limited to, rhodamine, coumarin, cyanine, xanthene, polymethine, pyrene, dipyrromethene borondifluoride, naphthalimide, a phycobiliprotein, peridinium chlorophyll proteins, conjugates thereof, and combinations thereof. Non-limiting examples of dyes include, fluorescein, 6-FAM, rhodamine, Texas Red, California Red, iFluor594, tetramethylrhodamine, a carboxyrhodamine, carboxyrhodamine 6F, carboxyrhodol, carboxyrhodamine 110, Cascade Blue, Cascade Yellow, coumarin, Cy2®, Cy3®, Cy3.5®, Cy5®, Cy5.5®, Cy7®, Cy-Chrome, DyLight 350, DyLight 405, DyLight 488, DyLight 549, DyLight 594, DyLight 633, DyLight 649, DyLight 680, DyLight 750, DyLight 800, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and-6-)-carboxy-X-rhodamine), HEX, Lucifer Yellow, Marina Blue, Oregon Green 488, Oregon Green 500, Oregon Green 514, Alexa Fluor® 350, Alex Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br$_2$, BODIPY® 530/550, BODIPY® 558/568, BODIPY® 630/650, BODIPY® 650/665, BODIPY® R6G, BODIPY® TMR, BODIPY® TR, conjugates thereof, and combinations thereof. In some embodiments, the reporter molecule is dimethylaminoazobenzenesulfonic acid (dabsyl) or a dabsyl derivative. In some embodiments, the reporter molecule is fluorescein, a fluorescein derivative, or a fluorescein-containing compound.

In some embodiments, the reporter molecule is a lipid. In some embodiments, the lipid is a synthetic phospholipid derivative. In some embodiments, the synthetic phospholipid derivative is DDPC, DLPC, DMPC, DPPC, DSPC, DOPC, POPC, or DEPC. In some embodiments, the synthetic phospholipid derivative is DLPC, DMPC, or DPPC. In some embodiments, the synthetic phospholipid derivative is DLPC. In some embodiments, the synthetic phospholipid derivative is DMPC. In some embodiments, the synthetic phospholipid derivative is DPPC.

In some embodiments, the reporter molecule is comprised in a detectable fragment that gets cleaved from the wound dressing material upon contact with an enzyme. In some embodiments, the reporter molecule is not comprised in the fragment that gets cleaved from the wound dressing material upon contact with an enzyme. In some embodiments, the reporter molecule is visualized by the naked eye. In some embodiments, the reporter molecule is visualized under UV light. In some embodiments, the reporter molecule is visualized using a fluorescent lamp.

In some embodiments of a wound dressing material of Formula I, R optionally comprises a quencher fragment. In some embodiments, the quencher fragment prevents the reporter molecule from fluorescing. In some embodiments, the quencher fragment is a protecting group. In some embodiments, the quencher fragment is an acetate group.

Disclosed herein, in certain embodiments, are modified wound dressing materials containing a target sequence for one or more enzymes. In some embodiments, enzyme-catalyzed cleavage releases a detectable fragment. The detectable fragment may comprise a reporter molecule. Qualitative or quantitative measurement of the levels of detectable fragments enables a determination of the presence or absence of infection in the wound.

In some embodiments, the enzyme-catalyzed cleavage releases a non-detectable fragment. In some embodiments, enzyme interaction with the wound dressing material cleaves a quencher fragment, and allows for a reporter molecule bound to the wound dressing material to fluoresce. Qualitative or quantitative measurement of the fluorescence enables a determination of the presence or absence of infection in the wound.

Disclosed herein, in certain embodiments, are peptide-modified wound dressing materials containing a target sequence for one or more proteases. Protease-catalyzed cleavage releases a detectable peptide fragment. The detectable peptide fragment comprises a reporter molecule. Qualitative or quantitative measurement of the levels of detectable peptide fragments enables a determination of the presence or absence of elevated proteases in the wound.

In some embodiments, the enzyme-catalyzed cleavage releases a non-detectable fragment. In some embodiments, enzyme interaction with the wound dressing material cleaves a quencher fragment, and allows for a reporter molecule bound to the wound dressing material to fluoresce. Qualitative or quantitative measurement of the fluorescence enables a determination of the presence or absence of infection in the wound.

In some embodiments of a wound dressing material of Formula I, R comprises a quencher fragment. In some embodiments, the quencher fragment is preventing the reporter molecule from fluorescing. In some embodiments, the quencher fragment is a protecting group. In some embodiments, the quencher fragment is an acetate group. In some embodiments of a wound dressing material of Formula I, R comprises a chemical moiety that is nucleophilic reaction product. In some embodiments, R comprises a maleimide-thiol adduct. In some embodiments, R comprises a haloacetamide-thiol conjugation product. In some embodiments, R comprises a haloacetamide conjugation product.

In some embodiments, the wound dressing material has the structure of Formula Ia:

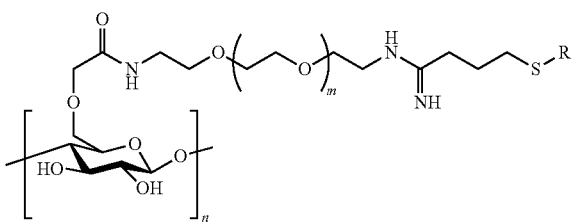

Formula Ia wherein R is a region comprising a reporter molecule; m is 1, 2, 3, 4, 5, 6, 7, 8, 9, 10, 11, 12, 13, 14, 15, 16, 17, 18, 19, 20, 25, 30, or more; and n is an integer selected from 200 to 4000, e.g., 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, including all unitary values in between, for example, 201, 202, 203, etc. In further embodiments, n is an integer selected from 300 to 3500. In still further embodiments, n is an integer selected from 400 to 3200. In some embodiments, R is a peptide region comprising a reporter molecule and at least one amino acid.

In some embodiments, the wound dressing material has the structure of Formula Ib:

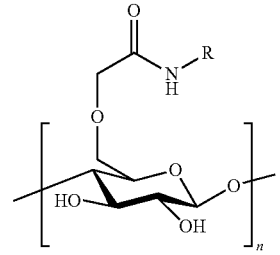

Formula Ib wherein R is a region comprising a reporter molecule; and n is an integer selected from 200 to 4000, e.g., 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, including all unitary values in between, for example, 201, 202, 203, etc. In further embodiments, n is an integer selected from 300 to 3500. In still further embodiments, n is an integer selected from 400 to 3200. In some embodiments, R is a peptide region comprising a reporter molecule and at least one amino acid. In some embodiments, R is a peptide region comprising a reporter molecule and one amino acid.

In some embodiments, the wound dressing material has the structure of Formula IIa:

$$M\text{-}L\text{-}PEP \qquad \text{Formula IIa}$$

wherein M is a gel-forming polymer selected from cellulose, chemically modified cellulose, pectin, alginate, chitosan, hyaluronic acid, polysaccharide, or gum-derived polymer, or any combination thereof; PEP is a peptide region comprising a reporter molecule and at least one amino acid; and L is a linker that connects M and PEP, wherein L comprises one or more polyethylene glycol subunits or polypropylene subunits.

In some embodiments, the wound dressing material has the structure of Formula IIb:

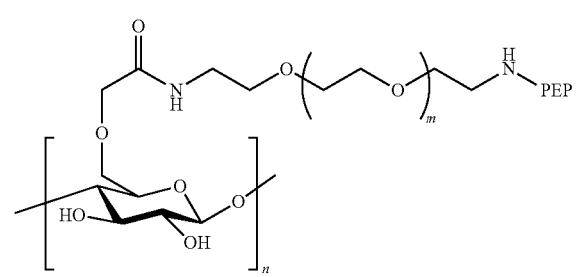

Formula IIb wherein PEP is a peptide region comprising a reporter molecule and at least one amino acid; m is 1, 2, 3, 4, 5, 6, 7, 8, 9, 10, 11, 12, 13, 14, 15, 16, 17, 18, 19, 20, 25, 30, or more; and n is an integer selected from 200 to 4000. In further embodiments, n is an integer selected from 300 to 3500. In still further embodiments, n is an integer selected from 400 to 3200.

In some embodiments, the wound dressing material has the structure of Formula IIc:

Formula IIc

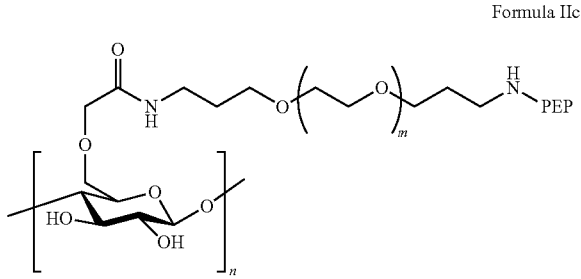

wherein PEP is a peptide region comprising a reporter molecule and at least one amino acid; m is 1, 2, 3, 4, 5, 6, 7, 8, 9, 10, 11, 12, 13, 14, 15, 16, 17, 18, 19, 20, 25, 30, or more; and n is an integer selected from 200 to 4000, e.g., 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, including all unitary values in between, for example, 201, 202, 203, etc. In further embodiments, n is an integer selected from 300 to 3500. In still further embodiments, n is an integer selected from 400 to 3200.

Compositions:

Embodiments described herein further relate to compositions containing the compounds of Formula I or Formula II. Such compositions may be prepared using conventional methods.

Once formulated, the resulting stock composition of compounds of Formula I or Formula II may be further modified into desired form, e.g., gels, balms, lotions, cream, paste, ointments, etc. using conventional methods, e.g., using carriers, gelling agents, emollients, surfactants, humectants, viscosity enhancers, emulsifiers, etc. See, e.g., WO 2011/126384 and WO 2013/004953, which are incorporated by reference.

Carriers for use in the composition may include, but are not limited to, water, glycerin, diglycerin, glycerin derivatives, glycols, glycol derivatives, sugars, ethoxylated and/or propoxylated esters and ethers, urea, sodium PCA, alcohols, ethanol, isopropyl alcohol, and combinations thereof. In one embodiment, the carrier is propylene glycol. Typically, the composition contains a carrier in an amount from about 1% by weight of the composition to about 99.9% by weight of the composition, more typically from about 2% by weight of the composition to about 95% by weight of the composition, and more typically from about 5% by weight of the composition to about 90% by weight of the composition.

Thermo-reversible gelling agents are defined as ingredients that are soluble, partially soluble, or miscible in a hydrophilic carrier at elevated temperatures, such as 50° C., wherein the agents have the ability to thicken the carrier when cooled to 25° C., but will be less viscous at 50° C. when application to a substrate is necessary. Suitable hydrophilic carriers include water, glycols, e.g., propylene glycol. Thermo-reversible gelling agents for use in the composition may include salts of fatty acids such as sodium stearate, sodium palmitate, potassium stearate. These salts can be added to the composition or can be created in-situ by addition of the fatty acid and neutralizing with appropriate base. An example of in-situ formation of the composition is to provide stearic acid and sodium hydroxide to produce sodium stearate. Other common hermos-reversible gelling agents could include, e.g., polyethylene glycols and derivatives such as PEG-20, PEG-150 distearate, PEG-150 pentaerythrityl tetrastearate, disteareth-75 IPDI, disteareth-100 IPDI, fatty alcohols, e.g., cetyl alcohol, fatty acids such as stearic acid, hydroxystearic acid and its derivatives, and combinations thereof.

In addition to the carrier and hermos-reversible gelling agent, the composition can contain various other ingredients and components. Examples of other ingredients that may be included within the composition are emollients, sterols or sterol derivatives, natural and synthetic fats or oils, viscosity enhancers, rheology modifiers, polyols, surfactants, alcohols, esters, silicones, clays, starch, cellulose, particulates, moisturizers, film formers, slip modifiers, surface modifiers, skin protectants, humectants, sunscreens, and the like.

Pharmaceutical Compositions and/or Preparations:

Embodiments described herein further relate to pharmaceutical compositions and/or preparations comprising one or more of the aforementioned compounds of Formula I or Formula II and a carrier. The phrase "pharmaceutically acceptable" is employed herein to refer to those compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, "pharmaceutically acceptable" means approved by a regulatory agency of the federal or a state government, or listed in the U.S. Pharmacopeia or other generally recognized pharmacopeia for use in mammals (e.g., animals), and more particularly, in humans.

The pharmaceutical compositions may be prepared by any suitable means known in the art. Examples of such compositions include those adapted for: (a) topical application, e.g., articles (e.g., gauzes, pads, swabs, dressings), creams, ointments, gels, lotions, etc.; (b) parenteral administration, e.g., subcutaneous, intramuscular or intravenous injection as a sterile solution or suspension; (c) oral administration, external application (e.g. drenches including aqueous and non-aqueous solutions or suspensions), tablets, boluses, powders, granules, pellets for admixture with feedstuffs, pastes for application to the tongue, etc.

In certain embodiments, the pharmaceutical compositions may comprise one or more antibiotic agents. As used herein, the term "antibiotic" or "antimicrobial agent" refers to a substance that inhibits the growth of or destroys microorganisms. Preferably, the antibiotic is useful in curbing the virulence of an infectious agent and/or treating an infectious disease. Antibiotic also refers to semi-synthetic substances wherein a natural form produced by a microorganism, e.g., yeast or fungus is structurally modified.

Preferably, the antibiotic is selected from the group consisting of β-lactams (including, β-lactamase inhibitors and cephalosporins), fluoroquinolones, aminoglycosides, tetracyclines and/or glycylcyclines and/or polymyxins. Any combination of antimicrobial agents may also be employed, e.g., at least one β-lactam and at least one fluoroquinolone; at least one aminoglycoside and one cephalosporin; at least one β-lactam and one β-lactamase inhibitor, optionally together with an aminoglycoside, etc.

As used herein, the term "β-lactam" inhibitor includes natural and semi-synthetic penicillins and penicillin derivatives, e.g., benzathine penicillin, benzylpenicillin (penicillin G), phenoxymethylpenicillin (penicillin V), procaine penicillin and oxacillin; methicillin, dicloxacillin and flucloxacillin; temocillin; amoxicillin and ampicillin; azlocillin, carbenicillin, ticarcillin, mezlocillin and piperacillin; biapenem, doripenem, ertapenem, imipenem, meropenem, panipenem and PZ-601; cephalexin, cephalothin, cefazolin, cefaclor, cefuroxime, cefamandole, cefotetan, cefoxitin, cefotaxime, and cefpodoxime; cefepime and cefpirome; cefadroxil, cefixime, cefprozil, cephalexin, cephalothin, cefuroxime, cefamandole, cefepime and cefpirome; cefoxitin, cefotetan, cefmetazole and flomoxef; tigemonam, nocardicin A and tabtoxin; clavulanic acid, moxalactam and flomoxef. Fluoroquinolones include, ciprofloxacin, garenoxacin, gatifloxacin, gemifloxacin, levofloxacin, and moxifloxacin. Aminoglycosides include, for e.g., kanamycin, amikacin, tobramycin, dibekacin, gentamicin, sisomicin, netilmicin, neomycin B, neomycin C, neomycin E (paromomycin) and streptomycin, including, synthetic derivatives clarithromycin and azithromycin. Tetracyclines include naturally-occurring compounds (e.g., tetracycline, chlortetracycline, oxytetracycline, demeclocycline) or semisynthetic agents (e.g., lymecycline, meclocycline, methacycline, minocycline, rolitetracycline). Glycylcyclines (e.g., minocycline/tigecycline) are derived from tetracyclines. Polymyxins include, e.g., polymyxin B and polymyxin E (colistin).

In certain embodiments, the compositions may contain an antibiotic at a concentration of 0.1 mg/mL, 0.5 mg/L, 1 mg/mL, 2 mg/mL, 3 mg/mL, 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL, 20 mg/mL, 21 mg/mL, 22 mg/mL, 23 mg/mL, 24 mg/mL, 25 mg/mL, 26 mg/mL, 27 mg/mL, 28 mg/mL, 29 mg/mL, 30 mg/mL, 31 mg/mL, 32 mg/mL, 33 mg/mL, 34 mg/mL, 35 mg/mL, 36 mg/mL, 37 mg/mL, 38 mg/mL, 39 mg/mL, 40 mg/mL, 41 mg/mL, 42 mg/mL, 43 mg/mL 44 mg/mL, 45 mg/mL, 50 mg/mL, 60 mg/mL, 70 mg/mL, 80 mg/m, 90 mg/mL, 100 mg/mL, 150 mg/mL, 200 mg/mL, 250 mg/mL, 300 mg/mL, 400 mg/mL, 500 mg/mL, or more. For example, imipenem and ertapenem may be used in the concentrations of 50, 30, 20, 15, 10, 5 and 1 mg/mL.

Wound Dressings:

Disclosed herein, in certain embodiments, are wound dressings comprising wound dressing materials as described herein, e.g., compounds of Formula I or Formula II. In some embodiments, the wound dressings consist essentially of the wound dressing materials as described herein, e.g., a compound of Formula I or Formula II.

In one embodiment, the wound dressing disclosed herein are biocompatible, biodegradable, non-immunogenic and readily commercially available.

In one embodiment, the compounds of Formula I or Formula II are provided in the form of particles, such as fiber particles or powder particles, optionally containing a medicament. In particular, the materials preferably contain CMC fibers.

The compositions may preferably comprise an intimate mixture of the dressing material and other compounds. For instance, in one embodiment, the intimate mixture comprises a mixed solution or dispersion of the dressing material and a suitable vehicle, such as a solvent, or a solid composition produced by removing solvent from such a solution or dispersion. Under this embodiment, the dressing material makes up at least 5%, more preferably at least 10%, 20%, 30%, 50%, 75%, 90% or greater % by weight of the material. In certain preferred embodiments, the material consists essentially of the dressing material.

Other components of the material may include β-25% by weight, for example from about 1 to about 20% by weight, of one or more other biocompatible polysaccharides, for example alginates such as sodium alginate or calcium alginate, starch derivatives such as sodium starch glycolate, cellulose derivatives such as methyl cellulose or carboxymethyl cellulose, or glycosaminoglycans such as hyaluronic acid or its salts, chondroitin sulfate or heparan sulfate. The materials may also comprise up to about 25% by weight, for example from about 1 to about 20% by weight, of one or more structural proteins selected from the group consisting of fibronectin, fibrin, laminin, elastin, collagen and mixtures thereof. Preferably the protein comprises collagen, and more preferably it consists essentially of collagen. The materials may also comprise up to about 20% by weight, preferably from about 2% to about 10% by weight of water. The materials may also contain β-40% by weight, for example from about 5 to about 25% by weight, of a plasticizer, preferably a polyhydric alcohol such as glycerol or sorbitol.

In certain embodiments, the materials may also comprise up to about 10% by weight, for example from about 0.01 to about 5% by weight, typically from about 0.1 to about 2% by weight of one or more therapeutic wound healing agents, such as non-steroidal anti-inflammatory drugs (e.g., acetaminophen), steroids, local anesthetics, antimicrobial agents, or growth factors (e.g., fibroblast growth factor or platelet derived growth factor). The antimicrobial agent may, for example, comprise an antiseptic, an antibiotic, or mixtures thereof. Preferred antibiotics include tetracycline, penicillins, terramycins, erythromycin, bacitracin, neomycin, polymycin B, mupirocin, clindamycin and mixtures thereof. Preferred antiseptics include silver, including colloidal silver, silver salts including salts of one or more of the anionic polymers making up the material, silver sulfadiazine, chlorhexidine, povidone iodine, triclosan, sucralfate, quaternary ammonium salts and mixtures thereof. These medicated wound dressing materials according to the invention provide sustained release of the therapeutic agents as the wound dressing material breaks down in use.

All of the above percentages are on a dry weight basis. Preferably, the weight ratio of the wound dressing material to other auxiliary agents and materials is from about 1:99 to about 99:1. More preferably, the weight ratio is in the range about 1:9 to about 9:1, more preferably it is in the range about 4:1 to about 1:4, still more preferably in the range about 2:1 to about 1:2.

The material may be in any convenient form, such as a powder, microspheres, flakes, a mat or a film.

In certain embodiments, the material is in the form of a semisolid or gel ointment for topical application.

In certain embodiments, the material is in the form of a freeze-dried or solvent-dried bioabsorbable sponge for application to a chronic wound. Preferably, the average pore size of the sponge is in the region of 10-500 μm, more preferably about 100-300 μm. A suitable sponge has been made by freeze-drying or solvent drying an aqueous dispersion comprising compounds of Formula I or Formula II, together with suitable therapeutic agents.

In yet other embodiments, the material is in the form of a flexible film, which may be continuous or interrupted (e.g. perforated). The flexible film preferably comprises a plasticizer to render it flexible, such as glycerol.

The ready availability of both gel forming polymers, e.g., cellulose derivatives, having a range of controllable properties means that the properties of the compositions the present invention can be controlled to an exceptional degree.

In particular, the rate of biological absorption, porosity and density of the materials can be controlled.

In one embodiment, provided herein are wound dressing materials in sheet form, comprising an active layer of a composition comprising compounds of Formula I or Formula II. The active layer would normally be the wound contacting layer in use, but in some embodiments it could be separated from the wound by a liquid-permeable top sheet. In one embodiment, the area of the active layer is from about 1 cm$^2$ to about 400 cm$^2$, particularly from about 4 cm$^2$ to about 100 cm$^2$.

In another embodiment, the wound dressing material further comprises a backing sheet extending over the active layer opposite to the wound facing side of the active layer. Preferably, the backing sheet is larger than the active layer such that a marginal region of width 1 mm to 50 mm, preferably 5 mm to 20 mm extends around the active layer to form a so-called island dressing. In such cases, the backing sheet is preferably coated with a pressure sensitive medical grade adhesive in at least its marginal region.

In embodiments wherein the dressing material comprises a backing sheet, the back sheet is substantially liquid-impermeable. In another embodiment, the backing sheet is semipermeable, e.g., the backing sheet is preferably permeable to water vapor, but not permeable to liquid water or wound exudate. Preferably, the backing sheet is also microorganism-impermeable. Suitable continuous conformable backing sheets will preferably have a moisture vapor transmission rate (MVTR) of the backing sheet alone of 300 to 5000 g/m$^2$/24 hrs., preferably 500 to 2000 g/m$^2$/24 hrs. at 37.5° C. at 100% to 10% relative humidity difference. The backing sheet thickness is preferably in the range of 10 to 1000 micrometers, more preferably 100 to 500 micrometers.

The MVTR of the dressing as a whole is lower than that of the backing sheet alone because the apertured sheet partially obstructs moisture transfer through the dressing.

Suitable polymers for forming the backing sheet include polyurethanes and poly alkoxyalkyl acrylates and methacrylates. Preferably, the backing sheet comprises a continuous layer of a high density blocked polyurethane foam that is predominantly closed-cell. A suitable backing sheet material is a polyurethane film.

In wound dressings comprising a backing layer comprising an adhesive, the adhesive layer should be moisture vapor transmitting and/or patterned to allow passage of water vapor. The adhesive layer is preferably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane. Polyurethane-based pressure sensitive adhesives may be selectively used.

In another embodiment, the dressing may comprise further layers of a multilayer absorbent article may be built up between the active layer and the protective sheet. For example, these layers may comprise an apertured plastic film to provide support for the active layer in use, in which case the apertures in the film are preferably aligned in register with the apertures in the hydrogel layer.

Still further, in other embodiments, the dressing may comprise an absorbent layer between the active layer and the protective sheet, especially if the dressing is for use on exuding wounds. The optional absorbent layer may be any of the layers conventionally used for absorbing wound fluids, serum or blood in the wound healing art, including gauzes, nonwoven fabrics, superabsorbents, hydrogels and mixtures thereof. Preferably, the absorbent layer comprises a layer of absorbent foam, such as an open celled hydrophilic polyurethane foam. In other embodiments, the absorbent layer may be a nonwoven fibrous web, for example a carded web of viscose staple fibers.

In certain embodiments, the wound dressing may be protected by a removable cover sheet. The cover sheet is normally formed from flexible thermoplastic material. Suitable materials include polyesters and polyolefins. Preferably, the adhesive-facing surface of the cover sheet is a release surface. That is to say, a surface that is only weakly adherent to the active layer and the adhesive on the backing sheet to assist peeling of the hydrogel layer from the cover sheet. For example, the cover sheet may be formed from a non-adherent plastic such as a fluoropolymer, or it may be provided with a release coating such as a silicone or fluoropolymer release coating.

In one embodiment, the wound dressing is sterile and packaged in a microorganism-impermeable container.

Kits:

In certain embodiments, the disclosed technology provides kits comprising, in one or separate compartments, the compounds of Formula I or Formula II, optionally together with an excipient, carrier or oil. The kits may further comprise additional ingredients, e.g., gelling agents, emollients, surfactants, humectants, viscosity enhancers, emulsifiers, etc., in one or more compartments. The kits may optionally comprise instructions for formulating an article for diagnosing, detecting or treating wounds, e.g., chronic or infected wounds. The kits may also comprise instructions for using the components, either individually or together, in the treatment of wounds.

In a related embodiment, the disclosed technology provides kits comprising a package and at least one absorbent article (described above) comprising the aforementioned compositions. Alternately, the kits may comprise the individual components separately, optionally together with secondary information, useable in or with the package.

Other embodiments disclosed herein relate to the use of the composition for the preparation of a dressing for the treatment of a wound. Preferably, the wound is a chronic wound, for example a wound selected from the group consisting of venous ulcers, decubitis ulcers and diabetic ulcers.

Surfaces:

Embodiments of the disclosed technology further provide for surfaces comprising the aforementioned compounds of Formula I or Formula II, wherein the reporter or peptide is oriented to permit binding to a partner, e.g., an enzyme. Preferably, the surface is a surface of a solid support. Numerous and varied solid supports are known to those in the art. Useful solid supports include natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

In one embodiment, the support is a well of an array plate, e.g., a microarray. Methods for constructing such arrays are known in the art, e.g., Cao et al., *Appl Environ Microbiol.*, 77(23): 8219-8225, 2011. Each compound of Formula I or Formula II (or the reporter alone) may be spotted in triplicate to eliminate irregular data due to physical defects in the array.

Systems:

Embodiments of the disclosed technology further provide for diagnostic systems comprising the aforementioned compositions and/or kits.

The various components of the diagnostic systems may be provided in a variety of forms. For example, the compounds of Formula I or Formula II (e.g., compounds containing peptide reporters) may be provided as a lyophilized reagent. These lyophilized reagents may be pre-mixed before lyophilization so that when reconstituted they form a complete mixture with the proper ratio of each of the components ready for use in the assay. In addition, the diagnostic systems of the present invention may contain a reconstitution reagent for reconstituting the lyophilized reagents of the kit.

Embodiments described herein further relate to LC detection systems. An LC detection system utilizes monitoring of a change in alignment of 5CB liquid crystals (LCs) as the detection method. In order to make this LC detection system fit to a CMC structure, a lipid is added to the part of the peptide sequence that would be cleaved. The lipid, once released would cause an alignment change in 5CB. The alignment of 5CB can be detected through crossed polarizing lenses and shows a change from dark to bright; the system would comprise containment of the LC at the correct alignment until the point of use and may also involve the use of crossed polarized lenses and a microscope for detection and/or visualization.

In some embodiments, the wound dressing comprises a wound dressing material having the structure of Formula Ia:

Formula Ia 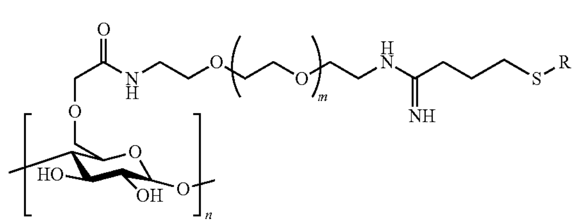 wherein R is a region comprising a reporter molecule; m is 1, 2, 3, 4, 5, 6, 7, 8, 9, or 10; and n is an integer selected from 200 to 4000. In further embodiments, n is an integer selected from 300 to 3500. In still further embodiments, n is an integer selected from 400 to 3200. In some embodiments, R is a peptide region comprising a reporter molecule and at least one amino acid.

In some embodiments, the wound dressing comprises a wound dressing material having the structure of Formula Ib:

Formula Ib 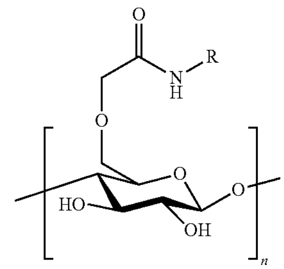 wherein R is a region comprising a reporter molecule; and n is an integer selected from 200 to 4000. In further embodiments, n is an integer selected from 300 to 3500. In still further embodiments, n is an integer selected from 400 to 3200. In some embodiments, R is a peptide region comprising a reporter molecule and at least one amino acid. In some embodiments, R is a peptide region comprising a reporter molecule and one amino acid.

In another aspect, provided herein are wound dressings comprising a wound dressing material having the structure of Formula II:

*M-L*-PEP Formula II wherein M is a gel-forming polymer; PEP is a peptide region comprising a reporter molecule and at least one amino acid; and L is a linker that connects M and PEP.

In some embodiments, the wound dressing comprises a wound dressing material having the structure of Formula IIa:

*M-L*-PEP Formula IIa wherein M is a gel-forming polymer selected from cellulose, chemically modified cellulose, pectin, alginate, chitosan, modified chitosan, hyaluronic acid, polysaccharide, or gum-derived polymer, CES, oxidized cellulose (or a derivative thereof), or any combination thereof; PEP is a peptide region comprising a reporter molecule and at least one amino acid; and L is a linker that connects M and PEP, wherein L comprises one or more polyethylene glycol subunits or polypropylene subunits.

In some embodiments, the wound dressing comprises a wound dressing material having the structure of Formula IIb:

Formula IIb 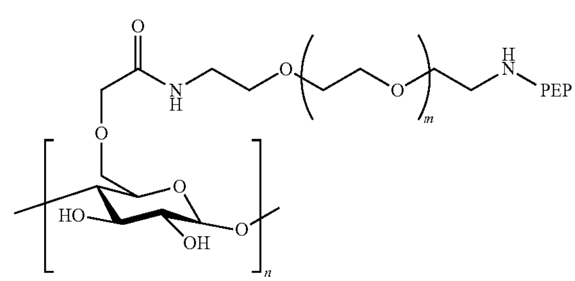 wherein PEP is a peptide region comprising a reporter molecule and at least one amino acid; m is 1, 2, 3, 4, 5, 6, 7, 8, 9, or 10; and n is an integer selected from 200 to 4000.

In further embodiments, n is an integer selected from 300 to 3500. In still further embodiments, n is an integer selected from 400 to 3200.

In some embodiments, the wound dressing comprises a wound dressing material having the structure of Formula IIc:

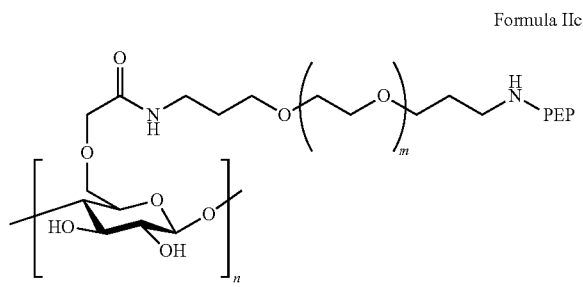

Formula IIc wherein PEP is a peptide region comprising a reporter molecule and at least one amino acid; m is 1, 2, 3, 4, 5, 6, 7, 8, 9, or 10; and n is an integer selected from 200 to 4000. In further embodiments, n is an integer selected from 300 to 3500. In still further embodiments, n is an integer selected from 400 to 3200.

Methods of Making Compounds of Formula I or Formula II:

Embodiments provided herein further relate to methods of making compounds of Formula I or Formula II, including precursors thereof. The term "precursor" includes any compound which is employed as a reactant to generate an intermediary or a final product.

In one embodiment, provided herein is a method of making a compound of Formula I comprising the structure M-R, wherein, M is a gel-forming polymer comprising a plurality of monomers selected from the group consisting of cellulose, carboxymethylcellulose (CMC), oxidized cellulose (or a derivative thereof), cellulose ethyl sulfonate (CES), pectin, alginate, chitosan, modified chitosan, hyaluronic acid, polysaccharide, or gum-derived polymer, or any combination or mixture thereof and R is a reporter region, comprising, conjugating the gel-forming polymer with the reporter molecule, e.g., via covalent bond. In one embodiment, the reporter R is a substrate for a wound-specific marker, e.g., a wound-specific enzyme such as a hydrolase, and more specifically a protease, as described before. Under this embodiment, the substrate for the wound-specific marker comprises, for example, a hydrolysable substrate, e.g., an amino acid, a sugar, a peptide, a polysaccharide, a nucleic acid, a lipid, or a combination thereof.

In one embodiment, the gel-forming polymer is conjugated to the reporter molecule via a peptide, a glycosidic, an amide, an ester, an ether, an anhydride or a similar linkage. As used herein, a "peptide bond" is formed by the condensation reaction between two amino acids, wherein the acid moiety of one reacts with the amino moiety of the other to produce a peptide bond (—CO—NH—) between the two amino acids. As used herein, a "glycosidic bond" is formed between the hemiacetal or hemiketal group of a saccharide (or a molecule derived from a saccharide) and the hydroxyl group of some compound such as an alcohol. A substance containing a glycosidic bond is a glycoside. The term 'glycoside' is now extended to also cover compounds with bonds formed between hemiacetal (or hemiketal) groups of sugars and several chemical groups other than hydroxyls, such as —SR (thioglycosides), —SeR (selenoglycosides), —NR1R2 (N-glycosides), or even —CR1R2R3 (C-glycosides). The term "amide" as used herein refers to refers to either —N($R^1$)—C(=O)— or —C(=O)—N($R^1$)— wherein R1 is defined herein to include hydrogen as well as other groups. The term "substituted amide" refers to the situation where R1 is not hydrogen, while the term "unsubstituted amide" refers to the situation where R1 is hydrogen. The term "ester" refers to a chemical compound derived from an acid (organic or inorganic) in which at least one hydroxyl group is replaced by an alkoxy group. Esters have a generic formula —C(=O)—O$R^1$ or $R^1$—C(=O)—O— wherein $R^1$ is defined herein to include hydrogen as well as other groups. Representative types of "esters" include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. The term "sulfonyl" represents a group of the formula —SO2-alkyl or —SO2-aryl wherein "alkyl" includes saturated monovalent hydrocarbon radicals having straight, branched or cyclic moieties or combinations thereof and contains 1-20 carbon atoms, preferably 1-5 carbon atoms and "aryl" includes an organic radical derived from an aromatic hydrocarbon by removal of one hydrogen, such as phenyl or naphthyl, optionally substituted by 1 to 5 substituents independently selected from the group halogen, hydroxy, thiol, amino, nitro, cyano, acyl, acyloxy, sulfonyl, sulfinyl, alkylamino, carboxy, ester, ether, amido, sulfonic acid, sulfonamide, alkylthio, oxyester. The term "sulfinyl" represents a group of the formula —SO-alkyl or —SO-aryl wherein "alkyl" and "aryl" are defined above. The term "sulfonamide" represents a group of formula —SO2NH2. The term "oxyester" means a group of formula —O—COO-alkyl, or —O—COO-aryl wherein "alkyl" and "aryl" are defined above. The term "ether" means a group of formula alkyl-O-alkyl or alkyl-O-aryl or aryl-O-aryl wherein "alkyl" and "aryl" are defined above. The term "amido" means a group of formula —CONRR' wherein R and R' are independently selected from hydrogen, "alkyl" or "aryl". The term "oxyamido" means a group of formula —O—CONRR' wherein R and R' are independently selected from hydrogen, "alkyl" or "aryl". The term "alkoxy", as used herein includes —O-alkyl groups wherein "alkyl" is defined above. The term "alkylthio" as used herein, includes alkyl groups wherein "alkyl" is defined above. The term "alkylamino" as used herein, includes —NHalkyl or —N(alkyl)$_2$ groups wherein "alkyl" is defined above.

Methods for conjugating reactive moieties to generate glycosidic, peptide, ester, oxyester, amide, amido, oxyamido, ether, sulfonyl, sulfinyl, sulfonamide, or other linkages such as alkoxy, alkylthio, alkylamino, etc. are known in the art and are further described in the examples.

In another embodiment, provided herein is a method of making a compound of Formula I comprising the structure M-L-R, wherein M and R are each, as described previously and L is a linker which is a monomer or a polymer of a neutral polymer, e.g., a polymer selected from the group consisting of an ethoxylated polyhydric alcohol, a polyvinyl pyrrolidone polymer, a polypropylene, a polyalkylene glycol, a polyamine, including, ethers, amides, and esters thereof.

In one embodiment, the M is conjugated to the L via a first ester, oxyester, amide, amido, oxyamido, ether, sulfonyl, sulfinyl, sulfonamide, alkoxy, alkylthio, alkylamino, or a similar linkage. Likewise, under this embodiment the linker L is conjugated to the reporter region R via a second ester, oxyester, amide, amido, oxyamido, ether, sulfonyl, sulfinyl, sulfonamide, alkoxy, alkylthio, alkylamino, or a similar linkage. The two linkages may be identical or different, e.g., M may be conjugated to the L via an ester linkage while L may be conjugated to the R via a peptide linkage.

In one embodiment, the compound of Formula I having the structure M-L-R is synthesized by first conjugating the gel-forming polymer M with the linker L to generate a precursor M-L and then conjugating the precursor M-L with the reporter region R to generate the compound of Formula I.

Alternately, the compound of Formula I having the structure M-L-R is synthesized by first conjugating the linker L with the reporter region R to generate the precursor L-R, which is then conjugated to the gel-forming polymer M to generate the compound of Formula I.

Still further, the compound of Formula I having the structure M-L-R may be synthesized in a single reaction chamber or multiple reaction chambers.

A representative retrosynthetic overview of potential reaction schemes employed in the synthesis of a compound of Formula I is presented below:

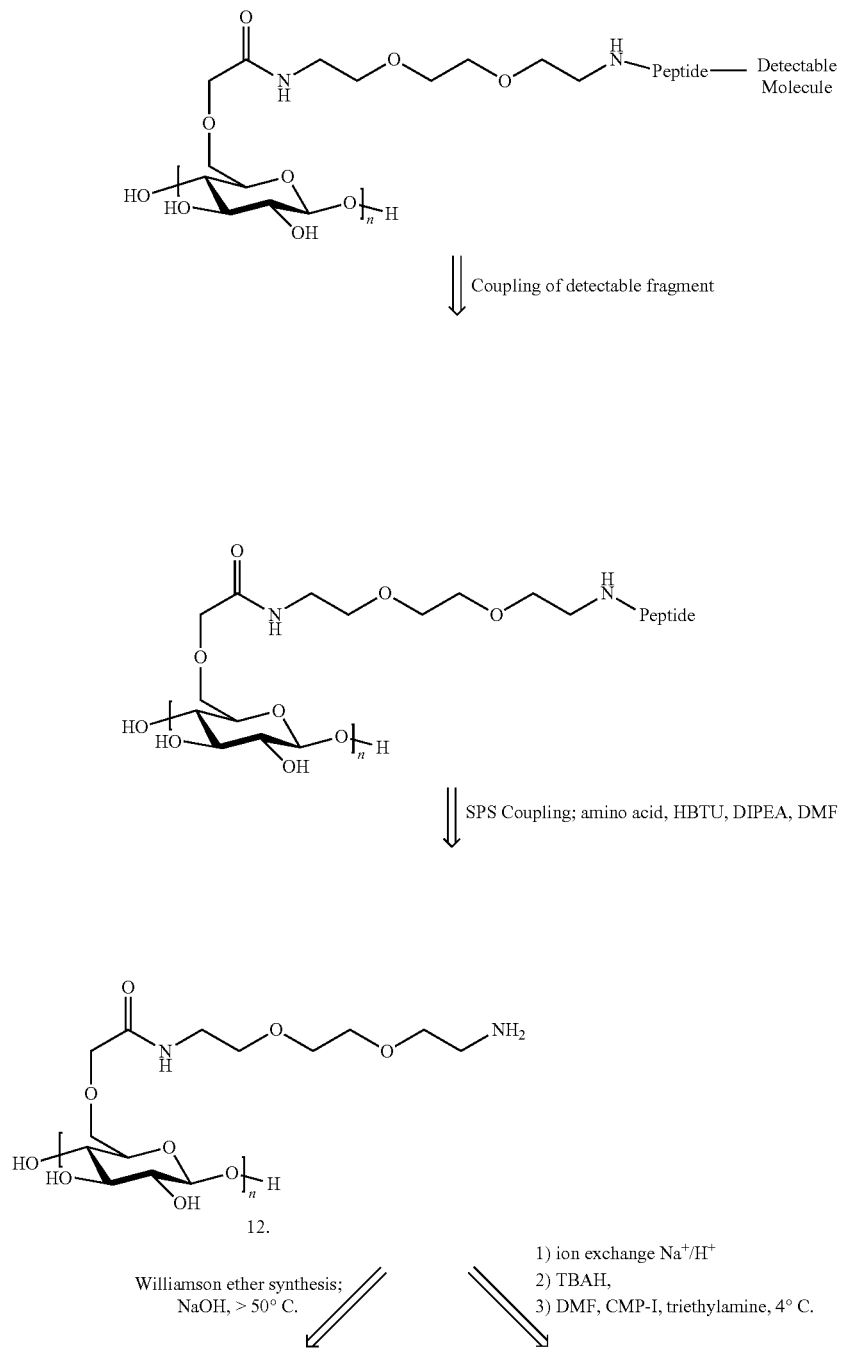

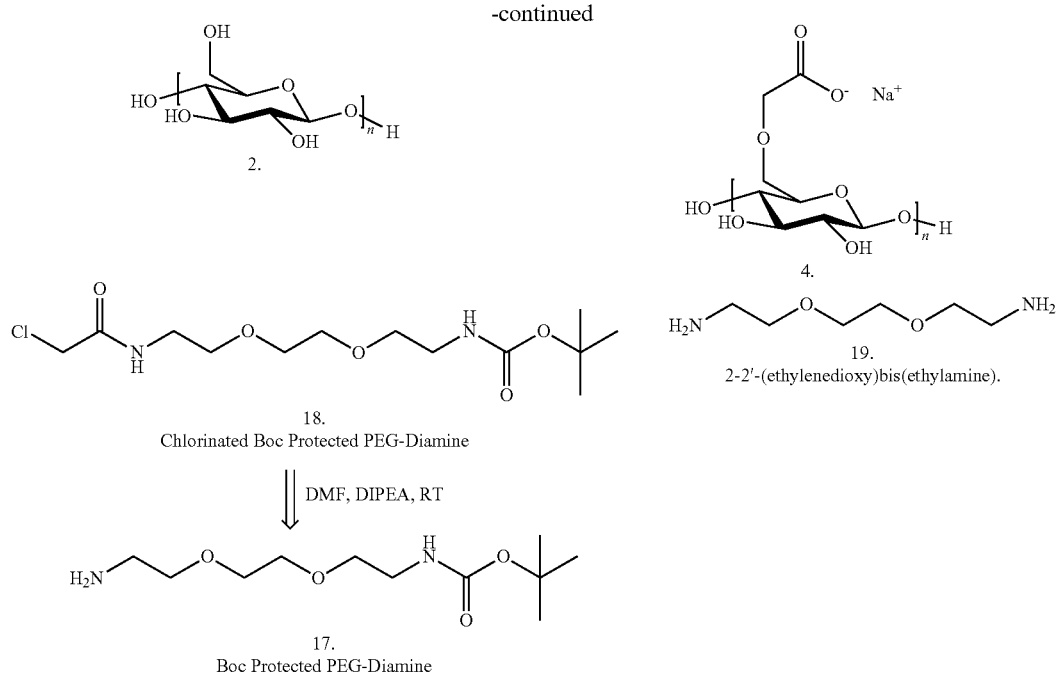

Diagnostic and Therapeutic Methods:

In one embodiment, the compositions, dressing materials, articles, kits and systems described herein are useful in diagnosing or treating wounds, particularly chronic or infected wounds. Although any type of wound may be diagnosed and/or treated, the embodiments are particularly suitable for diagnosing and treating wounds that exude wound fluid. For example, the wound may be a chronic or acute wound. Representative examples of chronic wounds include, e.g., venous ulcers, pressure sores, decubitis ulcers, diabetic ulcers and chronic ulcers of unknown aetiology. Representative examples of acute wounds include, e.g., acute traumatic laceration, perhaps resulting from an intentional operative incision.

As used herein, the term "a wound fluid" refers to any wound exudate or other fluid (suitably substantially not including blood) that is present at the surface of the wound, or that is removed from the wound surface by aspiration, absorption or washing. The determining, measuring or quantifying is suitably carried out on wound fluid that has been removed from the body of the patient, but can also be performed on wound fluid in situ. The term "wound fluid" does not normally refer to blood or tissue plasma remote from the wound site. The wound fluid is mammalian wound fluid, suitably human wound fluid.

In one embodiment, the diagnostic method comprises contacting a wound with at least one composition comprising a compound of Formula I or Formula II, a dressing material comprising such compounds, article comprising such materials or compounds, kits comprising such materials or compounds, or a system comprising such materials or compounds described herein; and measuring a parameter associated with the wound. In a specific embodiment, the parameter being measured is a level or activity of a wound-specific hydrolase. Particularly, the parameter being measured is the activity of the hydrolase.

In the aforementioned embodiments, the measurement may either be made in situ or ex situ. As used herein, the term "in situ" refers to processes, events, objects, or components that are present or take place within the context of the system or device, including, the surrounding environment, for example, the biological material with which the composition, article, system or device is in contact with. As an example, an in situ reaction may refer to the reaction of the various components present in the device (e.g., compound of Formula I or Formula II), including, components provided by the human skin tissue (e.g., wound exudate containing the enzyme). The term is contrasted with ex situ, which refers to outside of the environment.

In a second embodiment, the measurement is performed ex situ, e.g., removing the fluid from the wound for analysis in the apparatus or device of the invention.

Suitably, the measurement is made in situ.

In one diagnostic embodiment, the method comprising determining a level of a reporter, e.g., a product of a substrate acted upon by a wound-specific enzyme. More specifically, the method comprises determining a level of a hydrolase enzyme product. As used herein, the term "determining" includes measuring a numerical value of the activity or level of said hydrolase; establishing if the activity or level falls above or below a predetermined range; and/or comparing the numerical value of activity or level with a control standard. The control standard may comprise determining a level or activity of the hydrolase in a biopsy material obtained from an unwounded site or from a healthy subject.

In one specific embodiment, the term "determining" comprises measuring the parameter (e.g., activity or level) of at least one wound specific protease is selected from the group consisting of MMP-1 (collagenase), MMP-2 (gelatinase A), MMP-3 (stomelysin 1), MMP-8 (neutrophil collagenase), MMP-9 (gelatinase B), human neutrophil elastase (HNE), cathepsin G, urokinase-type plasminogen activator (uPA), and lysozyme, or a combination thereof; establishing if said parameter exceeds a first predetermined threshold; and/or comparing the numerical value of parameter with a control standard. The control standard may comprise determining a parameter of the protease in a biopsy material obtained from an unwounded site or from a healthy subject. In related embodiments, the term "determining" comprises establishing whether a weighted average (weighted sum) of the parameters associated with a plurality of the aforementioned proteases exceeds a predetermined threshold value for said weighted average.

In one particular embodiment, the parameter is activity level of the analyte (e.g. a protease) in a wound fluid. Typically, the activity of an individual analyte is expressed in terms units/mL.

In another embodiment, the parameter is the level of the analyte (e.g., protease) in a wound fluid. Typically, the term amount is also indicative of the activity of a particular analyte.

When used herein, the term "combined amount" or "combined activity" refers to a single numerical value that results from the application of a mathematical function to a plurality of values, for example those amounts obtained for a number of individual analytes. For example, the term "combined amount" or "combined activity" may refer to the sum or product of a group of individual values. Typically, the term "combined amount" or "combined activity" relates to the sum of a group of individual values. For example, in suitable embodiments, the amount of elastase refers to elastase-like activity (e.g., U/mL) and the amount of metalloproteinase (MMP) refers to total concentration of the respective analyte (e.g., in ng/mL).

When used herein, the term "quantifying" refers to measuring an absolute numerical quantity of a particular analyte(s) or substrate(s) in a sample, within the margins of experimental error.

The term "marker" or "analyte" refers to any chemical entity that is identified or determined using the apparatus, devices, kits or methods defined herein. The markers or analytes determined or identified by the apparatus, devices, kits or methods of the present invention are cleaved products of the aforementioned enzymes.

When used herein, the term "predetermined range" refers to a data range or profile that the skilled person would understand is indicative of a particular sub-class of patient. For instance, the predetermined range may be a data range or profile that is typical of a wound that would respond well to a particular wound treatment, such as antibiotic therapy. Alternatively, the predetermined range may suitably refer to a data range that is typical of a wound that would not respond well to a particular wound treatment, such as antibiotic therapy.

When used herein, the term "predetermined threshold" refers to a minimum level that the skilled person would determine is indicative of a non-healing wound based on statistical analysis of levels determined for known healing and non-healing wounds, for example as explained further above. For the test to be clinically useful, the threshold should be set at an appropriate level so that non-healing wounds with high protease activity are correctly identified. Increasing the threshold will increase the chance of only non-healing wounds being over the threshold. However, if the threshold is too high, wounds that are non-healing due to a high level of proteases would not be identified and clinically this would mean they would not receive the required protease modulating treatment.

When used herein, the term "control standard" or "control" refers to a data set or profile that can be used as a reference or comparison in order to define or normalize another data point or set of data. For instance, the term "control" or "control standard" may be data set or profile that is indicative of a particular sub-class of patient. Suitably, the control standard may be a data set or profile indicative of healing or non-healing wound status.

Suitably, in other aspects or embodiments of the present invention, the "control" or "control standard" can be a data set or profile that can be used as a comparative tool to allow a skilled person to determine whether a wound is likely to be responsive or non-responsive to a wound treatment, such as antibiotic therapy. In one embodiment, the control standard is a data set or profile indicative of a patient that does not respond well to wound treatment. Typically, the control standard is a data set or profile indicative of a patient that responds well to wound treatment. Patients that tend to respond well to wound treatment as disclosed herein exhibit lower combined amount or activity of hydrolases than patients that tend not to respond well to the treatment. For example, patients that tend to respond well to wound treatment as disclosed herein exhibit lower combined amounts of at least one wound-specific hydrolase.

In one embodiment, the threshold matrix metalloproteinase (MMP) activity is about 5 U/mL to about 30 U/mL, including all values in between, e.g., about 6 U/mL, about 7 U/mL, about 8 U/mL, about 9 U/mL, about 10 U/mL, about 11 U/mL, about 12 U/mL, about 13 U/mL, about 14 U/mL, about 15 U/mL, about 16 U/mL, about 17 U/mL, about 18 U/mL, about 19 U/mL, about 20 U/mL, about 21 U/mL, about 22 U/mL, about 23 U/mL, about 24 U/mL, about 25 U/mL, or more, indicate chronic wound infection. As is understood in the art, Units of activity (U) are typically used to describe enzyme catalytic activity, where a unit (U) refers to the amount of enzyme that catalyzes the conversion of 1 micromole (μmole) of substrate per minute. Thus, 1 enzyme unit (U)=1 μmol/min, where μmol refers to the amount of substrate converted.

In one embodiment, the threshold human neutrophil elastase activity is about 5 U/mL to about 30 U/mL, including all values in between, e.g., about 6 U/mL, about 7 U/mL, about 8 U/mL, about 9 U/mL, about 10 U/mL, about 11 U/mL, about 12 U/mL, about 13 U/mL, about 14 U/mL, about 15 U/mL, about 16 U/mL, about 17 U/mL, about 18 U/mL, about 19 U/mL, about 20 U/mL, about 21 U/mL, about 22 U/mL, about 23 U/mL, about 24 U/mL, about 25 U/mL, or more, indicate chronic wound infection.

In one specific embodiment, the threshold human neutrophil elastase activity levels of at least 9.6 indicate chronic wound infection. In some embodiments, human neutrophil elastase activity levels of at least 22.9 U/mL indicate chronic wound infection.

In one embodiment, the threshold lysozyme activity levels of about 1000 U/mL to about 10000 U/mL, including all values in between, e.g., about 1100 U/mL, about 1200 U/mL, about 1300 U/mL, about 1400 U/mL, about 1500 U/mL, about 1600 U/mL, about 1700 U/mL, about 1800 U/mL, about 1900 U/mL, about 2000 U/mL, about 2100 U/mL, about 2200 U/mL, about 2300 U/mL, about 2400 U/mL, about 2500 U/mL, about 2600 U/mL, about 2700 U/mL, about 2800 U/mL, about 2900 U/mL, about 3000 U/mL, about 3250 U/mL, about 3500 U/mL, about 3750 U/mL, about 4000 U/mL, about 4250 U/mL, about 4500 U/mL, about 4750 U/mL, about 5000 U/mL, about 5250 U/mL, about 5500 U/mL, about 5750 U/mL, about 6000 U/mL, or more, indicate chronic wound infection. In one specific embodiment, lysozyme activity levels of at least 4800 U/mL indicate chronic wound infection.

In one embodiment, the threshold cathepsin G activity levels of about 10 U/mL to about 100 U/mL, including all values in between, e.g., about 15 U/mL, about 20 U/mL, about 25 U/mL, about 30 U/mL, about 35 U/mL, about 40 U/mL, about 45 U/mL, about 50 U/mL, about 55 U/mL, about 60 U/mL, about 65 U/mL, about 70 U/mL, about 75 U/mL, about 80 U/mL, about 85 U/mL, about 90 U/mL, about 95 U/mL, about 100 U/mL, about 110 U/mL, about 120 U/mL, or more, indicate chronic wound infection. In some embodiments, cathepsin G activity levels of at least 50 U/mL, at least 40 U/mL, at least 30 U/mL, at least 20 U/mL, at least 15 U/mL or at least 10 U/mL indicates chronic wound infection.

Embodiments disclosed herein further relate to treatment of chronic or infected wounds using the compositions, materials, articles, dressings, kits and/or systems described herein. The therapeutic embodiment includes, contacting a composition, material, article, dressing, kit, system or devices of the invention with a subject in need thereof. Optionally, the method may include determination of whether the subject is responding to the treatment.

The skilled person would be able to easily identify whether wounds are "responsive to treatment" or not. In particular, the skilled person will readily be able to determine the levels of the proteases identified in the present claims that are predictive or indicative of a good response or poor response to wound treatment, particularly to treatment with wound dressings comprising oxidized cellulose. The terms "responsive" and "responder(s)" as used herein refer to wounds that are considered to respond well to wound treatment, particularly to treatment with a pharmacological agent, e.g., antibiotics. Similarly, "non-responsive" and "non-responder(s)" refers to wounds that are not considered to respond well to wound treatment, particularly to treatment with the pharmacological agent, e.g., antibiotics. For instance, patients who exhibit better than 50% wound closure after 4 weeks of wound treatment are considered to be responsive to said treatment.

In certain embodiments, a patient may be simultaneously diagnosed and treated with the compositions, articles, systems, or devices described herein. When used herein, the term "simultaneously" means performing the stated objectives, e.g., diagnosis and treatment, together.

In certain embodiments, a patient may be sequentially diagnosed and treated with the compositions, articles, systems, or devices described herein. When used herein, the term "sequentially" means the stated objectives, e.g., diagnosis and treatment, are temporally or spatially separated, e.g., diagnosis prior to treatment or diagnosis following treatment or a combination thereof, e.g., $1^{st}$ diagnosis→treatment→$2^{nd}$ diagnosis.

Embodiments described herein further enable a care giver or a patient to determine quickly and reliably whether a wound is likely to be non-healing, and to select an appropriate therapy based on this determination. For example, non-healing wounds may require the application of special wound dressings such as wound dressings comprising specific therapeutic agents, to promote healing. Accordingly, embodiments described herein further provide methods of treatment of a wound, e.g., chronic or infected wounds, comprising determining whether a wound is healing or non-healing, followed by applying a wound dressing comprising a therapeutic agent to the wound if it is non-healing.

Embodiments described herein provide methods and assays for diagnosis or detection of infected wounds. The methods are suitable for the detection of bacterial infectious agents. In one embodiment, the wounds are infected with gram-negative bacteria. Typical gram-negative bacteria include proteobacteria such as *E. coli, Salmonella, Pseudomonas*, and *Helicobacter*, and cyanobacteria. When classified in connection with medicine, they include *Pseudomonas aeruginosa* and Hemophilus *influenzae* causing the disturbance of the respiratory system, *Escherichia coli* and *Proteus mirabilis* causing the disturbance of the urinary system, and *Helicobacter pylori* and *Bacillus* Gaertner causing the disturbance of the alimentary system and micrococci such as *Neisseria meningitidis, Moraxella catarrhalis*, and *Neisseria* gonorrhea.

In another embodiment, the wounds are infected with gram-positive bacteria. By "gram-positive bacteria" is meant a bacterium or bacteria that contain(s) teichoic acid (e.g., lipoteichoic acid and/or wall teichoic acid), or a functionally equivalent glycopolymer (e.g., a rhamnopolysaccharide, teichuronic acid, arabinogalactan, lipomannan, and lipoarabinomannan) in its cell wall. Non-limiting examples of functionally equivalent glycopolymers are described in Weidenmaier et al., *Nature*, 6:276-287, 2008.

The bacteria include pathogenic bacteria that infect mammalian hosts (e.g., bovine, murine, equine, primate, feline, canine, and human hosts). Examples of such pathogenic bacteria include, e.g., members of a bacterial species such as *Bacteroides, Clostridium, Streptococcus, Staphylococcus, Pseudomonas, Haemophilus, Legionella, Mycobacterium, Escherichia, Salmonella, Shigella, Vibrio,* or *Listeria*. Some clinically relevant examples of pathogenic bacteria that cause disease in a human host include, but are not limited to, *Bacillus anthracis, Bacillus cereus, Bordetella pertussis, Borrelia burgdorferi, Brucella aborus, Brucella canis, Brucella melitensis, Brucella suis, Campylobacter jejuni, Chlamydia pneumoniae, Chlamydia psittaci, Chlamydia trachomatis, Clostridium botulinum, Clostridium difficile, Clostridium perfringens, Clostridium tetani, Corynebacterium diphtheriae, Enterococcus faecalis,* vancomycin-resistant *Enterococcus faecalis, Enterococcus faecium, Escherichia coli,* enterotoxigenic *Escherichia coli* (ETEC), enteropathogenic *Escherichia coli, E. coli* O157:H7, *Francisella tularensis, Haemophilus influenzae, Helicobacter pylori, Legionella pneumophila, Leptospira interrogans, Listeria monocytogenes, Mycobacterium leprae, Mycobacterium tuberculosis, Mycoplasma pneumoniae, Neisseria gonorrhoeae, Neisseria meningitidis, Proteus, Pseudomonas aeruginosa, Rickettsia rickettsia, Salmonella typhi, Salmonella typhimurium, Shigella sonnei, Staphylococcus aureus, Staphylococcus epidermis, Staphylococcus saprophyticus,* methicillin-resistant *Staphylococcus aureus* (MRSA), vancomycin-resistant *Staphylococcus aureus* (VSA), *Streptococcus agalactiae, Streptococcus pneumoniae, Streptococcus pyogenes, Treponema pallidum, Vibrio cholerae,* and *Yersinia pestis*.

In another embodiment, the infectious bacteria is selected from the group consisting of *Clostridium difficile*, Carbapenem-Resistant Enterobacteriaceae (CR-*Klebsiella* spp; CR-*E. coli*), and *Neisseria gonorrhoeae*. In another embodiment, the infectious bacteria is selected from the group consisting of multidrug-resistant *Acinetobacter*, drug-resistant *Campylobacter*, extended spectrum β-Lactamase (ESBL)-producing enterobacteriaceae, vancomycin-resistant *enterococcus*, multidrug-resistant *Pseudomonas aeruginosa*, drug-resistant non-typhoidal *Salmonella*, drug-resistant *Salmonella enterica* serovar *Typhi*, drug-resistant *Shigella*, methicillin-resistant *Staphylococcus aureus* (MRSA), drug-resistant *Streptococcus pneumoniae*, and drug-resistant Tuberculosis. In another embodiment, the infectious bacteria is selected from the group consisting of vancomycin-resistant *Staphylococcus aureus*, erythromycin-resistant Group A *Streptococcus*, clindamycin-Resistant Group B *Streptococcus*.

In certain embodiments, the chronic or infected wounds are found in host subjects. Preferably, the hosts are mammals, e.g., a rodent, a human, a livestock animal, a companion animal, or a non-domesticated or wild animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoo animal. As used herein, a "zoo animal" refers to an animal that may be found in a zoo. Such animals may include non-human primates, large cats, wolves, and bears. In an exemplary embodiment, the subject is a human.

In one aspect, provided herein are methods of detecting levels of one or more enzymes in a mammalian wound, the method comprising the steps of: (a) placing the wound dressing material described herein in contact with the mammalian wound; (b) visually comparing the wound dressing material in contact with the mammalian wound with one or more reference samples; and (c) obtaining a qualitative determination of the concentration of reporter molecules in the wound dressing material in contact with the mammalian wound.

In some embodiments, the method of detecting the level of one or more enzymes in a mammalian wound consists essentially of the steps of: (a) placing the wound dressing material described herein in contact with the mammalian wound; (b) visually comparing the wound dressing material in contact with the mammalian wound with one or more reference samples; and (c) obtaining a qualitative determination of the concentration of reporter molecules in the wound dressing material in contact with the mammalian wound.

In another aspect, provided herein are methods of detecting levels of one or more enzymes in a mammalian wound, the method comprising the steps of: (a) placing the wound dressing material described herein in contact with the mammalian wound; (b) obtaining a quantitative determination of the concentration of reporter molecules in the wound dressing material in contact with the mammalian wound; and (c) comparing the quantitative determination with one or more reference samples.

In some embodiments, the method of detecting the level of one or more enzymes in a mammalian wound consists essentially of the steps of: (a) placing the wound dressing material described herein in contact with the mammalian wound; (b) obtaining a quantitative determination of the concentration of reporter molecules in the wound dressing material in contact with the mammalian wound; and (c) comparing the quantitative determination with one or more reference samples.

In one aspect, provided herein are methods of detecting levels of one or more proteases in a mammalian wound, the method comprising the steps of: (a) placing the wound dressing material described herein in contact with the mammalian wound; (b) visually comparing the wound dressing material in contact with the mammalian wound with one or more reference samples; and (c) obtaining a qualitative determination of the concentration of reporter molecules in the wound dressing material in contact with the mammalian wound.

In some embodiments, the method of detecting the level of one or more proteases in a mammalian wound consists essentially of the steps of: (a) placing the wound dressing material described herein in contact with the mammalian wound; (b) visually comparing the wound dressing material in contact with the mammalian wound with one or more reference samples; and (c) obtaining a qualitative determination of the concentration of reporter molecules in the wound dressing material in contact with the mammalian wound.

In another aspect, provided herein are methods of detecting levels of one or more proteases in a mammalian wound, the method comprising the steps of: (a) placing the wound dressing material described herein in contact with the mammalian wound; (b) obtaining a quantitative determination of the concentration of reporter molecules in the wound dressing material in contact with the mammalian wound; and (c) comparing the quantitative determination with one or more reference samples.

In some embodiments, the method of detecting the level of one or more proteases in a mammalian wound consists essentially of the steps of: (a) placing the wound dressing material described herein in contact with the mammalian wound; (b) obtaining a quantitative determination of the concentration of reporter molecules in the wound dressing material in contact with the mammalian wound; and (c) comparing the quantitative determination with one or more reference samples.

In another aspect, provided herein are methods to diagnose a chronic wound in a mammal, the method comprising the steps of: (a) placing the wound dressing material described herein in contact with the mammalian wound; (b) visually comparing the wound dressing material in contact with the mammalian wound with one or more reference samples; and (c) obtaining a qualitative determination of the concentration of reporter molecules in the wound dressing material in contact with the mammalian wound.

In some embodiments, the method to diagnose a chronic wound in a mammal consists essentially of the steps of: (a) placing the wound dressing material described herein in contact with the mammalian wound; (b) visually comparing the wound dressing material in contact with the mammalian wound with one or more reference samples; and (c) obtaining a qualitative determination of the concentration of reporter molecules in the wound dressing material in contact with the mammalian wound.

In another aspect, provided herein are methods to diagnose a chronic wound in a mammal, the method comprising the steps of: (a) placing the wound dressing material described herein in contact with the mammalian wound; (b) obtaining a quantitative determination of the concentration of reporter molecules in the wound dressing material in contact with the mammalian wound; and (c) comparing the quantitative determination with one or more reference samples.

In some embodiments, the method to diagnose a chronic wound in a mammal consists essentially of the steps of: (a) placing the wound dressing material described herein in contact with the mammalian wound; (b) obtaining a quantitative determination of the concentration of reporter molecules in the wound dressing material in contact with the mammalian wound; and (c) comparing the quantitative determination with one or more reference samples.

In another aspect, provided herein are methods to treat a wound in a mammal, the method comprising the steps of: (a) placing the wound dressing material described herein in contact with the mammalian wound; (b) visually comparing the wound dressing material in contact with the mammalian wound with one or more reference samples; (c) obtaining a qualitative determination of the concentration of reporter molecules in the wound dressing material in contact with the mammalian wound; and (d) administering medical treatment to the mammal; wherein the medical treatment comprises antibiotic therapy only when the concentration of reporter molecules indicates that the mammalian wound is chronic.

In some embodiments, the method to treat a wound in a mammal consists essentially of the steps of: (a) placing the wound dressing material described herein in contact with the mammalian wound; (b) visually comparing the wound dressing material in contact with the mammalian wound with one or more reference samples; (c) obtaining a qualitative determination of the concentration of reporter molecules in the wound dressing material in contact with the mammalian wound; and (d) administering medical treatment to the mammal; wherein the medical treatment comprises antibiotic therapy only when the concentration of reporter molecules indicates that the mammalian wound is chronic.

In another aspect, provided herein are methods to treat a wound in a mammal, the method comprising the steps of: (a) placing the wound dressing material described herein in contact with the mammalian wound; (b) obtaining a quantitative determination of the concentration of reporter molecules in the wound dressing material in contact with the mammalian wound; (c) comparing the wound dressing material in contact with the mammalian wound with one or more reference samples; and (d) administering medical treatment to the mammal; wherein the medical treatment comprises antibiotic therapy only when the concentration of reporter molecules indicates that the mammalian wound is chronic.

In some embodiments, the method to treat a wound in a mammal consists essentially of the steps of: (a) placing the wound dressing material described herein in contact with the mammalian wound; (b) obtaining a quantitative determination of the concentration of reporter molecules in the wound dressing material in contact with the mammalian wound; (c) comparing the wound dressing material in contact with the mammalian wound with one or more reference samples; and (d) administering medical treatment to the mammal; wherein the medical treatment comprises antibiotic therapy only when the concentration of reporter molecules indicates that the mammalian wound is chronic.

Preferably, the diagnosis and treatment is conducted in situ. Embodiments described herein therefore allow diagnosis and treatment of wounds in an easy, non-invasive manner. For instance, the diagnosis may be made in real time and the treatment may be applied to the infected wound or to the patient (systemically) and the progress of wound treatment be monitored over real-time, e.g., dissipation of the signal generated by the reporter molecule due to wound-healing.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

List of Abbreviations

As used above, and throughout the description of the invention, the following abbreviations, unless otherwise indicated, shall be understood to have the following meanings:

ACN or MeCN acetonitrile
Bn benzyl
BOC or Boc tert-butyl carbamate
t-Bu tert-butyl
CMC carboxymethylcellulose
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMSO dimethylsulfoxide
equiv equivalent(s)
Et ethyl
EtOH ethanol
EtOAc ethyl acetate
Fmoc fluorenylmethyl carbamate
HBTU N,N,N',N'-tetramethyl-O-(1H-benzotriazol-1-yl) uronium hexafluorophosphate
HPLC high performance liquid chromatography
Me methyl
MeOH methanol
MS mass spectroscopy
NMR nuclear magnetic resonance
PBS phosphate buffered saline
RP-HPLC reverse phase-high pressure liquid chromatography
TFA trifluoroacetic acid
THF tetrahydrofuran For the polymers shown in the Examples below, n is an integer selected from 400 to 3200.

Example 1: Preparation of Polymer 1 (Using CMC Fiber)

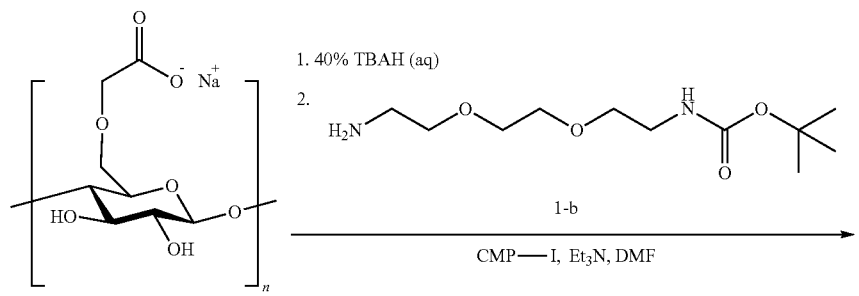

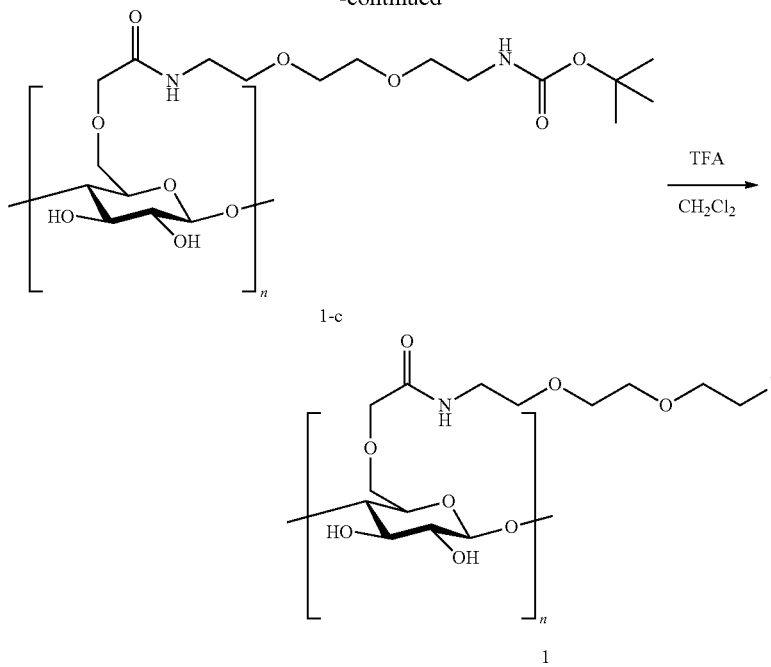

Sodium carboxymethylcellulose (NaCMC) fiber (443 mg, 1.08 mmol) was dissolved in deionized water (44 ml) to give a 1% solution. Dowex 650C monosphere ion exchange resin was added in order to provide the acidified CMC (CMC-H). The monospheres were removed by filtration and then tetrabutylammonium hydroxide (TBAH) 40% (aq) was added until the pH was 8-9. The resulting solution was stirred for 30 min before being lyophilized overnight. The lyophilized material (0.38 g) was dissolved in 40 ml dry DMF under nitrogen with stirring and gentle heating over a period of approximately 1 h. The resulting solution was cloudy and off-white. The solution was cooled to approximately 4° C. To this stirred solution, 2-chloro-N-methylpyridinium iodide (CMP-I) (0.33 g, 1.3 mmol) was added. Shortly after this, compound 1-b (0.5 g, 2 mmol) was also added along with 3 drops of dry DCM and a few drops of dry triethylamine. The reaction mixture was kept at 4° C. and stirred for 3 h, after which it became a darker almost brown color. 95% Acetone (aq) (80 ml) was added slowly and stirred for 20 min at 4° C. and then kept at 4° C. overnight. The resulting white precipitate was filtered out of the brown solution. The material was then washed with acetone five times by the following method: added 40 ml 99.5% acetone, mixed and sonicated for approximately 1 min, filtered off acetone and collected solid product. This produced a solid, off-white spongy material. The remaining acetone was removed under reduced pressure. The solid was washed in ethanol (20 ml×1) followed by acetone (20 ml×3). During each wash, the wash solution was sonicated for 1 min before filtration to collect the solid. The solid (compound 1-c) was placed on the high vacuum rotary evaporator for 45 min. Weight=0.288 g. FTIR: 3360, 3320 (N—H/O—H), 2875 (C—H), 1650 with shoulder (amidic C=O of BOC), 1590 (C=O of CMC).

In order to assess the solubility of compound 1-c, the following method was followed: Compound 1-c was weighed out into mass spectrometry vials (~0.0013 g per vial). Approximately 1 ml of the required solvent was added to the vial. The samples were assessed visually for solubility at the following time points: initially, after gently heating at 40° C. for 1 min, after sonication for 10 sec, and after being left at RT overnight. Data is shown below: x indicates insoluble material.

| Solvent | Initial | After heating | After sonication | Overnight |
|---|---|---|---|---|
| DCM | x | x | x | x |
| EtOH | x | x | x | x |
| MeOH | x | x | x | x |
| THF | x | x | x | x |
| DI water | x | solid dispersed | well dispersed, cloudy solution | well dispersed, cloudy solution |
| DMF | x | x | x | x |

Compound 1-c (0.05 g, 0.11089 mmol) was weighed and cut into the smallest possible pieces. 10% TFA in DCM was added (10 ml) and the mixture was stirred at RT for 1 h. Volatile solvent and reagent was removed using a high vacuum rotary evaporator. The remaining solid was subjected to an azeotrope three times in order to remove any remaining TFA by reducing its boiling point: toluene (10 ml×3) was added to the solid product and stirred before being removed using the high vacuum rotary evaporator to provide polymer 1 as an off-white solid. Weight=0.0524 g. FTIR: 3326 (N—H/O—H), 2891 (C—H), 1668 (C=O urethane stretch). Elemental analysis (TFA salt): Carbon: Expected ~43%; Actual=38.90%. Hydrogen: Expected ~5.8%; Actual=5.43%. Nitrogen: Expected-4.4%; Actual=0.28%. Degree of substitution is 0.28/4.38=0.06.

Solubility of Polymer 1 was determined in a similar manner as for compound 1-c. Data is shown below: x indicates insoluble material.

| Solvent | Initial | After heating | After sonication | Overnight |
|---|---|---|---|---|
| DCM | x | x | x | x |
| EtOH | x | x | x | x |
| MeOH | x | x | x | x |
| THF | x | x | x | x |
| DI water | x | x | x | x |
| DMF | x | x | x | x |

Qualitative determination of amination of Polymer 1 was assessed using the ninhydrin-based Kaiser test. Three reagents were prepared: (1) 500 mg (0.5 g) ninhydrin in 10 ml in EtOH; (2) 80 g phenol in 20 ml EtOH; and (3) 2 ml of 0.001 M KCN diluted to 100 mL with pyridine. A sample of Polymer 1 (10-20 mg) was placed in a round bottom flask. Three to five drops of each reagent was added to the flask. The flask was heated to 100° C. using an oil bath and a reflux condenser and stirred for 5 min. Any color change was observed visually. A dark blue/purple color was detected, indicating presence of amine.

Example 2: Preparation of Polymer 2

A solution of Fmoc-Phe-OH (0.0267 g, 0.069 mmol), HBTU (0.0262 g, 0.069 mmol), DIPEA (0.015 ml, 0.090 mmol) and dry DMF (0.82 ml) was prepared. A 15-ml plastic separating column was set up with a 10 m polyethylene frit and a luer tip was attached. Polymer 1 (0.034 g, 0.097 mmol) was added to the column followed by the amino acid solution. A lid was placed onto the column and was further sealed with parafilm. The column was placed on a blood rotor at RT overnight. The solution was drained using reduced pressure and the solid product was washed with EtOH to provide Polymer 2 as a white solid. Weight=0.0266 g. A Kaiser test was used to confirm absence of terminal amines. FTIR: 3324 (N—H/O—H), 3281 (O—H), 2898 (C—H), 1720 (aromatic C=O), 1666 (C=O urethane stretch), 1660, (C=O amide stretch of Fmoc).

Solubility of Polymer 2 was determined in a similar manner as for compound 1-c. Data is shown below: x indicates insoluble material.

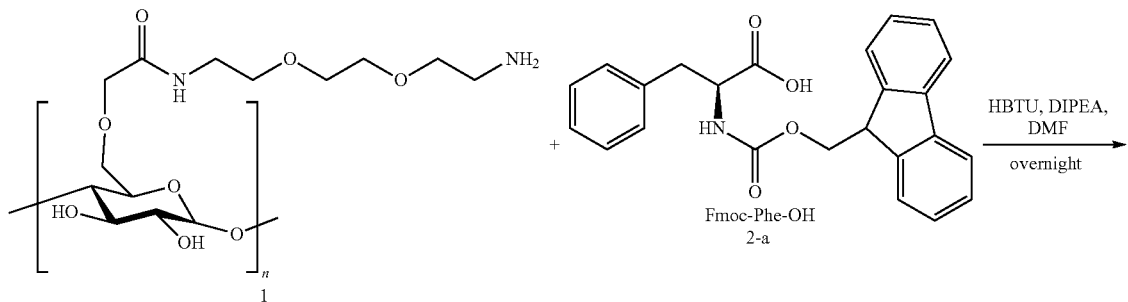

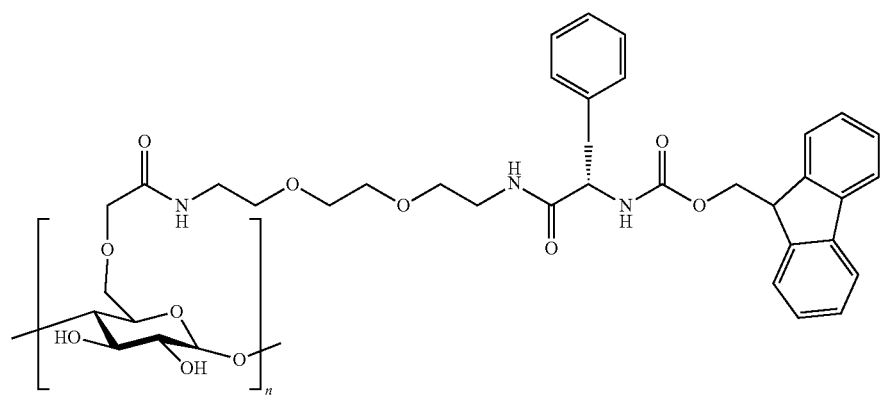

| Solvent | Initial | After heating | After sonication | Overnight |
|---------|---------|---------------|------------------|-----------|
| DCM     | x       | N/A           | N/A              | N/A       |
| EtOH    | x       | N/A           | N/A              | N/A       |
| DMF     | x       | N/A           | N/A              | N/A       |

Example 3: Preparation of Polymer 3

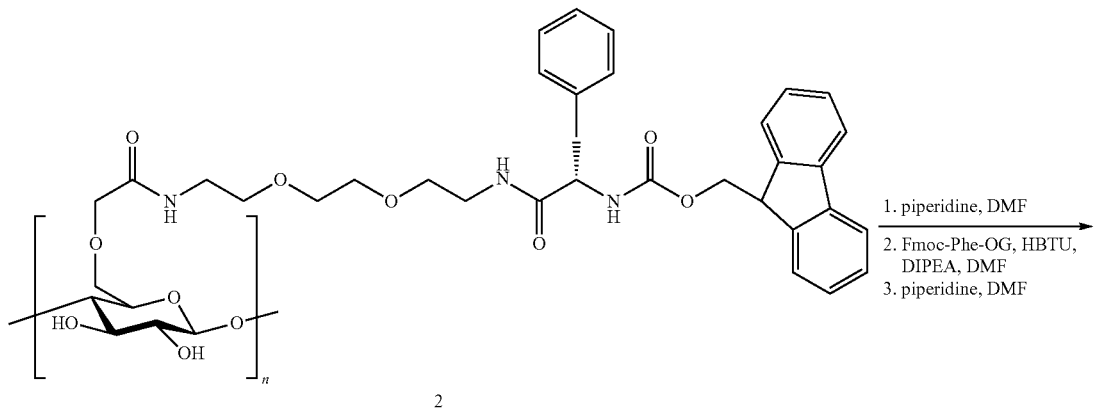

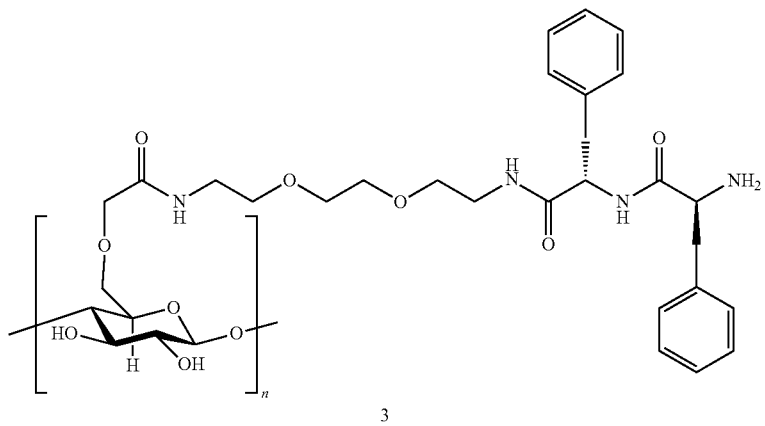

Polymer 2 was placed in a solution of piperidine: DMF (1:4 v/v, 6 ml) for approximately 2 h. The resulting de-protected product was then washed with EtOH before conducting a Kaiser test to confirm presence of free amine. This de-protected product (0.080 g, 0.15 mmol) was added to a 15-ml plastic separating column set up with a 10 μm polyethylene frit and a luer tip. A solution of Fmoc-Phe-OH (0.063 g, 0.16 mmol), HBTU (0.062 g, 0.16 mmol), DIPEA (0.23 ml, 1.8 mmol) and dry DMF (6 ml) was prepared and added to the column. A lid was placed onto the column and was further sealed with parafilm. The column was placed on a blood rotor at RT overnight. The solution was drained using reduced pressure and the solid product was washed with EtOH (10 ml×3) to provide the coupling product as a red solid. Weight=0.0691 g. A Kaiser test was used to confirm absence of terminal amines. The coupling product was washed with DCM. FTIR: 3315 (N—H/O—H), 2866 (C—H),1730 (aromatic C=O), 1651+shoulder (C=O, amide of F) and/or (C=O amide stretch of F-Fmoc), 1587 (C=O urethane stretch).

In order to remove the Fmoc group, the coupling product was placed in a solution of piperidine: DMF (1:4 v/v, 6 ml) for approximately 2 h. The resulting de-protected product was then washed with EtOH (10 ml×3) and DCM (10 ml) to provide Polymer 3 as a brittle red solid. Weight=0.0638 g, yield=62%. A Kaiser test was used to confirm presence of terminal amines. FTIR: 3315(N—H/O—H), 2866 (C—H), 1730 very small peak (aromatic C=O), 1651 no shoulder (C=O, amide of F), 1587 (C=O urethane stretch). [Note: FTIR suggests that a small amount of Fmoc remains on the final product].

Example 4: Preparation of Polymer 4

Synthesis of Intermediate 4-c

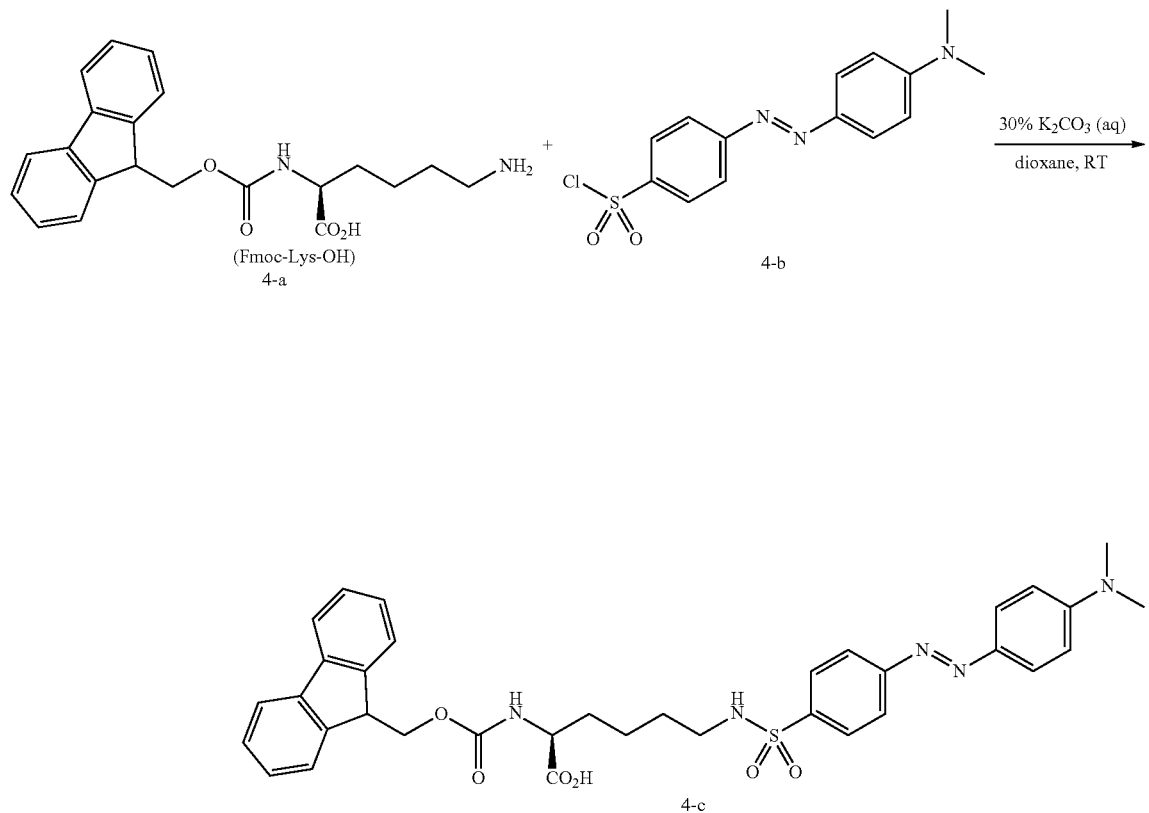

Fmoc-Lys-OH·HCl (0.0405 g, 0.100 mmol) was placed in a round bottomed flask, to which a 5:2 mixture of 1,4-dioxane: 10% K$_2$CO$_3$ (aq) (3 ml) was added dropwise. The mixture was stirred and Dabsyl chloride (0.033 g, 0.10 mmol) was added to the mixture which was then stirred at RT overnight open to the atmosphere. The solution was diluted with 150 ml water. The layers were separated, and the aqueous layer was extracted with diethyl ether (10 ml×3). The combined organic layers were dried and concentrated. Crude material was purified using flash column chromatography (10:90 MeOH/DCM) to provide compound 4-c. $^1$H NMR (400 MHz, CDCl$_3$ with a drop of CD$_3$OD) 8.55, 7.79, 7.65, 7.52, 7.26, 7.17, 6.69, 6.59, 5.19, 5.06, 4.78, 4.28, 4.17, 4.08, 3.97, 3.57, 3.55, 3.35, 3.05, 2.87, 2.14, 1.99, 1.63, 1.41, 1.21, 0.83, 0.03.

Synthesis of Polymer 4

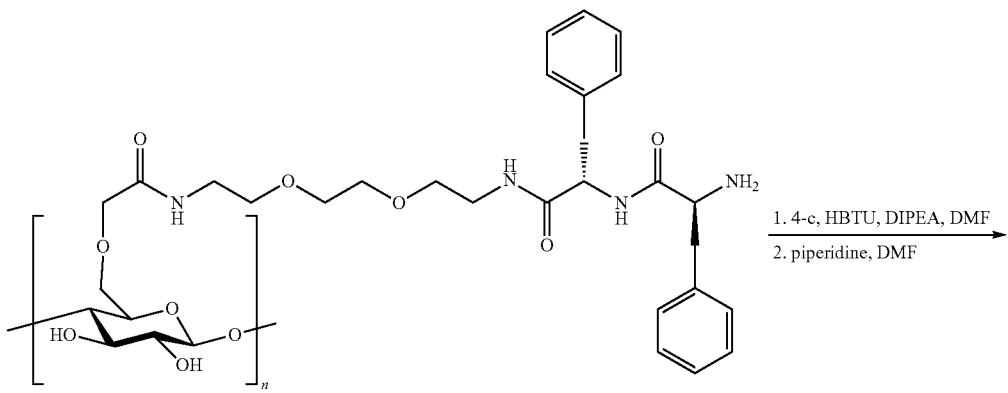

-continued

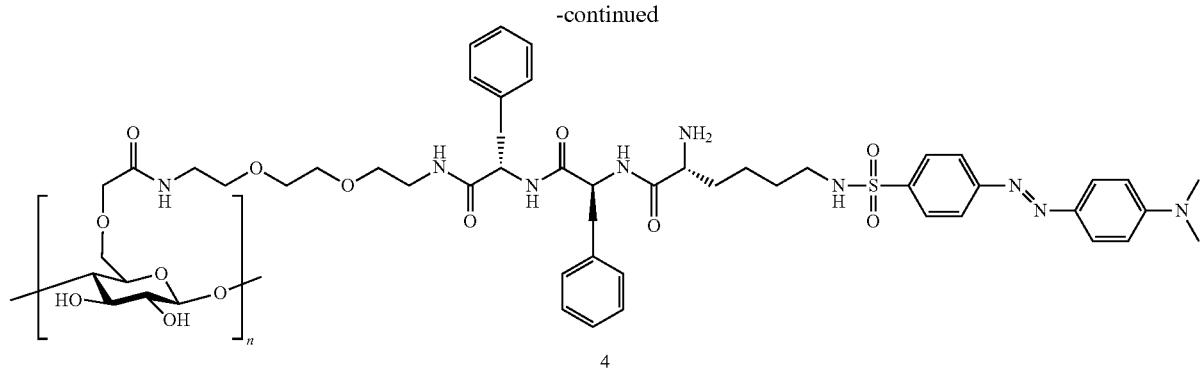

4

A solution of compound 4-c (0.0160 g, 0.024 mmol), HBTU (0.00925 g, 0.0244 mmol), DIPEA (0.23 ml, 1.8 mmol) and dry DMF (6 ml) was prepared. A 15-ml plastic separating column was set up with a 10 μm polyethylene frit and a luer tip. Polymer 3 (0.0230 g, 0.084 mmol) was added to the column followed by the amino acid solution. A lid was placed onto the column and was further sealed with parafilm. The column was placed on a blood rotor at RT overnight. The solution was drained using reduced pressure and the solid product was washed with EtOH (10 ml×3) to provide the coupling product as a red solid, which was washed with DCM. A Kaiser test was used to confirm absence of terminal amines. FTIR: 3346 (N—H/O—H), 2912 (C—H), 1730 (C=C aromatic of Dabsyl), 1652 (C=O, amide of amino acid), 1591 (C=O urethane).

The coupling product was placed in a solution of piperidine: DMF (1:4 v/v), (6 ml) for approximately 2 h. The resulting de-protected product was then washed with EtOH (10 ml×3) followed by DCM (10 ml) to provide Polymer 4 as a red/brown brittle solid. Weight=0.0368 g, yield=56%. A Kaiser test was conducted to confirm presence of terminal amines. FTIR: 3335 (N—H/O—H), 2918 (C—H), 1651 (C=O, amide of amino acid, or Fmoc), 1589 (C=O urethane).

Example 5: Preparation of Polymer 5 (Using Powdered CMC)

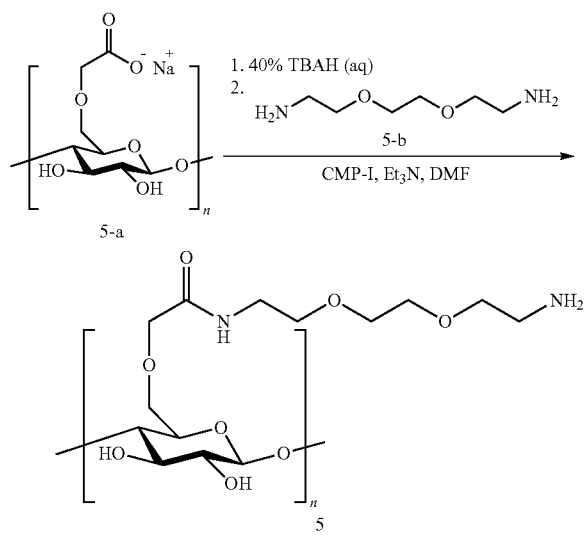

Sodium carboxymethylcellulose (NaCMC) of DoS 0.7 (2.0 g, 8.33 mmol) was dissolved in de-ionized water (180 mL) to give a 1% solution. Dowex 650C monosphere ion exchange resin was added with stirring for 10 minutes. The monospheres were removed by filtration before tetrabutylammonium hydroxide (TBAH) 40% (aq) was added in 0.1 mL aliquots until the pH was 8-9 (3.5 mL, 36.14 mmol). The resulting solution was stirred for 30 minutes before being lyophilized over seven days.

The lyophilized material was dissolved in dry DMF (240 mL) under a nitrogen atmosphere, stirring and gentle heating was required over a period of approximately 2 hours. The solution was cooled to approx. 4° C. before 2-chloro-N-methylpyridinium iodide (CMP-I) (1.5 g, 5.8 mmol) was added with vigorous stirring. 2,2'-(ethylenedioxy)bis(ethylamine) (1.3567 g, 9.17 mmol) was added to the reaction, along with dry triethylamine (5 mL). The reaction was kept at 4° C. and stirred for a minimum of 3 hours, after which 95% ethanol (aq) (80 mL) was added and stirred for 10 minutes at 4° C. 99% acetone (200 mL) was added slowly with stirring to precipitate the product which was filtered and washed with acetone (3×200 mL). The product was concentrated in vacuo to yield an off-white solid. Weight=1.908 g, yield=68%. FTIR: ($v_{max}$/cm$^{-1}$) 3267 (N—H/O—H), 2916/2873 (C—H), 1739 (Acetone), 1650 (C=O, amide of coupled product), 1588 (C=O of CMC), 1401/1314/1257/1037. $^{13}$C CP MAS NMR: CMC 0.7 DoS (starting material): δ C (13,000 Hz, CP MAS) 61.7 (C6), 74.5 (C7, C2, C5), 82.5 (shoulder, C3), 97.0 (C4), 103.3 (C1), 177 (C=O); CMC-PEG di-amine: δ C (13,000 Hz, CP MAS) 13.4 (C14), 20.1 (not assigned), 23.4 (not assigned), 30.6 (C9), 61.7 (C6), 70 (shoulder, C7), 74.5 (C2, C5), 82.5 (C3), 95 (C4), 103.3 (C1), 113 (not assigned), 142 (not assigned), 152 (not assigned), 169.7 (C=O of linker), 177.1 (C=O of CMC). Elemental analysis: Expected of product if DoS of raw material were 0.7: Mass 306 g/mol: C 45%, H 7%, N 6%; (d) Actual: C 43%, H 7%, N 4%. Therefore of all monomers, approximately 47% have been substituted and now contain the linker group. Qualitative Kaiser Test: positive, indicating presence of free amine. UV data obtained at 570 nm equated to 4.6 μmol amine, according to a calibration curve based on valine as a standard reference.

Solubility of Polymer 5 was determined in a similar manner as for compound 1-c. Data is shown below: x indicates insoluble material

| Solvent | Initial | After heating | After sonication | Overnight |
|---|---|---|---|---|
| DCM | x | x | x | x |
| EtOH | x | x | x | x |
| MeOH | x | x | x | x |
| DI water | x | x | became softer | dispersed |
| pH 9 buffer | x | x | x | hydrogel formation |
| pH 4 buffer | x | x | x | some degree of hydrogel formation |

Example 6: Preparation of Polymer 6

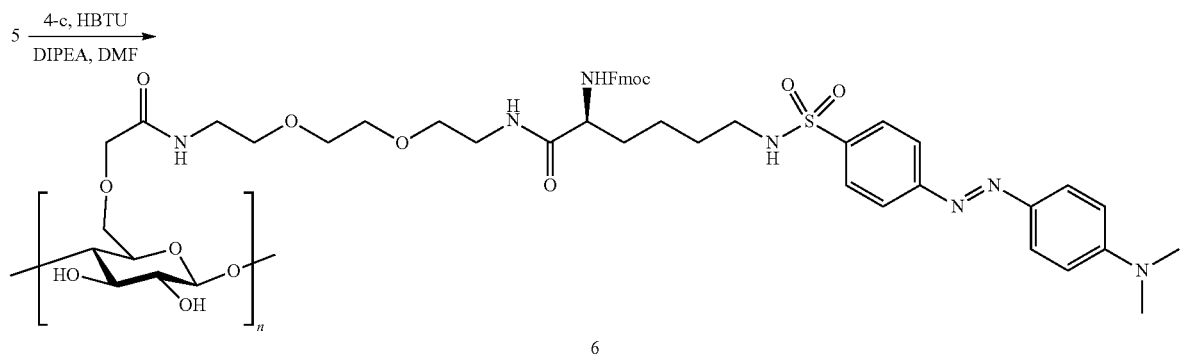

Polymer 5 was soaked in dry DMF (6 mL) for 20 min in a filtration tube. Compound 4-c (0.0416 g, 0.063 mmol) and HBTU (0.2893 g, 0.8571 mmol) were added along with DIPEA (0.2 mL, 0.8571 mmol). The tube was secured and rotated on a lab mixer overnight at RT. The supernatant was filtered and the remaining solid washed with DMF (3×3 mL) and methanol (3×5 mL) before being dried in vacuo. Weight=0.1285 g (45% yield). A Kaiser test was used to confirm presence of free amine. FTIR: 3313 (N—H, O—H), 2862 (β-H), 1747 (C=O of amide), 1587 (C=O of CMC), 1404/1315/1023. Elemental analysis: Carbon: Expected 51%; Actual=40%. Hydrogen: Expected 5%; Actual=6%. Nitrogen: Expected 5%; Actual=4%.

Solubility of polymer 6 was examined in the following manner. A small amount of polymer 6 was placed into two separate glass-bottom petri dishes. The material was saturated with either pH 4 general lab buffer or pH 9 $K_2HPO_4$/$MgCl_2$ buffer (20 μL each). Each was viewed under the Zeiss Axioimager light microscope ×10 magnification optical lens plus ×10 magnification on the eye piece.

Both samples formed hydrogels on contact with buffer. Under the microscope, the powder aggregates appeared to be gelled and contain the red color of Dabsyl. Some areas were more concentrated in color than others but the color distribution was seen across the sample. This experiment was repeated for the starting materials compound 4-c and for polymer 5. There was no color visible in the polymer 5 sample; the hydrogel powder structure was observed. The sample of compound 4-c was red throughout and did not form a hydrogel.

Example 7: Preparation of Polymer 7

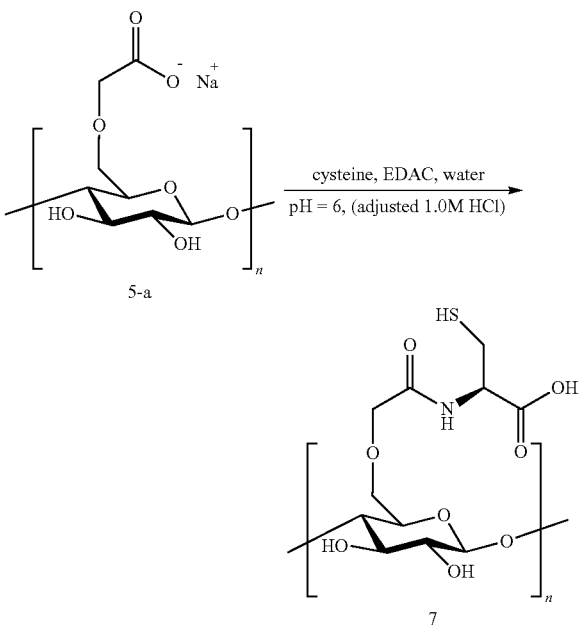

Sodium carboxymethylcellulose (NaCMC) powder (2.0 mg, 8.3 mmol, DoS=0.7) was dissolved in deionized water (200 mL) with stirring, sonication for 60 sec, and gentle heating over the course of 30 min. 1-Ethyl-3-β-dimethyl-aminopropyl)-carbodiimide hydrochloride (EDC) (1.92 g, 10.01 mmol) was added to the solution with stirring. The pH was found to be 8 and was adjusted to pH=6 with addition of 1.0 M HCl (3 drops). L-cysteine (0.50 g, 4.1 mmol) was added to the reaction with stirring. The pH was then found to be 8 and was again adjusted using HCl to reach pH 6 (~1 mL). The reaction was left to stir overnight before dialysis was performed (12-14 KDa Medicell dialysis membranes) against 1 M HCl (700 mL), then 1 M HCl plus 1% NaCl (700 mL), then 0.5 M HCl (700 mL), each of which was performed at 10° C. for 60 min in the dark. The resulting solution was lyophilized to provide Polymer 7. FTIR: 3296 (N—H, O—H), 2972/2930 (C—H), 2733 (small), 2522 (S—H of C), 2089 (v small), 1730 (C=O acid of Cys), 1681 (amide), 1633 (C=O of CMC), 1469 (shoulder), 1382/1346/1221/1107, 1051. $^{13}$C CP MAS NMR: 14 (C11), 18 (not assigned), 24 (not assigned), 43 (C9), 58 (not assigned), 62 (C6), 74 (C2, 3, 5, 7), 82 (C4), 103 (C1), 173 (C8 carbonyl of amide). Elemental analysis: Expected of product if DoS of raw material were 0.7: Mass 299 g/mol: C 40%, H 6%, N 3%, S 6%; Actual: C 34%, H 8%, N 8%, S 1.4%. Therefore of all monomers, approximately 16% contain the linker group.

Solubility of Polymer 7 was determined in a similar manner as for compound 1-c. Polymer 7 was found to be insoluble in water, DMF, acetone, MeOH, EtOH, and DCM.

Example 8: Preparation of Polymer 8

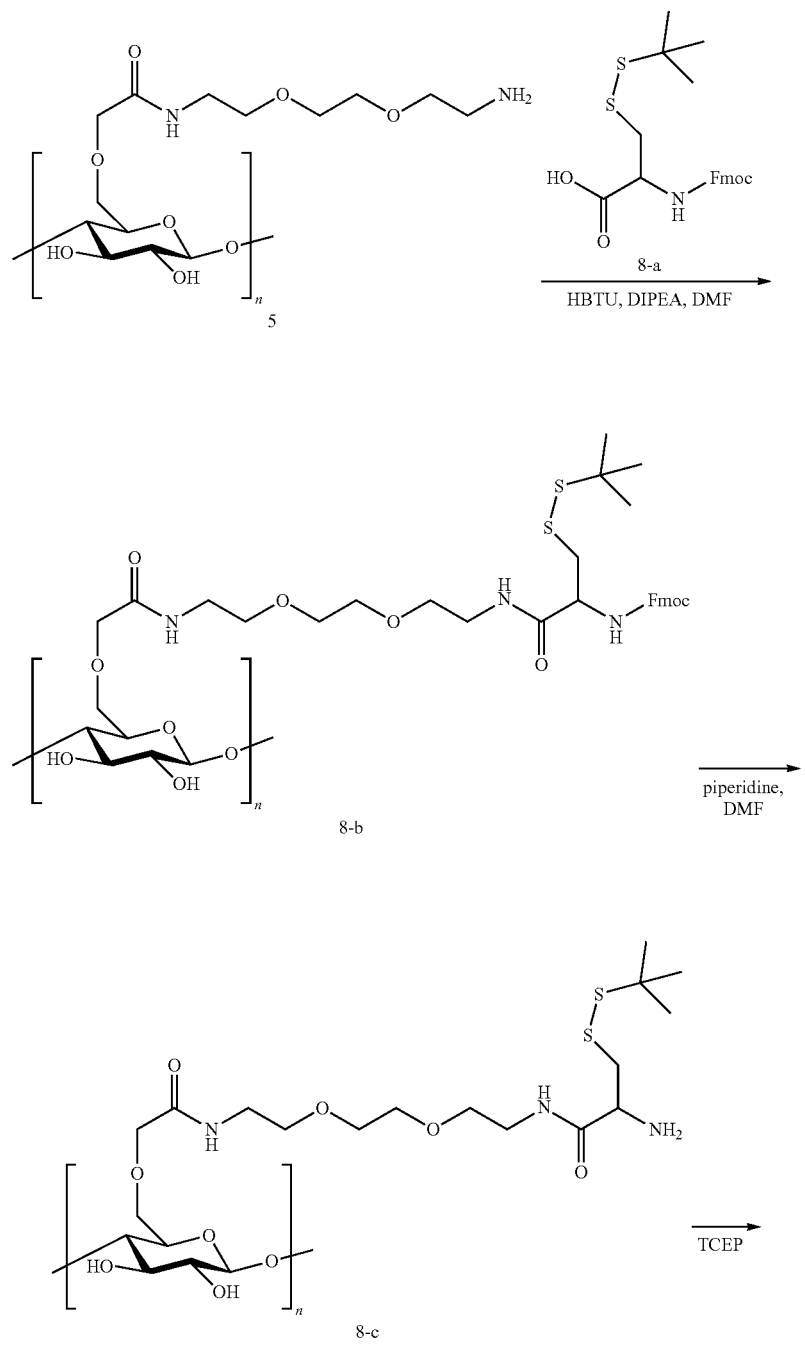

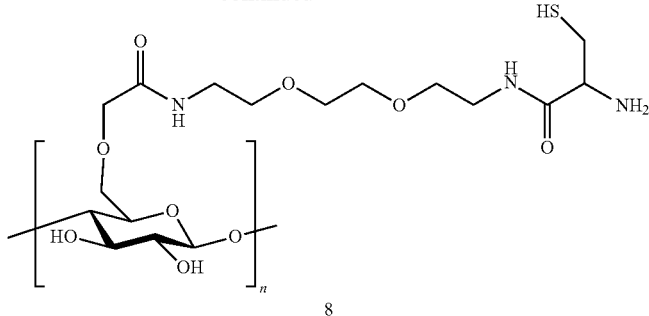

Polymer 5 (1.00 g, 2.86 mmol) was ground into a fine powder and mixed with DMF (25 ml) for 20 min. Fmoc-Cys(StBu)—OH (3.7 g, 8.6 mmol), HBTU (2.87 g, 8.57 mmol) and DIPEA (1.10 ml, 8.57 mmol) were added with stirring at RT, open to air (a centrifuge tube and lab rotor were used to facilitate mixing overnight). The mixture was sonicated for 30 sec before being allowed to stir overnight. The solid was filtered and washed with DCM (20 mL×5) and MeOH (20 mL×5). The resulting product was dried under in vacuo to provide compound 8-b as an off-white solid. 13C CP MAS NMR: 20 (not assigned), 30 (C9), 32 (C19), 39 (C10,11,12,13), 47 (C18, 22), 55 (C16), 61 (C6), 70-74 (broad, C2,3,5,7), 82 (shoulder, C4), 92 (C17), 96 (not assigned), 103 (C1), 120 (C24), 127 (C25,26,27), 141 (C28), 145 (shoulder, C23), 157 (C20, C=Ocarbamate), 171 (C8 carbonyl of amide), 177 (C8 carbonyl of CMC), 191 (not assigned), 221/227 (possible contaminant).

Compound 8-b (0.5 g) was placed on a lab rotor in a solution of piperidine: DMF (20:80 v/v), (10 ml) for approximately 2 h. The resulting de-protected product was then washed with EtOH (50 mL×3) and DCM (50 mL×3) to provide compound 8-c as an off-white solid. This process was repeated to completely remove the Fmoc group.

Compound 8-c (0.30 g, 0.54 mmol) was added to a round bottomed flask and purged with nitrogen gas. Tris(2-carboxyethyl)phosphine (TCEP) (0.307 g, 1.07 mmol) was dissolved in deionized water (1.3 ml) and added to the reaction with stirring along with MeOH (2.6 ml). The system was kept under nitrogen at RT with stirring for 1 h before being filtered and washed with the following solutions: 2:1 MeOH/water (90 ml), 1:2 MeOH/water (90 ml), 100% water (90 ml), 100% MeOH (90 ml). The resulting solid was dried in vacuo to provide Polymer 8 as an off-white solid. This process was repeated to completely reduce the disulfide. 13C CP MAS NMR: 30 (C9, 19), 39 (C10,11,12,13), 47 (C18, 22), 54 (C16), 60 (C6), 70-74 (broad, C2,3,5,7), 82 (shoulder, C4), 92 (C17), 97 (not assigned), 102 (C1), 120 (C24), 127 (C25,26,27), 141 (C28), 156 (C20, C=Ocarbamate), 171 (C8 carbonyl of amide), 177 (C8 carbonyl of CMC), 191 (not assigned), 221(not assigned). Elemental analysis: Expected of product if DoS of raw material were 0.7: Mass 390 g/mol: C 43%, H 6%, N 6%, S 5%; Actual: C 46%, H 7%, N 4%, S 3.5%. Therefore of all monomers, approximately 50% contain the linker group.

Example 9: Preparation of Polymer 9

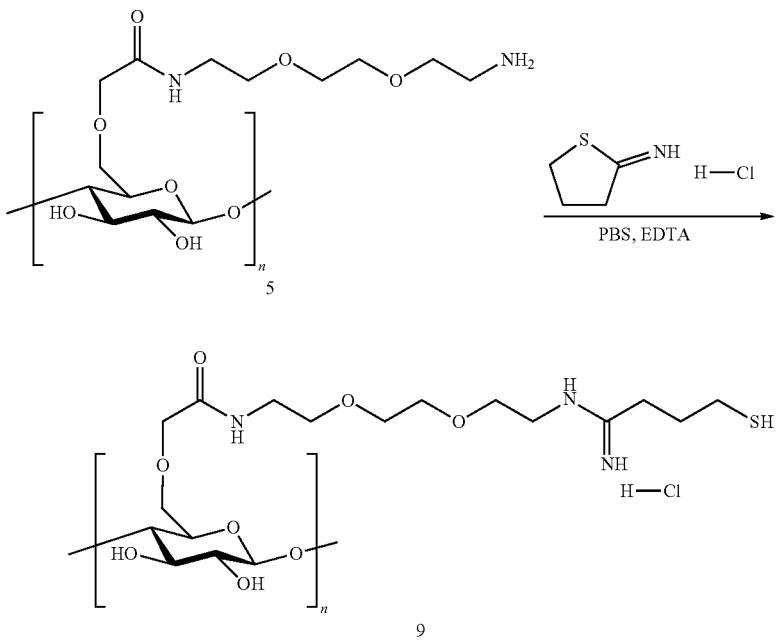

Polymer 5 (1.0 g, 2.714 mmol) was dispersed in PBS (25 mL) with gentle heating, stirring and sonication. The reaction vessel was purged with nitrogen gas. To a solution of Traut's reagent (0.600 g, 4.304 mmol) in PBS (50 mL), was added EDTA (0.044 g, 0.15 mmol). Once fully dissolved, this solution was added to the reaction mixture, which was stirred at RT under nitrogen atmosphere for 1 hour. The resulting product was separated by filtration and washed with PBS (3×10 mL) and methanol (3×10 mL). The white/off-white powdered solid product was then dried in vacuo and stored under nitrogen. Weight=1.2413 g (91%). Yellow color from an Ellman test indicates that some free thiol was still present, possibly in unreacted remaining starting materials. In a quantitative test, there were roughly 0.06 mmol/g of S—H groups present. FTIR: 3315 (N—H/O—H), 2957/2934/2870 (C—H), 1644 (C=O, amide of coupled product), 1593 (C=O of CMC), 1412/1322/1022. There was a very small peak for S—H at 2059 $cm^{-1}$. δ C (13,000 Hz, CP MAS): 176.7 (C8, C=O of CMC), 172.2 (C8, C=O of amide), 156.0 (C15, small peak) 121.0, 103.0 (C1), 81.3 (C7, shoulder), 74.4 (C2,C3,C4,C5), 61.7 (C6), 38.9 plus shoulder (C9,C10,C11,C12,C13,C14). Elemental analysis: Expected of product if DoS of raw material were 0.7: Mass 414 g $mol^{-1}$; C 43%, H 7%, N 6%, S 4%. Actual: C 40%, H 7%, N 4%. Therefore of all monomers, approximately 47% contain the linker group.

Example 10: Preparation of Polymer 10 and washed with PBS (3×20 mL) and methanol (1×20 mL) before being dried in vacuo to produce intermediate 10-a as a pale white/yellow powdered solid. Weight=0.133 g (60% yield). Yellow color from an Ellman test indicates that some free thiol was still present, possibly in unreacted remaining starting materials. In a quantitative test, there were roughly 0.33 mmol/g of S—H groups present. FTIR: 3310 (N—H/O—H), 2911/2875 (C—H), 1727 (C=O carboxylic acid), 1648 (C=O, amide of coupled product), 1592 (C=O of CMC). There was a very small peak for S—H at approximately 2059 $cm^{-1}$. δ C (10,000 Hz, CP MAS): 222.37 (spinning side band), shoulder of 172.5 (C8, C=O of CMC), 172.5 (C8, C=O of amide, possibly also some of the acid group on the Ellman's reagent), 156.0 (C15, small peak) 123.7 (spinning side band), 144.5 (aromatic region of Ellman's Reagent), 103.0 (C1), 96.79, 82.25 (C7, shoulder), 74.5 (C2, C3, C4, C5), 61.4 (C6), 39.3 plus shoulder (C9, C10, C11, C12, C13, C14), 32.2 sharp peak (possible contaminant). Elemental analysis: Expected of product if DoS of raw material were 0.7: Mass 553 g $mol^{-1}$: C 43%, H 6%, N 6%, S 6%. Actual: C 39%, H 6%, N 4%, S 1.45%. Therefore of all monomers, approximately 17% contain the linker group.

The intermediate disulfide product 10-a (0.1 g, 0.1422 mmol), mercaptobenzoic acid (0.11 g, 0.7112 mmol) and methanol: water (4:1 ratio, 5 mL) were combined and stirred for 2 h at RT under nitrogen atmosphere. The resulting product was filtered and washed with methanol (3×10 mL),

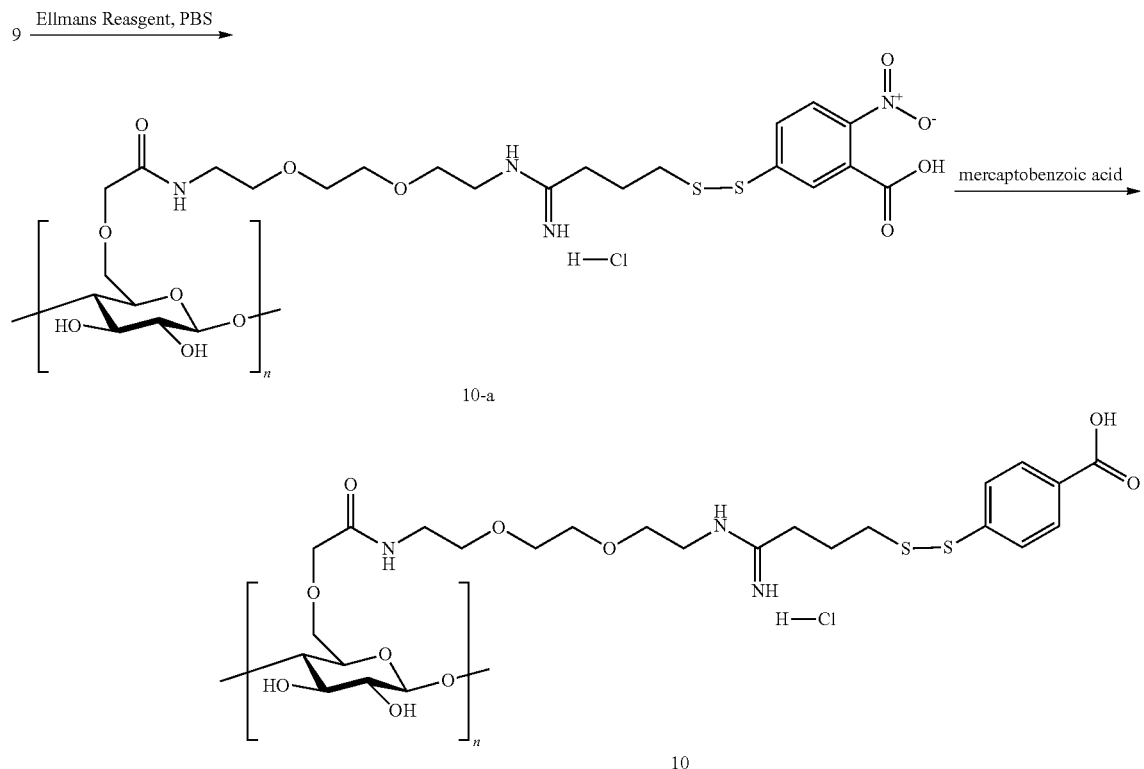

Polymer 9 (0.150 g, 0.316 mmol) was weighed into a round-bottom flask and purged with nitrogen. Ellman's reagent (0.375 g, 0.947 mmol) was dissolved in PBS (20 mL) and added to polymer 9. The reaction was stirred for 2 h at RT. The intermediate disulfide product 10-a was filtered DCM (3×10 mL) and further washed with methanol (3×10 mL) before being dried in vacuo to produce polymer 10 as a yellow solid powder. Weight=0.0821 g (87% yield). Strong yellow color from an Ellman test indicates that some free thiol was still present, possibly in unreacted remaining starting materials. In a quantitative test, there were roughly 2.97 mmol/g of S—H groups present. FTIR: 3293 (N—H/O—H), 2910/2881/2849 (C—H), 1718 (C=O carboxylic acid), 1638 (C=O, amide of coupled product), 1586 (C=O of CMC), 1553. δ C (10,000 Hz, CP MAS): 177.4 (C8, C=O of CMC), 171.9 (C8, C=O of amide, possibly also some of the acid group on the benzoic acid), 130/143 small broad peaks, 102.7 (C1), 96.79, 81.6 (C7, shoulder), 74.1 (C2, C3, C4, C5), 62.5 (C6), 39.0 plus shoulder (C9, C10, C11, C12, C13, C14), 32.1 sharp peak (possible contaminant). Elemental analysis: Expected of product if DoS of raw material were 0.7: Mass 520 g mol$^{-1}$: C, 44%, H, 6%, N, 6%, S, 6%. Actual: C, 37%, H, 6%, N, 3%.

A further wash sequence was performed in water to ensure that any by-products were washed from the structure in the swollen (hydrogel-like) state. pH 9 phosphate buffer (100 mL), deionized water (20 mL), pH 9 phosphate buffer (5 mL) and finally methanol (20 mL) were used to wash the solid which was then dried in vacuo to provide polymer 10 as a white/cream-colored solid powder. Weight=0.0482 g (51% yield). Pale yellow color from an Ellman test indicates that some free thiol was still present, possibly in unreacted remaining starting materials. In a quantitative test, there were roughly 0.31 mmol/g of S—H groups present. FTIR: 3267 (N—H/O—H), 2904/2866 (C—H), 2119 small peak (S—H), 1638 (C=O, amide of coupled product), 1587 (C=O of CMC), 1547. Elemental analysis: Expected of product if DoS of raw material were 0.7: Mass 520 g mol$^{-1}$: C, 44%, H, 6%, N, 6%, S, 6%. Actual: C, 38%, H, 6%, N, 3%, S, 0.65%.

Solubility of polymers 9 and 10 were determined in a similar manner as for compound 1-c. Data is shown below: x indicates insoluble material

| Compd | Solvent | Initial | After heating | After sonication | Overnight |
|---|---|---|---|---|---|
| 9 | pH 9 buffer | x | Not tested | Not tested | Hydrogel formation after mixing |
| 10 | pH 9 buffer | x | Not tested | Not tested | Difficult to tell due to very fine nature of the particles |

Example 11: Preparation of Polymer 11

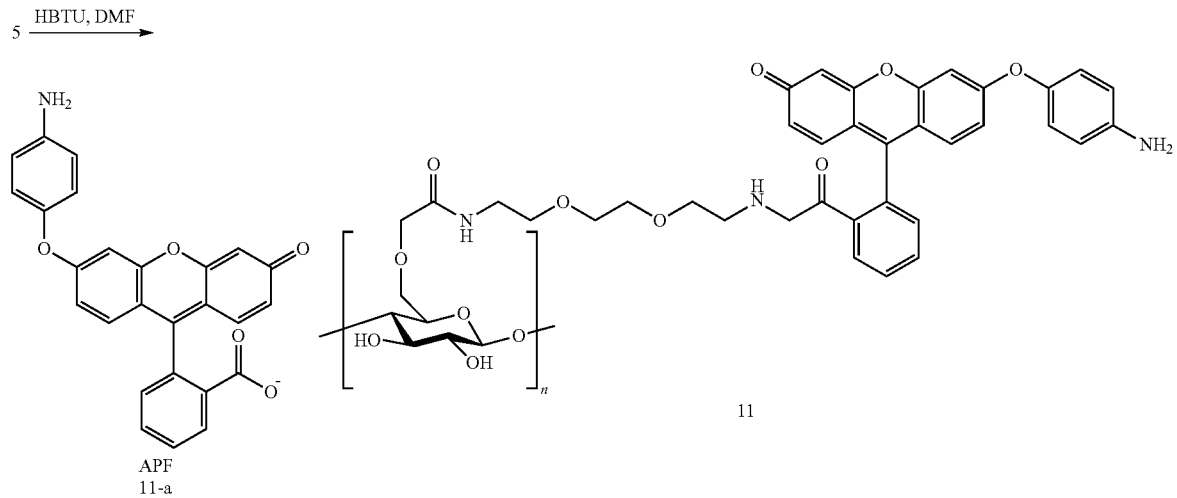

Aminophenyl fluorescein (0.005 g, 0.0180 mmol), HBTU (0.0136 g, 0.036 mmol) and polymer 5 (0.013 g, 0.036 mmol) were added to a 25 mL RBF with a stir bar and purged with N2(g). Dry DMF (5 mL) was added and the reaction was stirred at RT overnight covered with foil to protect from the light. The reaction solution was filtered through a filtration tube and washed several times with DMF. The supernatant maintained an orange color; it was kept along with the washings and dried in vacuo. The solid product was recovered and dried under vacuum. In order to maximize the coupling, and given that the supernatant and washes had some orange color, the reaction was repeated using the recovered solid from the supernatant and washes as the reactants. Weight=0.012 g (43% yield). FTIR: 3367 (N—H/O—H), 2932 (C—H), 1702, 1655 (C=O, amide), 1555 shoulder (C=O of CMC), 1494 (aromatic C—C of APF), 1437/1413/1387/1308, 1194 (C—C), 1106 (C—O of APF), 838 (aromatic out of plane C—H Bending).

Example 12: Preparation of Polymer 12 water and added to polymer 8 (0.01 g, 0.0212 mmol) and was stirred at RT for 30 min. The solid was filtered and washed with water (3×10 mL) and freeze-dried yielding solid off-white/cream colored powder which was then washed with the DMF (3×10 mL).

Compound 12-a (0.0108 g, 0.0212 mmol, 1 equiv) was dissolved in 3 mL dry DMF and was added to polymer 8 which had been purged with $N_2$ (g). The reaction was stirred at RT overnight covered with foil to protect from the light. After being stirred overnight, the reaction mixture had become a red color and when filtered, only a very small amount of white solid material was recovered (0.0022 g). The solution phase was concentrated in vacuo to provide crude polymer 12 as a red waxy solid.

It was probable that the product and starting materials were present in crude polymer 12 and therefore washes were required in order to further purify the crude material. The mixture was insoluble in hexane, ethanol and chloroform. However, when immersed in deionized water and after gentle heating and sonication, the supernatant became an

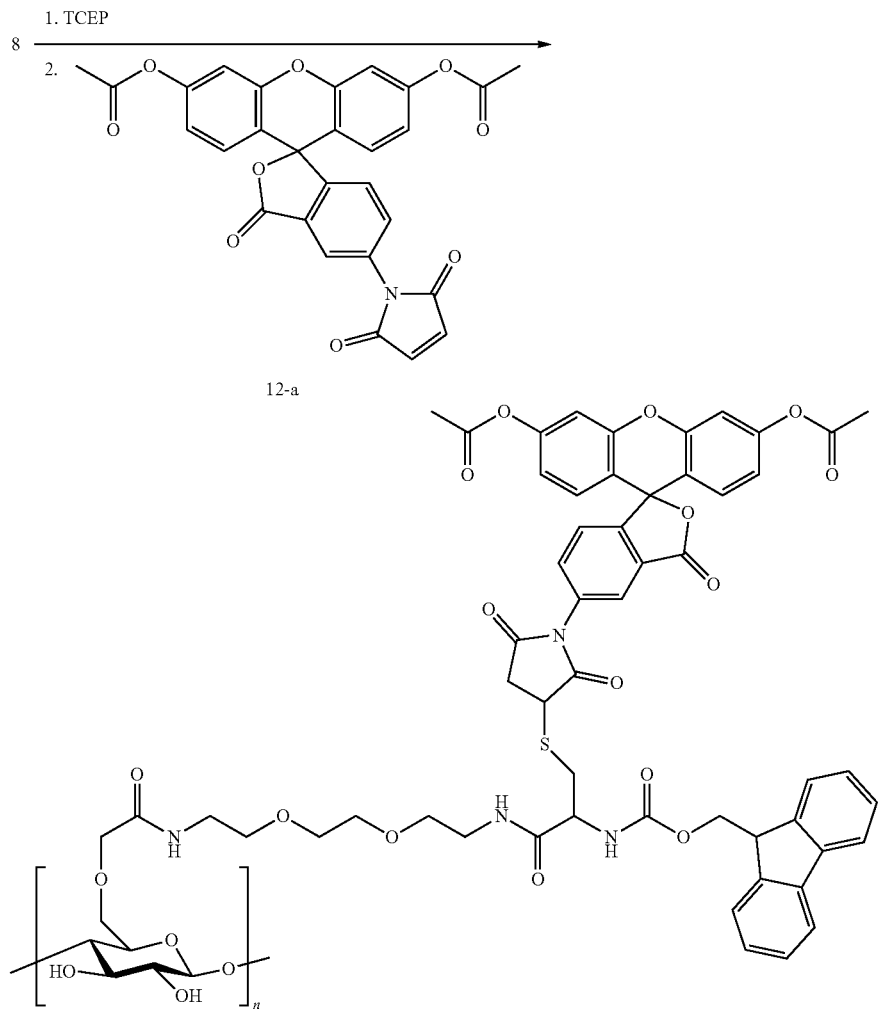

Initially polymer 8 was treated with TCEP in order to de-couple any disulfide bonds that had formed. TCEP (0.0243 g, 0.0848 mmol, 4 equiv) was dissolved in 1 mL orange color which was probably the starting material compound 12-a. The solution was subjected to the following steps 5 times: (1) addition of deionized water (5 mL), (2)

gentle heating with stirring, (3) 1-min sonication repeated 3 times, and (4) filtration through a filtration column and frit filter. A further 50 mL of deionized water was washed through the solid sample. It was then filtered and freeze dried overnight to remove the water. Weight of product: 0.01701 g (85% yield). FTIR: 3347 (N—H/O—H), 2915/2851 (C—H), 1756 (C=O of ester/C=O of fluorescein), 1716 (C=O of ester/C=O of fluorescein), 1643 (C=O, amide of coupled product), 1608 (C=O of CMC/aromatic C=C stretching), 1492 (aromatic C=C stretching), 1369 (C—O stretch of ester), 1246 (C—O stretching), 1152 (t —OH), 1110 (C—O of ester/—OH), 842 (aromatic out of plane C—H bending).

Enzyme Efficacy of Polymer 12

Enzyme efficacy was examined with esterase (~50 units/mL achieved by mixing neat esterase (0.01 mL) in PBS (0.99 mL).

Fluorescence microscopy indicated a distinct observable difference in fluorescence between the sample of polymer 12 and control sample (polymer 12 in PBS without enzyme), demonstrating that there was activity by the enzyme on the polymer to release the ester groups from the attached fluorescein.

Use of a confocal microscope led to visualization of the difference in fluorescence between polymer 12 and the control sample. Microscope settings: smart gain=716 v, smart offset=−2.1%, magnification=×20, Pinhole size=105.05 μm.

In order to quantify and accurately determine enzyme efficacy, a further experiment was set up using a 96 well plate and a plate reader (Fluostar Optima BMG Labtech with excitation set to 485 nm, emission set to 590 nm and gain set to 1500). Polymer 12 was dispersed in 320 μL PBS and vortex mixed. 40 μL of suspension was dispensed into 8 of the wells and a measurement was taken as the baseline reading. The following solutions were prepared: esterase 58 units/mL in PBS (a weak enzyme solution), esterase 116 units/mL in PBS (a strong enzyme solution),1 M NaOH (aq).

N=2 wells had 40 μL of PBS added (control) into the test dispersion only.

N=2 wells had 40 μL of weak enzyme solution pipetted into the test dispersion.

N=2 wells had 40 μL of strong enzyme solution pipetted into the test dispersion.

N=2 wells had 40 μL of 1 M NaOH solution pipetted into the test dispersion.

Another fluorescence reading was recorded immediately after addition to the final well, and thereafter recordings were taken after 5, 10, 15, 20, 25, 30, 35, 40, 45, 50, 55 and 60 minutes. The plate was then covered and left overnight in order to obtain a reading after 24 h. However, the fluorescence detector had reached its limit and therefore meaningful results were not achieved for this time point. Table 2 and FIG. 1 show the fluorescence reading at each time point minus the baseline reading (the particle suspension only).

There is a slight increase in the fluorescence emitted by the negative control over the 1 hour period.

As expected, fluorescence for the weak and strong esterase solutions increases over time. The strong esterase solution appears to have reached the maximum fluorescence intensity that can be measured by the instrument at around 30 min (machine saturation point is 65000). FIG. 1 shows the plot for the strong esterase up to 30 min and plots the trend line for this and the weak esterase over the whole 60 min.

Figure 2A:
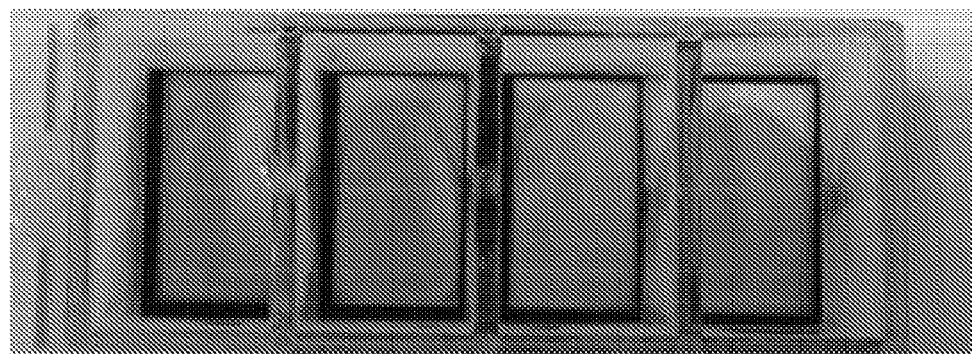
FIG. 2A shows images of Polymer 12 samples used in the fluorescence-based study of FIG. 1 as viewed under ambient light.
Figure 2B:
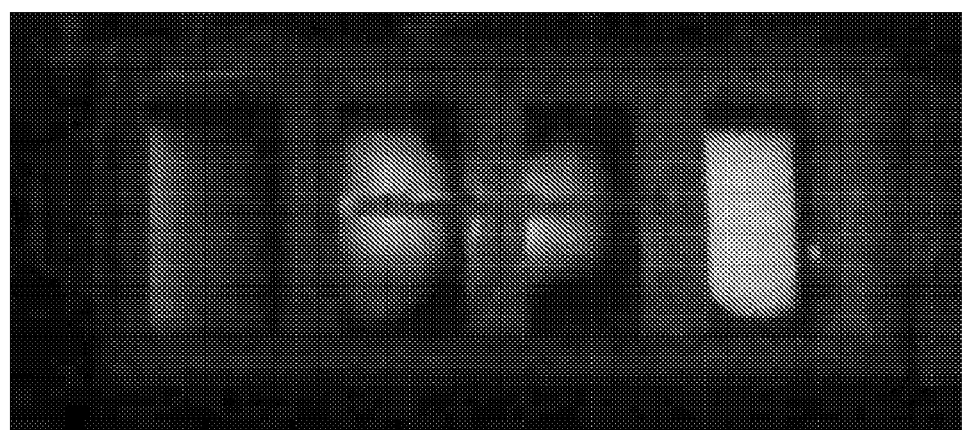
FIG. 2B shows images of Polymer 12 samples used in the fluorescence-based study of FIG. 1 as viewed under UV light.
Figure 2C:
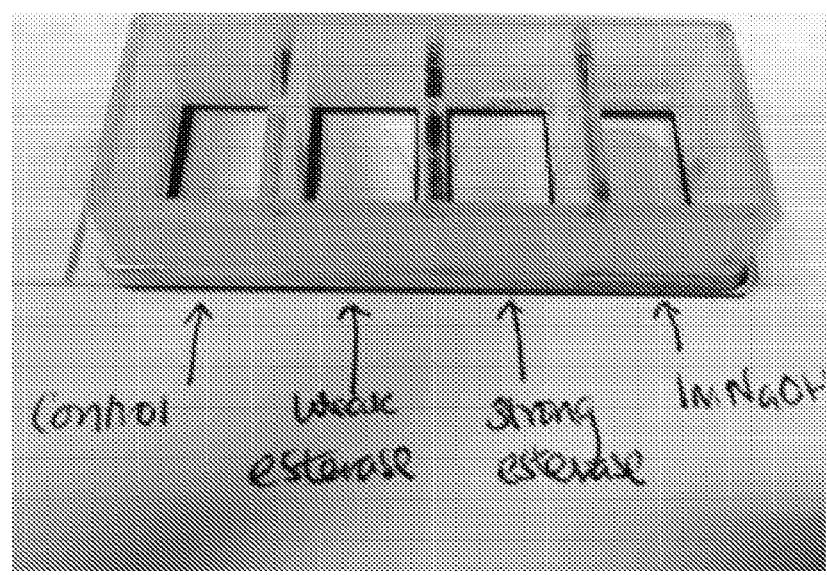
FIG. 2C shows the labeling of individual Polymer 12 samples used in the fluorescence-based study of FIG. 1.

Following this experiment, each solution (n=1 only) was pipetted out of its well and into a glass bottomed microscope well for examination by the naked eye. It was also placed into the UV chamber set to the long wavelength setting and images were captured (FIG. 2a-c).

Taken together, this evidence suggests that the synthetic method was successful and that the enzyme cleavage step gives a positive response which can be quantified by fluorescence spectroscopy. The sample of polymer 12 fluoresces even without the addition of esterase which suggests perhaps that coupling has been over-done a little.

Example 13: Preparation of Polymer 13 (using CMC fiber)

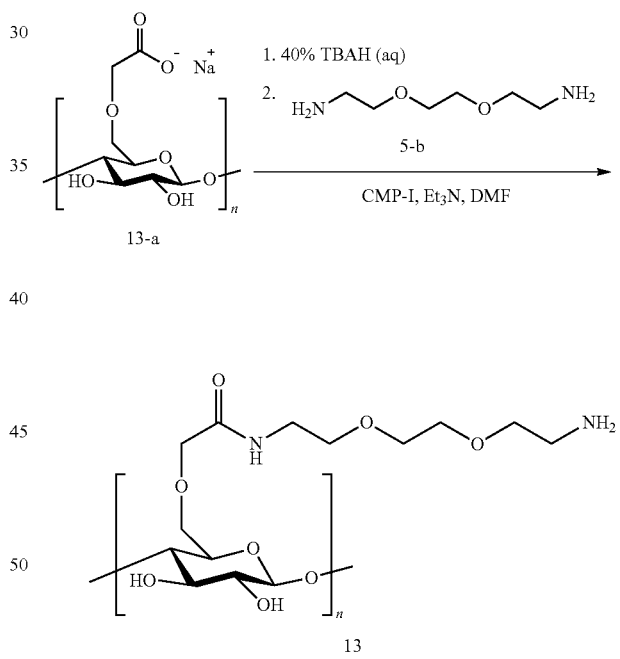

TABLE 2

| | Time Point (minutes) | | | | | | | | | | | |
|---|---|---|---|---|---|---|---|---|---|---|---|---|
| | 0 | 5 | 10 | 15 | 20 | 25 | 30 | 35 | 40 | 45 | 55 | 60 |
| Control | 3431 | 4032 | 4602 | 5317 | 6113 | 6717 | 7267 | 7749 | 8345 | 8866 | 9842 | 10106 |
| Esterase 58 units/mL | 7623 | 13503 | 17730 | 21112 | 24604 | 27171 | 29553 | 31739 | 33850 | 36012 | 40127 | 41740 |
| Esterase 116 units/mL | 14414 | 23985 | 30324 | 34483 | 38727 | 41670 | 44455 | 45121 | 45121 | 45121 | 45121 | 45121 |

NaCMC fiber (2×AQUACEL Dressings 10×10 cm) with DoS approx. 0.2-0.3 (1.97 g, 8.33 mmol) was broken apart into small, open fibers by hand and dispersed in a solution of ethanol/deionized water (80:20 v/v) (180 mL). Dowex 650C monosphere ion exchange resin was added in order to provide the acidified CMC (CMC-H) and was mixed for approximately 30 min. The monospheres were removed carefully by filtration and tetrabutylammonium hydroxide (TBAH) 40% (aq) was added until the pH was 8-9. The resulting solution was stirred for 30 min before being concentrated in vacuo. The dried material was dissolved in dry DMF (150 mL) under nitrogen. Stirring overnight was required and the resulting solution was very viscous with a clear/yellow color. A further addition of dry DMF (100 mL) was made in order to reduce the viscosity and the mixture was cooled to about 4° C. and stirred before 2-chloro-N-methylpyridinium iodide (CMP-I) (1.4875 g, 5.8 mmol) was added. Shortly afterwards, compound 5-b (1.3567 g, 9.17 mmol) was added along with dry triethylamine (5 mL). The reaction was kept at 4° C. and stirred overnight. The solid was filtered and then washed with acetone (3×100 mL) then DMF (3×100 mL), sonication was performed during the wash steps in order to encourage the fibers to disperse in the wash solution. The solid was dried further in vacuo to yield polymer 13 as off-white fluffy/powdery fibers. Weight=1.8365 g (60% yield). A Kaiser test was used to confirm presence of terminal amines (a reading at 570 nm equating to 3.08 nmol amine). SS NMR: δ (10,000 Hz, CP MAS) 176.9 (C=O) 153.4, 142.4, 104.1 (C1), 96.8 (C4), 83.6 (C3), 74.2 (C7, C2, C5), 69.4 (C6), 61.9 (C6, shoulder). FTIR: 3325 (N—H/O—H), 2872 (C—H), 1648 (C=O, amide of coupled product), 1589 (C=O of CMC), 1543, 1408/1367/1265/1022. Elemental analysis: Expected of product if DoS of raw material were 0.7: Mass 318 g mol$^{-1}$: C 45%, H 7%, N 6%. Actual: C 42.5%, H 7%, N 3%. Therefore of all monomers, approximately 35% contain the linker group.

Solubility of Polymer 13 was determined in a similar manner as for compound 1-c. Data is shown below: x indicates insoluble material.

| Solvent | Initial | After heating | After sonication | Overnight |
|---|---|---|---|---|
| pH 9 buffer | x | Not tested | Not tested | Hydrogel formation after mixing |

Example 14: Preparation of Polymer 14

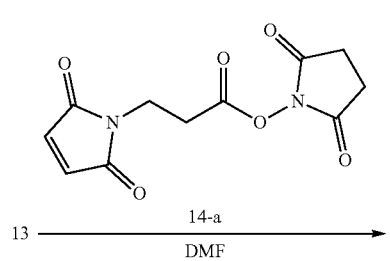

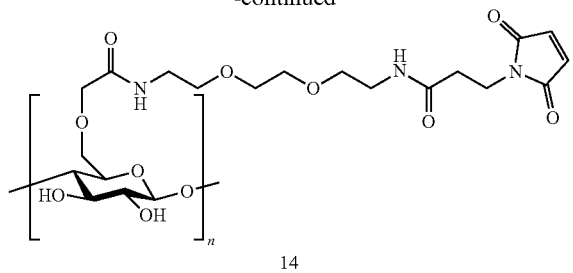

Polymer 13 (0.250 g, 1.396 mmol) was placed in a RB flask under a nitrogen atmosphere. Compound 14-a (90 mg, 0.679 mmol) was dissolved in dry DMF (5 mL) under nitrogen atmosphere and added to polymer 13 with stirring. The reaction mixture was stirred for 90 min at RT under a nitrogen atmosphere before being filtered and washed with DMF (5×5 mL) and methanol (5×5 mL). The product was concentrated in vacuo to yield polymer 14 as off-white powdery solid. Weight=0.1852 g (52% yield). A Kaiser test was used to confirm presence of terminal amines (a reading at 570 nm equating to 1.86 nmol amine). FTIR: 3251 (N—H/O—H), 2915/2874 (C—H), 1649 (C=O, amide of coupled product), 1583 (C=O of CMC), 1405/1316/1262/1020. Elemental analysis: Expected of product if DoS of raw material were 0.7: Mass 519 g mol$^{-1}$: C 48%, H 5.8%, N 5.6%. Actual: C 42.8%, H 6.95%, N 4.25%. Therefore of all monomers, approximately 53% contain the linker group.

Solubility of Polymer 14 was determined in a similar manner as for compound 1-c. Data is shown below: x indicates insoluble material.

| Solvent | Initial | After heating | After sonication | Overnight |
|---|---|---|---|---|
| pH 9 buffer | x | Not tested | Not tested | Slight swelling/gelling over time; particles well dispersed |

Example 15: Preparation of Polymer 15

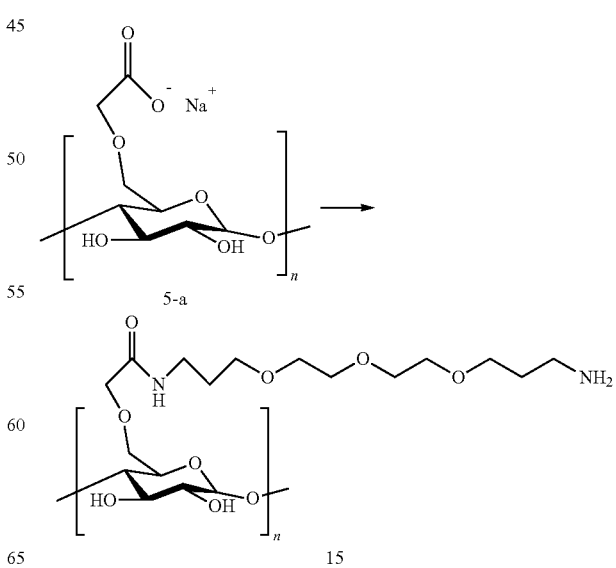

Polymer 5-a (prepared as in Example 5 using 2.0 g of NaCMC) was dissolved in dry DMF (150 mL) under nitrogen. Stirring and heating to ~50° C. was required over a period of ~2 h in addition to multiple cycles of sonication for 1 min to provide a clear solution. The solution was cooled to ~4° C. and stirred before 2-chloro-N-methylpyridinium iodide (CMP-I) (1.4875 g, 5.8 mmol) was added. The solution became a viscous "jelly" and was mixed vigorously and a further 20 mL dry DMF was added which broke down and diluted the gel. Shortly after this 4,7,10-trioxa-1,13-tridecanediamine (12.02 g, 2.02 mL, 9.17 mmol) was added along with dry triethylamine (5 mL). The reaction was kept at 4° C. and stirred overnight. Acetone (100 mL) was cooled to 4° C. and the reaction mixture dripped in slowly with stirring. The mixture was filtered in 20 mL aliquots to give a clear, white gelled solid. This solid was washed in acetone (3×100 mL), ethanol (3×100 mL), water (1×100 mL), hexane (1×100 mL), and then again with water (1×100 mL) before being concentrated for approximately 15 minutes. The resulting product was lyophilized over a 3 day period to provide polymer 5-a as a light and fluffy solid. Weight=1.794 g (49% yield). A Kaiser test was used to confirm presence of terminal amines (a reading at 570 nm equating to 1.86 μmot amine). 13C NMR (101 MHz, None) δ 176.51 (C8, C=O of CMC), 171.09 (C8, C=O of amide), 163.79 (New peak), 153.15, 143.12, 103.40 (C1), 82.39 (C7), 75.81/73.99/70.07 (C2, C3, C4, C5), 60.81 (C6), 42.54/36.84 (C11, C12, C13, C14, C15, C16), 31.45(C9, C14), 28.25. FTIR: Peaks at 3239 (N—H/O—H), 2865 (C—H), 1650 (C=O, amide of coupled product), 1586 (C=O of CMC), 1404/1388/1315/1256/1053. Elemental analysis: Expected of product if DoS of raw material were 0.7: Mass 369 g mol$^{-1}$:C 47.5%, H 7%, N 4%. Actual: C 45.5%, H 7.4%, N 5.1%. Therefore of all monomers, approximately 87.5% contain the linker group.

Example 16: Preparation of Polymer 16

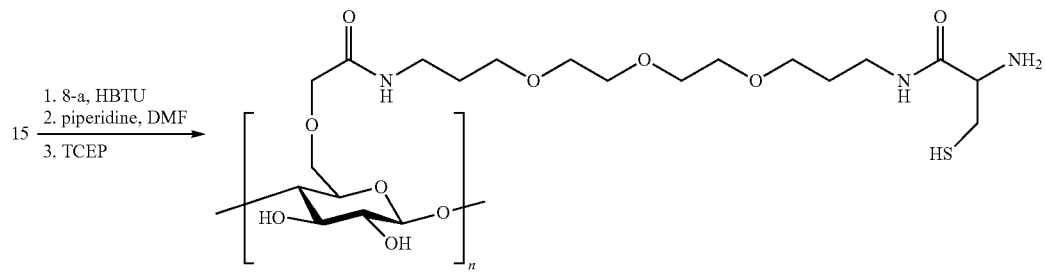

Polymer 15 (1.000 g, 2.273 mmol) was ground into a fine powder and mixed with DMF (15 mL) for 20 min. Compound 8-a (1.14 g, 2.639 mmol), HBTU (2.59 g, 6.82 mmol) and DIPEA (1.19 mL, 6.82 mmol) were added with stirring at RT, open to air (a centrifuge tube and lab rotor were used to facilitate mixing overnight). The mixture was sonicated for 30 s before being allowed to stir overnight. The solid was filtered and washed with DCM (5×20 mL) and methanol (5×20 mL). The resulting coupled intermediate was dried in vacuo. This intermediate (850 mg) was added to a solution of piperidine: DMF (20:80 v/v), (20 mL) and bubbled with nitrogen gas in order to stir the mixture for 1 hour, after which the solid was filtered and washed with ethanol (3×50 mL) and DCM (3×50 mL). This process was then repeated and the amine intermediate was dried in vacuo. This amine intermediate was added to a RB flask and purged with nitrogen gas. TCEP (428 mg) was dissolved in deionized water (2.6 mL) and added to the amine intermediate with stirring, followed by the addition of methanol (5.2 mL). The system was kept under nitrogen at RT with stirring for 1 h before being filtered and washed with the following solutions: 2:1 methanol: water (90 mL), 1:2 methanol: water (90 mL), 100% water (90 mL), 100% methanol (90 mL). The resulting solid was dried in vacuo to provide polymer 16 as an off-white powdered solid. Weight=0.3537 g (30% yield). Yellow color from an Ellman test indicates that free thiol was present. FTIR: 3349 (N—H/O—H), 2917/2872 (C—H), 1716 (acetone), 1650 (C=O, amide of coupled product), 1593 (C=O of CMC), 1539, 1438/1313/1255/1028. δ C (10,000 Hz, CP MAS): 171.8 (C8,C19) 156.5 (residual C=O of Fmoc), 142.3 (residual CHAr of Fmoc), 127.9 (residual CHAr of Fmoc), 120.08, 103.3 (C1), 82.6 (C7), 74.5(C2, C3, C4, C5), 69.9 (x), 61.5(C6), 49.5(C20), 36.37 (C9, C18, C21), 29.52 (C10-18). Elemental analysis: Expected of product if DoS of raw material were 0.7: Mass 440.7 g C 45%, H 7%, N 5.4%, S 4.1%. Actual: C 47.1%, H 6.74%, N 4.11%, S 0.80%. Therefor of all monomers, approximately 20% contain the linker groups.

Solubility assessment indicates that polymer 16 forms a hydrogel in pH 9 buffer (K$_2$HPO4/MgCl2).

Example 17: Preparation of Polymer 17

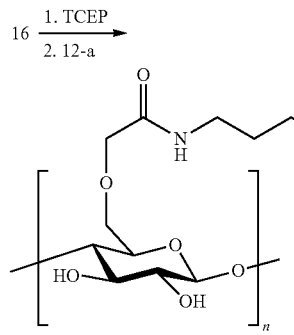
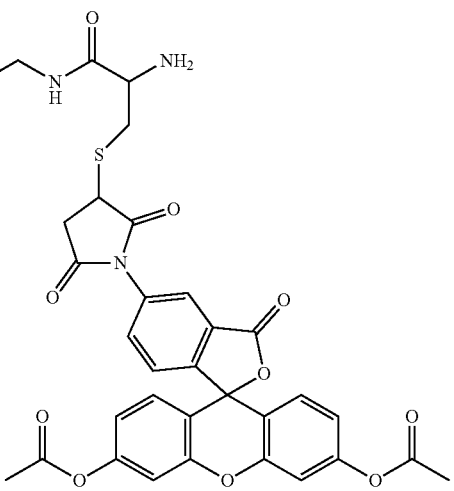

Initially, polymer 16 was treated with TCEP in order to de-couple any disulfide bonds that had formed. TCEP (0.1685 g, 0.196 mmol, 4 equiv) was dissolved in 1 mL water and added to polymer 16 (0.0754 g, 0.147 mmol) and was stirred at RT for 30 min. The solid was filtered and washed with water (3×10 mL) and freeze-dried yielding solid off-white/cream colored powder which was then washed with the DMF (3×10 mL).

Compound 12-a (0.0250 g, 0.049 mmol, 1 equiv) was dissolved in 2 mL dry DMF and was added to polymer 16 which had been purged with N$_2$ (g). The reaction was stirred at RT overnight covered with foil to protect from the light. After being stirred overnight, the reaction had not changed color. An off-white solid powder was filtered and washed as follows, repeating each step 5 times: (1) addition of deionized water (5 mL), (2) gentle heating with stirring, (3) 1-min sonication repeated 3 times, (4) filtration through a filtration column and frit filter, and (5) further flush with deionized water (20 mL). The resulting solid was filtered and freeze-dried for 3 hours to provide polymer 17 as an off-white product. Weight=0.063 g (44% yield). FTIR: 3315 (N—H/O—H), 2911/2869 (C—H),1922, 1756 (C=O of ester/C=O of fluorescein), 1720 (C=O of ester/C=O of fluorescein), 1647 (C=O, amide of coupled product), 1591 (C=O of CMC/aromatic C=C stretching), 1420 (aromatic C=C stretching), 1366 (C—O stretch of ester), 1248 (C—O stretching), 1050 (C—O of ester/—OH), 894 (aromatic out of plane C—H bending. δ C (10,000 Hz, CP MAS): 171.0 (C8,C19, C40) 153.1 (C22, C37), 141.7 (C—CAr), 127.0 (C—CAr), 102.4 (C1), 81.9 (C7, C33), 74.5(C2, C3, C4, C5), 68.6 (C23, C34), 61.5(C6), 46.7(C20), 36.5 (C9, C18), 32.1 (C21), 29.5 (C10-17). Elemental analysis: Expected of product if DoS of raw material were 0.7: Mass 797.7 g mol$^{-1}$: C 52%, H 5%, N 3.5%, S 2.1%. Actual: C 42.8%, H 6.95%, N 4.02%, S 0.52%. Therefore of all monomers, approximately 25% contain the linker group.

Enzyme Efficacy of Polymer 17

Enzyme efficacy was examined with esterase (~58 units/mL achieved by mixing neat esterase (0.01 mL) in PBS (0.99 mL).

In order to quantify and accurately determine enzyme efficacy, an experiment was set up using a 96 well plate and a plate reader (Fluostar Optima BMG Labtech with excitation set to 485 nm, emission set to 590 nm and gain set to 1500). Preparation of the samples: 0.4 mg of polymer 17 was soaked in 640 n.1_, of PBS for 24 h. After soaking, the PBS solution had not altered and remained clear. The mixture was centrifuged to remove most of the solids, and at this point the sample of polymer 17 appeared to have become a hydrogel. The eluent was then filtered and analyzed; the solid hydrogel was kept aside for additional experimentation. 40 n.1_, of the eluent was dispensed into wells with thorough mixing before each aliquot. A measurement was taken as the baseline reading. The following solutions were prepared: esterase 58 units/mL in PBS (a weak enzyme solution), esterase 116 units/mL in PBS (a strong enzyme solution).

N=4 wells had 40 μL of PBS added (control) into the test dispersion only.

N=4 wells had 40 μL of weak enzyme solution pipetted into the test dispersion.

N=4 wells had 40 μL of strong enzyme solution pipetted into the test dispersion.

Figure 3:
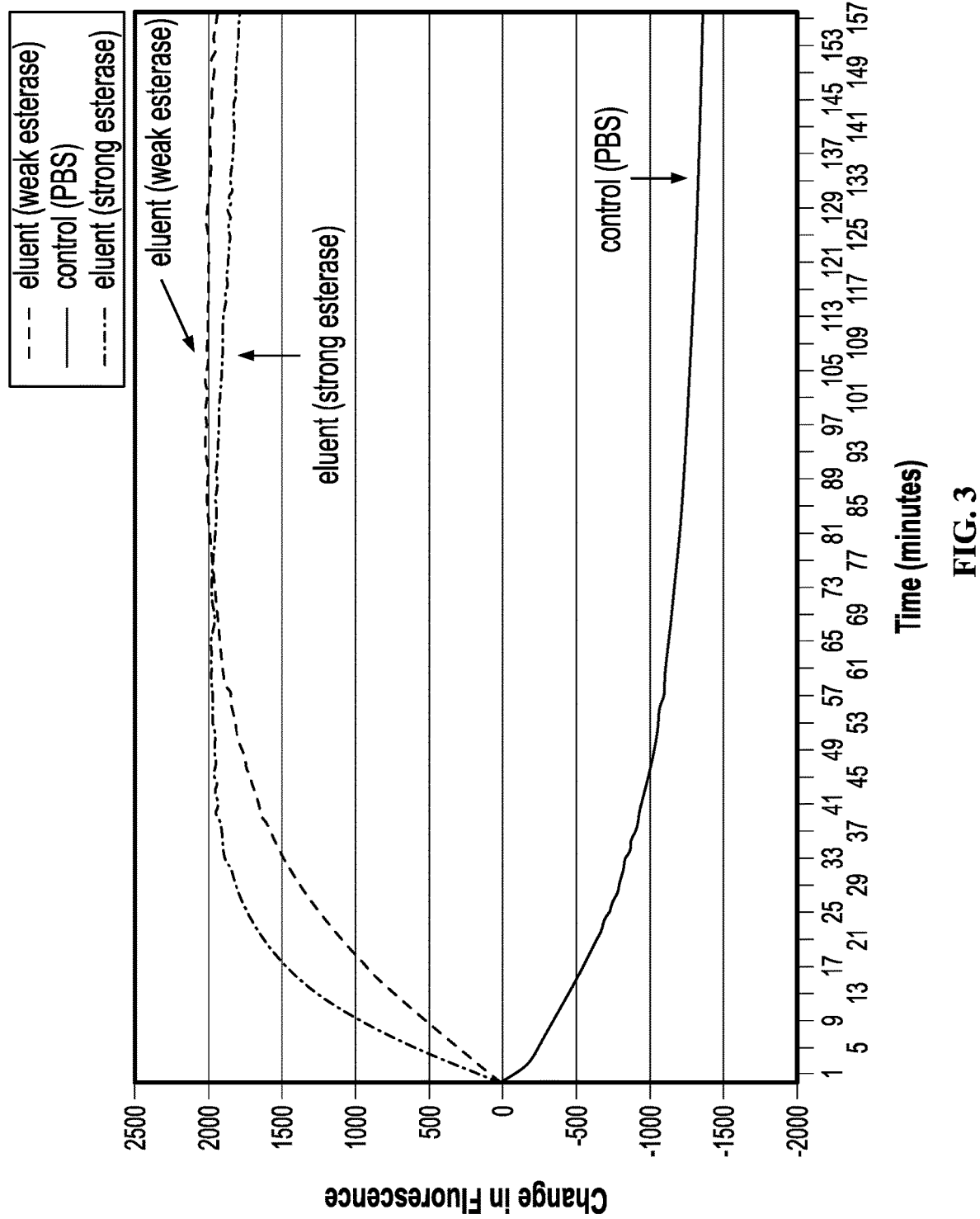
FIG. 3 shows quantitation of enzyme efficacy of Polymer 17 (pretreated with PBS) using a fluorescence-based study: eluent after PBS-soaking period.

Another fluorescence reading was recorded immediately after addition to the final well, and thereafter recordings were taken every 60 sec for 160 minutes. FIG. 3 shows the fluorescence reading at each time point minus the baseline reading (the particle suspension only). The instrument did not reach the saturation point during this experiment as it had previously. As expected, fluorescence for the weak and strong esterase solutions increased over time.

Fluorescence of the negative control sample (sample without enzyme, PBS only) slightly increased over time.

Figure 4:
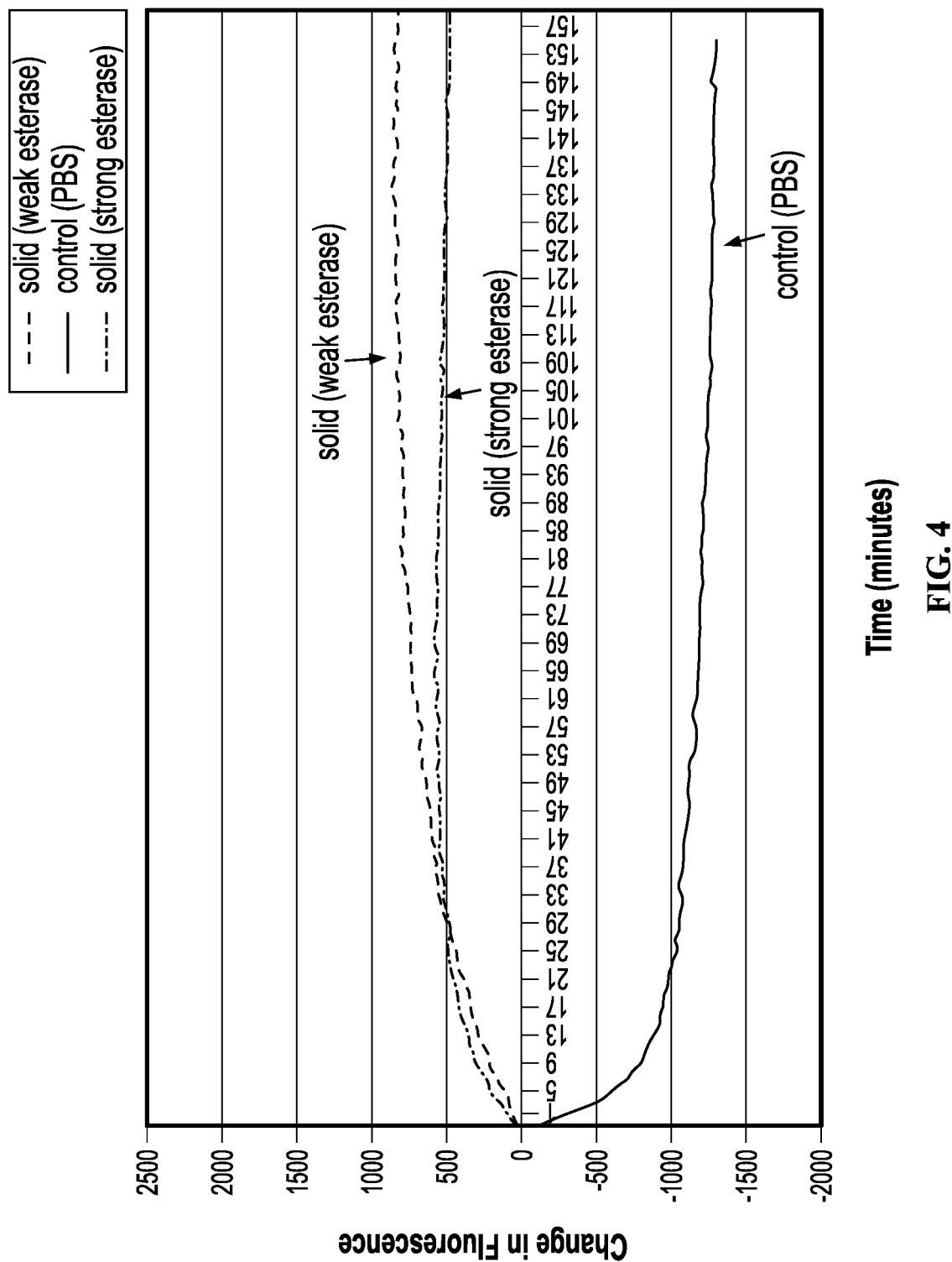
FIG. 4 shows quantitation of enzyme efficacy of Polymer 17 (pretreated with PBS) using a fluorescence-based study: solid re-suspended in PBS after initial PBS-soaking period.

Further to the above experiment, an additional control experiment was performed using the solid filtrate. The solid was added to 640 μL of PBS, vortex mixed and sonicated until a good dispersion was observed. The solution was analyzed using the same kinetic method described above (see FIG. 4 for results). Taken together, this evidence suggests that the synthetic method was successful and that the enzyme cleavage step gives a positive response which can be quantified by fluorescence spectroscopy. Polymer 17 is not as fluorescent as polymer 12 in the absence of esterase, indicating that less fluorescent label is attached to the polymer.

Example 18: Preparation of Polymer 18

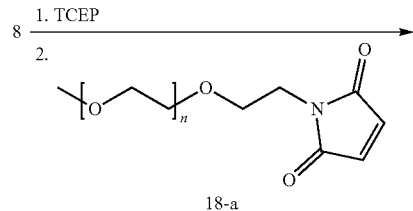

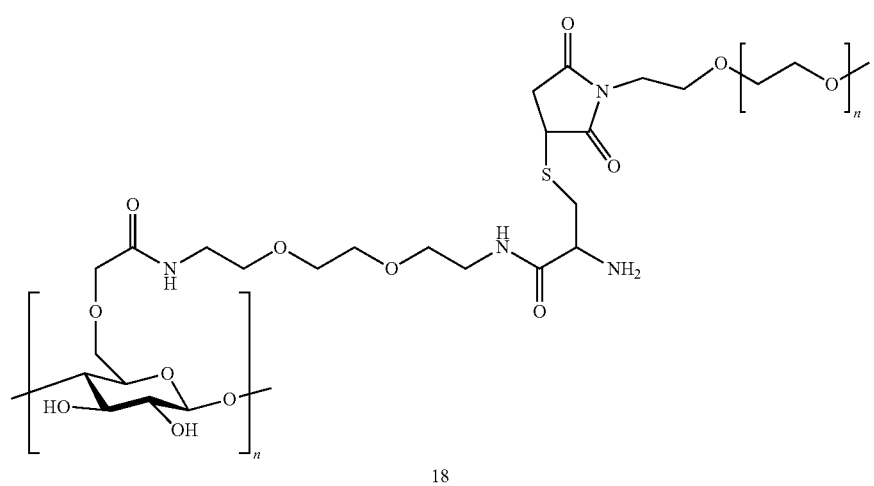

18

Initially polymer 8 was treated with TCEP in order to de-couple any disulfide bonds that had formed. TCEP (0.0243 g, 0.0848 mmol, 4 equiv) was dissolved in 1 mL water and added to polymer 8 (0.01 g, 0.0212 mmol) and was stirred at RT for 30 min. The solid was filtered and washed with water (3×10 mL) and freeze-dried yielding solid off-white/cream colored powder which was then washed with the DMF (3×10 mL).

Methoxypolyethyleneglycol maleimide (compound 18-a) (0.01 g, 0.0543 mmol, 2.5 equiv) was dissolved in 2 mL dry DMF and was added to polymer 8 which had been purged with N$_2$(g). The reaction was stirred at RT overnight covered with foil to protect from the light. After being stirred overnight, the reaction mixture had become a red color and when filtered, there was no solid phase. The filter was rinsed with DMF (5 mL) and the solution was combined and reduced in vacuo to give a clear/yellow oil (weight=0.0106 g). Chilled deionized water (2 mL) was dropped into the oil slowly at 4° C. and then freeze dried to yield polymer 18 as an off-white/pink waxy solid. Weight=6.42 mg. A non-quantitative Kaiser test indicated no free amines present.

FTIR: 3350 (small, N—H/O—H), 2881 (C—H), 2740 (C—H), 1964, 1710 (5-membered cyclic ketone), 1665 (C═O, amides), 1359 (C—O stretch of ester), 1240 (C—O stretching), 1145/1100 (C—O of ester/-OH), 842 (aromatic out of plane C—H bending.

Solubility assessment indicated ready solubility in chloroform, PBS, and DMF.

Example 19: Preparation of Polymer 19

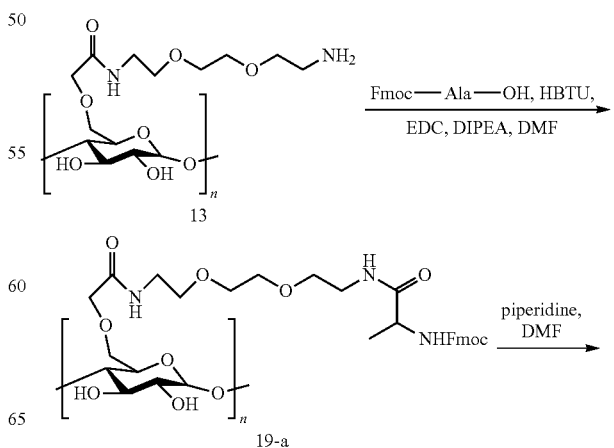

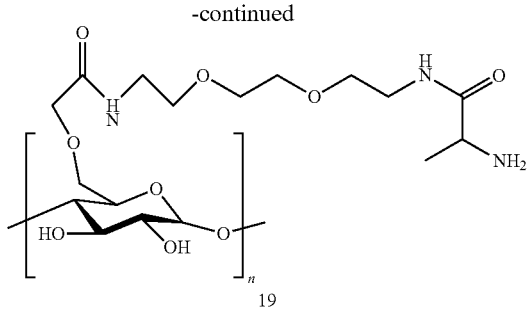

Polymer 5 (300 mg, 0.81 mmol) was ground into a fine powder and mixed with DMF (20 mL) for 20 minutes. Fmoc-Ala-OH (1.00 g, 2.31 mmol), HBTU (1.84 g, 4.86 mmol), EDC (100 mg, 0.52 mmol) and DIPEA (6.2 mL, 4.86 mmol) were added to a large centrifuge tube and purged with nitrogen. A lab rotor was used to facilitate mixing overnight. The solid was filtered and washed with DCM (5×20 mL) and methanol (5×20 mL). The resulting product was dried to provide Polymer 19-a as an off-white powder. Weight=0.2932 g. A positive Kaiser test indicated incomplete coupling. FTIR: 3300 (N—H/O—H), 2850 (C—H), 1748 (amide), 1648 (C=O, amide of coupled product), 1589 (C=O of CMC), 1403/1022, 896.

Polymer 19-a (207 mg) was placed in a solution of piperidine: DMF (20:80 v/v), (20 mL) and purged with nitrogen gas and stirred for 1 hour, after which the solid was filtered and washed with ethanol (3×50 mL) and DCM (3×50 mL). This process was then repeated, and the product was dried to provide Polymer 19 as an off-white powder. Weight=0.345 g (60% yield). A positive Kaiser test result confirmed presence of free amine. FTIR: 3300 (N—H/O—H), 2850 (C—H), 1748 (amide), 1648 (C=O, amide of coupled product), 1589 (C=O of CMC), 1403/1022, 896.

Example 20: Preparation of Polymer 20

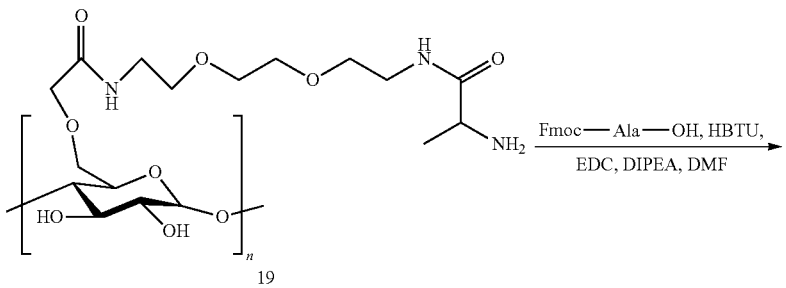

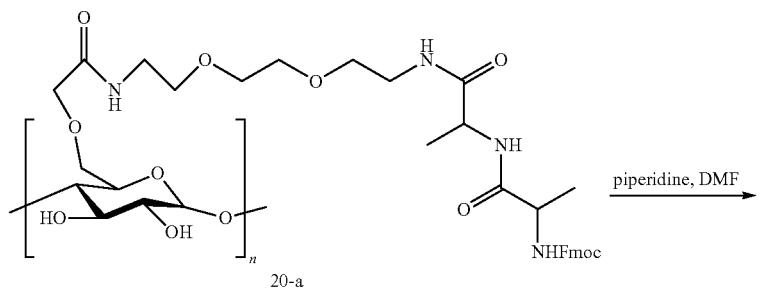

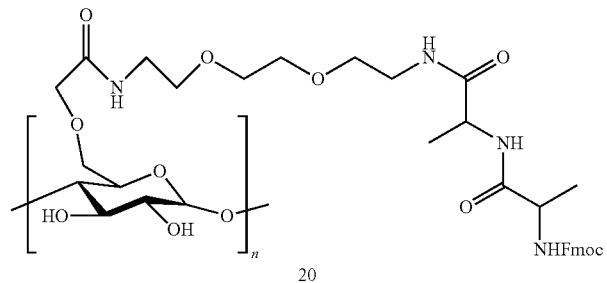

Polymer 19 (200 mg, 0.470 mmol) was ground into a fine powder and mixed with DMF (20 mL) for 20 minutes. Fmoc-Ala-OH (0.439 g, 1.41 mmol), HBTU (0.539 g, 1.41 mmol), EDC (270 mg, 1.41 mmol) and DIPEA (0.018 mL, 1.41 mmol) were added to a large centrifuge tube and purged with nitrogen. A lab rotor was used to facilitate mixing overnight. The solid was filtered and washed with DCM (5×20 mL) and methanol (5×20 mL). The resulting product was dried to provide Polymer 20-a as an off-white powder. Weight=0.1576 g. A positive Kaiser test result indicated incomplete coupling. FTIR: Peaks at 3300 (N—H/O—H), 2900/2850 (C—H), 1748 (amide), 1648 (C=O, amide of coupled product), 1584 (C=O of CMC), 1542 ( ) 1445/1403/1022, 899.

Polymer 20-a (158 mg) was placed in a solution of piperidine: DMF (20:80 v/v), (20 mL) and purged with nitrogen gas and stirred for 1 hour, after which the solid was filtered and washed with ethanol (3×50 mL) and DCM (3×50 mL). This process was then repeated, and the product was dried to provide Polymer 20 as an off-white powder. Weight=0.1391 g (58% yield). A positive Kaiser test result confirmed presence of free amine. FTIR: Peaks at 3300 (N—H/O—H), 2900/2850 (C—H), 1748 (amide), 1648 (C=O, amide of coupled product), 1584 (C=O of CMC), 1403/1025, 900.

Example 21: Preparation of Polymer 21

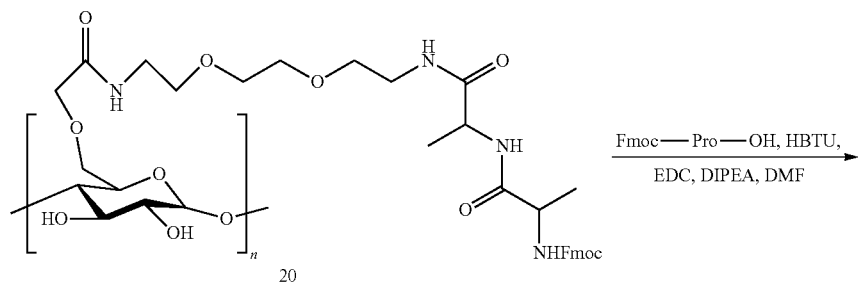

20

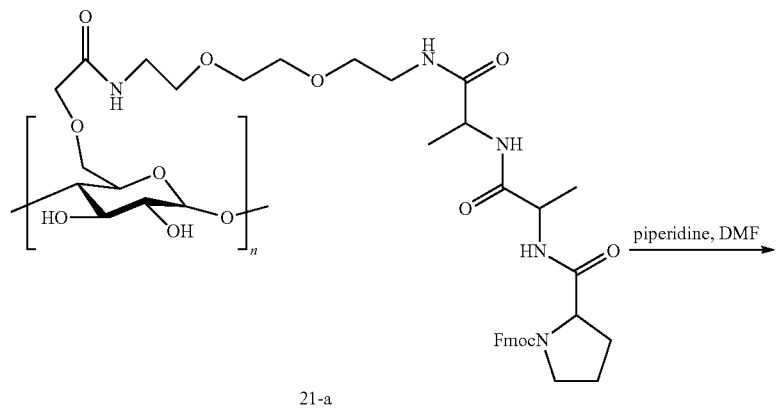

21-a

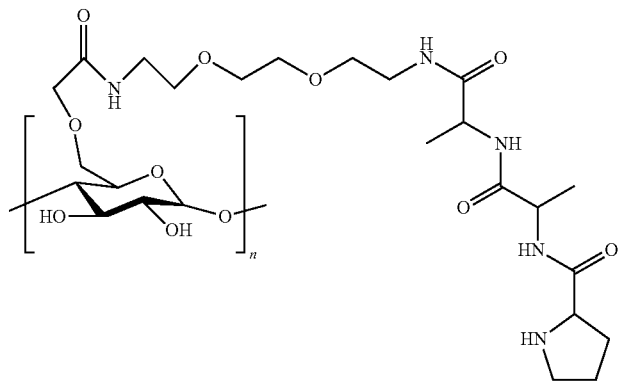

21

Polymer 20 (150 mg, 0.2785 mmol) was ground into a fine powder and mixed with DMF (20 mL) for 20 minutes. Fmoc-Pro-OH (0.282 g, 0.836 mmol), HBTU (0.317 g, 0.8356 mmol), EDC (160 mg, 0.836 mmol) and DIPEA (0.20 mL, 0.836 mmol) were added to a filtration column tube and sealed. A lab rotor was used to facilitate mixing overnight. The solid was filtered and washed with DCM (5×20 mL) and methanol (5×20 mL). The resulting product was dried to provide Polymer 21-a as an off-white powder. Weight=0.10967 g. A positive Kaiser test result indicated presence of unreacted amine. FTIR: Peaks at 3300 (N—H/O—H), 2850 (C—H), 1748 (amide), 1648 (C=O, amide of coupled product), 1584 (C=O of CMC), 1403/1025.

Polymer 21-a (100 mg) was placed in a solution of piperidine: DMF (20:80 v/v), (20 mL) and stirred for 1 hour, after which the solid was filtered and washed with ethanol (3×50 mL) and DCM (3×50 mL). This process was then repeated, and the product was dried to provide Polymer 21 as an off-white powder. Weight=0.08020 g (47% yield). A positive Kaiser test result indicated presence of free amine. FTIR: Peaks at 3300 (N—H/O—H), 2850 (C—H), 1748 (amide), 1648 (C=O, amide of coupled product), 1584 (C=O of CMC), 1453/1403/1024, 962/906/841.

Example 22: Preparation of Polymer 22

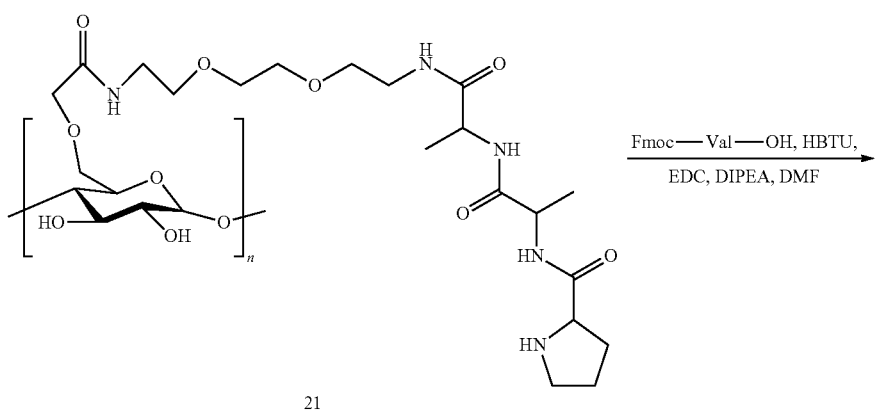

21

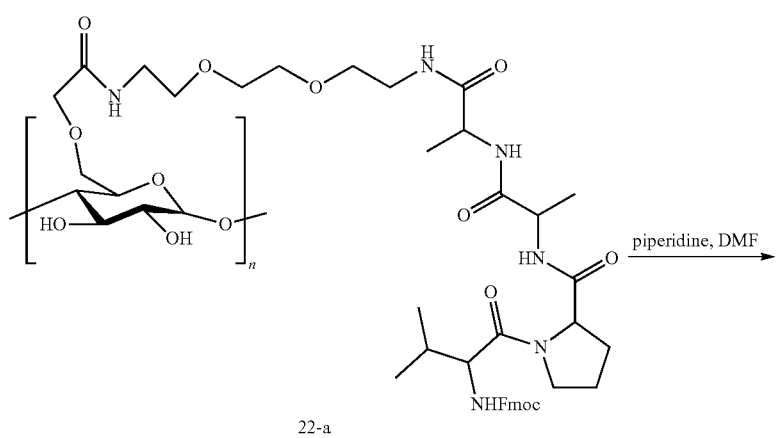

22-a

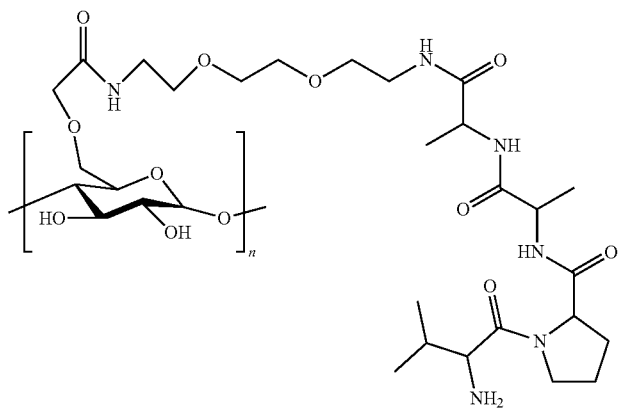

22

Polymer 21 (100 mg, 0.165 mmol) was ground into a fine powder and mixed with DMF (10 mL) for 20 minutes. Fmoc-Val-OH (0.167 g, 0.494 mmol), HBTU (0.187 g, 0.494 mmol), EDC (95 mg, 0.494 mmol) and DIPEA (0.064 mL, 0.494 mmol) were added to a filtration column tube and sealed. A lab rotor was used to facilitate mixing overnight. The solid was filtered and washed with DCM (5×20 mL) and methanol (5×20 mL). The resulting product was dried to provide Polymer 22-a as an off-white powder. Weight=0.0603 g. A positive Kaiser test result indicated presence of unreacted amine.

Polymer 22-a (60 mg) was placed in a solution of piperidine: DMF (20:80 v/v), (20 mL) and stirred for 1 hour, after which the solid was filtered and washed with ethanol (3×50 mL) and DCM (3×50 mL). This process was then repeated, and the product was dried to provide Polymer 22 as an off-white powder. Weight=0.0553 g (48% yield). A positive Kaiser test result indicated presence of free amine. FTIR: Peaks at 3300 (N—H/O—H), 2850 (C—H), 1748 (amide), 1648 (C=O, amide of coupled product), 1585 (C=O of CMC), 1453/1403/1024/1095/1058, 961, 841.

Example 23: Preparation of Polymer 23

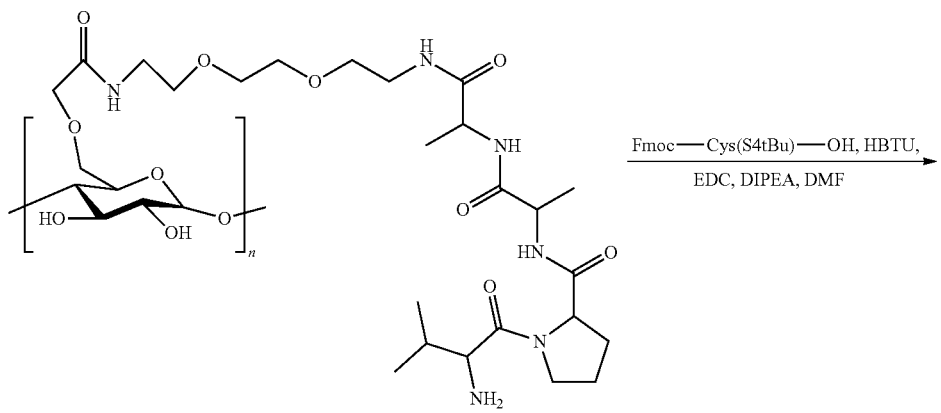

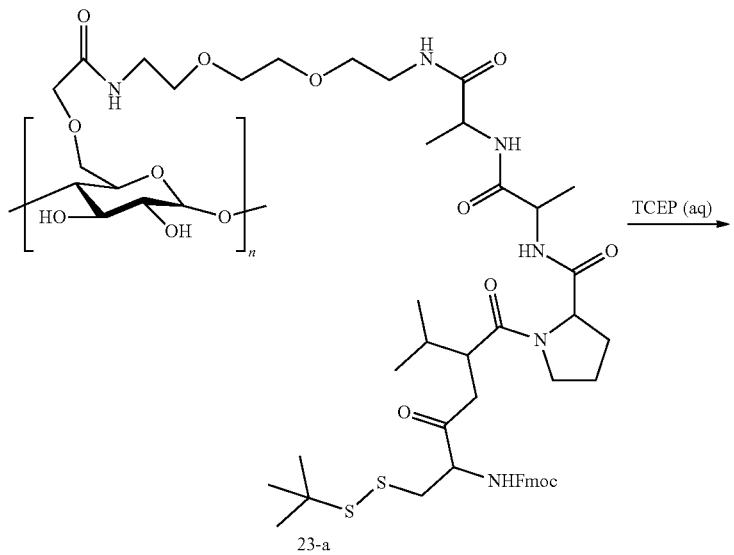

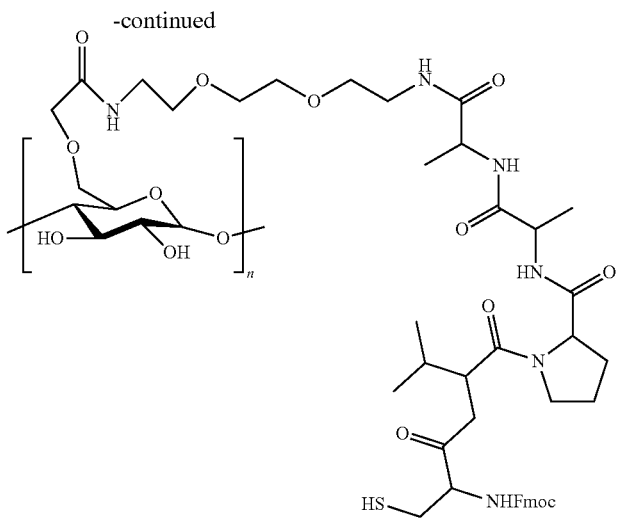

23

Polymer 22 (50 mg, 0.707 mmol) was ground into a fine powder and mixed with DMF (10 mL) for 20 minutes. Fmoc-Cys(StBu)-OH (716 mg, 2.122 mmol), HBTU (805 mg, 2.122 mmol), EDC (407 mg, 2.122 mmol) and DIPEA (0.274 mL, 2.122 mmol) were added to a filtration column tube and sealed. A lab rotor was used to facilitate mixing overnight. The solid was filtered and washed with DCM (5×20 mL) and methanol (5×20 mL). The resulting product was dried to provide Polymer 23-a as an off-white powder. Weight=0.0253 g. A positive Kaiser test result indicated presence of unreacted amine. FTIR: 3300 (N—H/O—H), 2850 (C—H), 1748 (amide), 1648 (C=O, amide of coupled product), 1585 (C=O of CMC), 1453/1403/1024/1095/1058, 961, 841.

Polymer 23-a (25 mg) was placed in a solution of TCEP in water (5 mL) and stirred for 2 hours at RT, after which the solid was filtered and washed with ethanol (3×50 mL) and DCM (3×50 mL). This process was then repeated, and the product was dried to provide Polymer 23 as off-white powder. A positive Kaiser test result indicated presence of free amine. This material was used in Example 24 without additional characterization.

Example 24: Preparation of Polymer 24

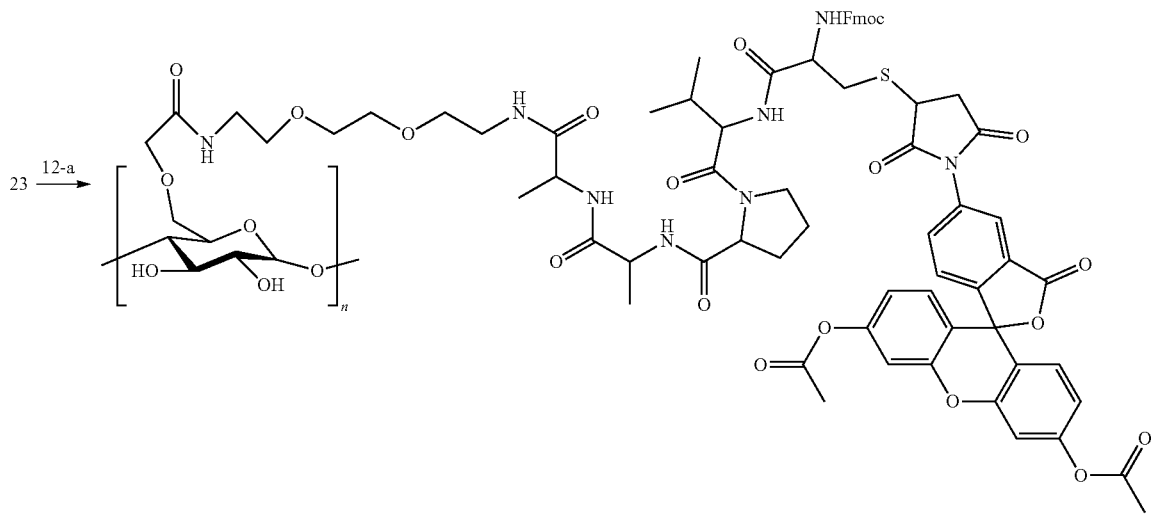

TCEP (0.0357 g, 0.125 mmol, 4 equiv) was dissolved in 1 mL water and added to polymer 23 (25.3 mg, 0.0312 mmol), and the mixture was stirred at RT for 30 min. The solid was filtered and washed with water (10 mL×3) and freeze-dried yielding solid off-white/cream colored powder which was then washed with the DMF (10 mL×3).

Fluoresceindiacetate-5-maleimide (compound 12-a) (0.016 g, 0.0312 mmol, 1 equivalent) was dissolved in 3 mL dry DMF and was added to the pre-treated polymer 23 which had been purged with $N_2$ (g). The reaction was stirred at RT overnight covered with foil to protect from the light. A lab rotor was used to facilitate mixing overnight. The solid was filtered and washed with DCM (5×20 mL) water (5×20 mL) and methanol (5×20 mL). The resulting product was dried to provide Polymer 24 as an off-white powder. Weight=0.0156 g (32% yield). FTIR: (vmax/cm') 3286 (N—H/O—H), 2872 (C—H), 1722 (Acetone), 1647 (C=O, amide of coupled product), 1589 (C=O of CMC), 1545 (C—C Ar. fluorescein), 1409/1317/1250/1024/894. $^{13}$C CP MAS NMR: CMC 0.7 DoS (starting material): δ C (13,000 Hz, CP MAS) 61.7 (C6), 74.5 (C7, C2, C5), 82.5 (shoulder, C3), 97.0 (C4), 103.3 (C1), 177 (C=O); CMC-PEG di-amine: δ C (13,000 Hz, CP MAS) 13.4 (C14), 20.1 (not assigned), 23.4 (not assigned), 30.6 (C9), 61.7 (C6), 70 (shoulder, C7), 74.5 (C2, C5), 82.5 (C3), 95 (C4), 103.3 (C1), 113 (not assigned), 142 (not assigned), 152 (not assigned), 169.7 (C=O of linker), 177.1 (C=O of CMC).

Example 25: Preparation of Polymer 25 (fiber)

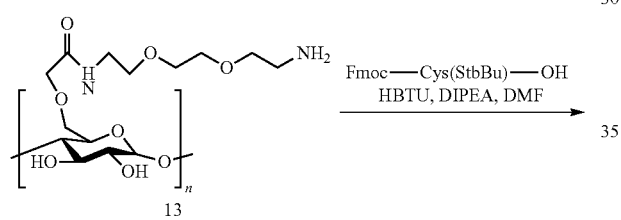

Polymer 13 was mixed with DMF (30 mL) for 20 min. Fmoc-C(StBu)-OH (1.5 g, 3.5 mmol), HBTU (3.09 g, 8.14 mmol) and DIPEA (1.05 mL, 8.14 mmol) were added with stirring at RT, open to air (a centrifuge tube and lab rotor were used to facilitate mixing overnight). After rotating overnight, the solid was filtered and washed with DCM (5×50 mL), methanol (5×50 mL) and again with DCM (5×50 mL). The resulting product was dried to provide Polymer 25 and used directly in the next example (Example 26).

Example 26: Preparation of Polymer 26

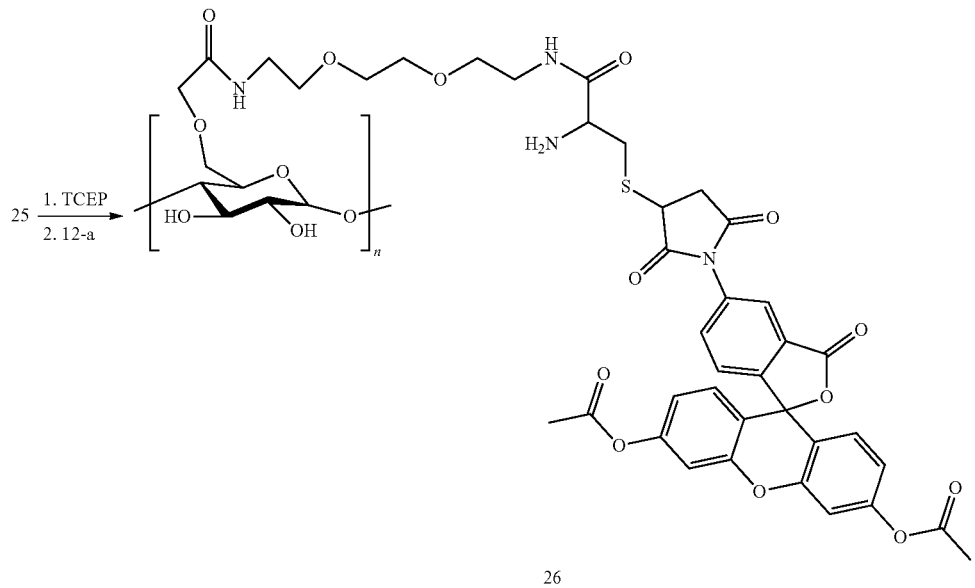

Polymer 26 was prepared using an analogous procedure as described in Example 12. Appearance: off-white, powder/solid. Weight=1.258 g (59% yield). FTIR: 3339 (N—H/O—H), 2872 (C—H), 1736 (Acetone), 1648 (C=O, amide of coupled product), 1549 (C=O of CMC), 1419, 1363, 1313, 1201. δ C (10,000 Hz, CP MAS): 30 (C9, 19), 39 (C10,11, 12,13), 47 (C18, 22), 54 (C16), 60 (C6), 70-74 (broad, C2,3,5,7), 83 (shoulder, C4), 92 (C17), 97, 104 (C1), 120 (C24), 128 (C25,26,27), 142 (C28), 156 (small, C20, C=Ocarbamate), 171 (C8 carbonyl of amide). Elemental analysis: Expected of product if DoS of raw material were 1 and full conversion to linker groups: Mass 781 g mol$^{-1}$: C 55%, H 7%, N 5%, S 8%. Actual: C 46%, H 7%, N 2%, S (not performed). Taking the S aspect and calculating the % N present over the % N possible (2/3.5)=57% coupling of linker groups. Taking the S aspect and calculating the % N present over the % N possible (2/3.5)=57% coupling of linker groups. Therefore of all monomers, ~40% contain the linker group.

Example 27: Preparation of Polymer 27

A solution of aminophenyl fluorescein (5 mg, 0.018 mmol) and HBTU (14 mg, 0.036 mmol) in dry DMF (2.0 mL) was prepared. CMC-PEG-NH2 (5-a) (0.13 mg, 0.036 mmol) was added to the reaction mixture and agitated at RT for approximately 24 hours protected from the light using a foil cover. The product was filtered washed with ethanol (10 mL×3) and DMF (5×10 mL) and subsequently concentrated in vacuo yielding a solid red/orange product (27) (12.0 mg, 43%). FTIR (vmax/cm$^{-1}$) 3367 (N—H/O—H), 2932 (C—H), 1702 (amide of APF), 1655 (CONN, amide of coupled product), 1555 (HNCO, CMC), 1494, 1437, 1413, 1387 (Ar. C=C bending), 1106 (OCHR, alkoxy APF), 838, 759, 722, 557 (ar. CH bending).

Example 28: Preparation of Polymer 28

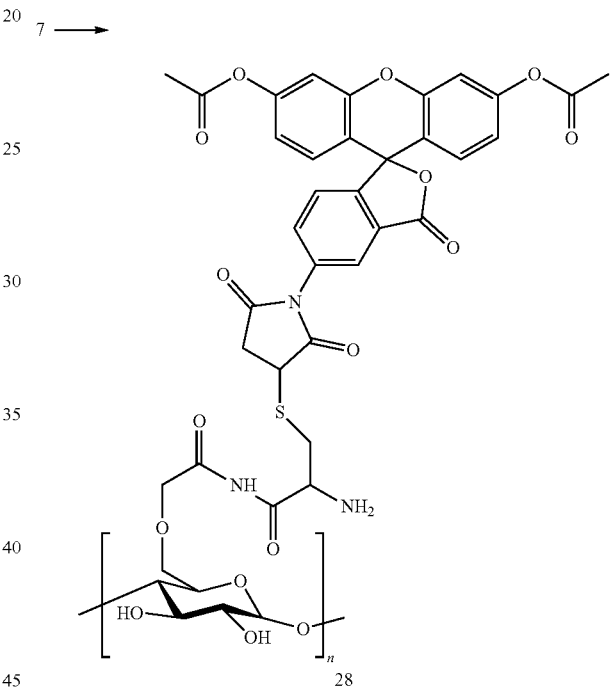

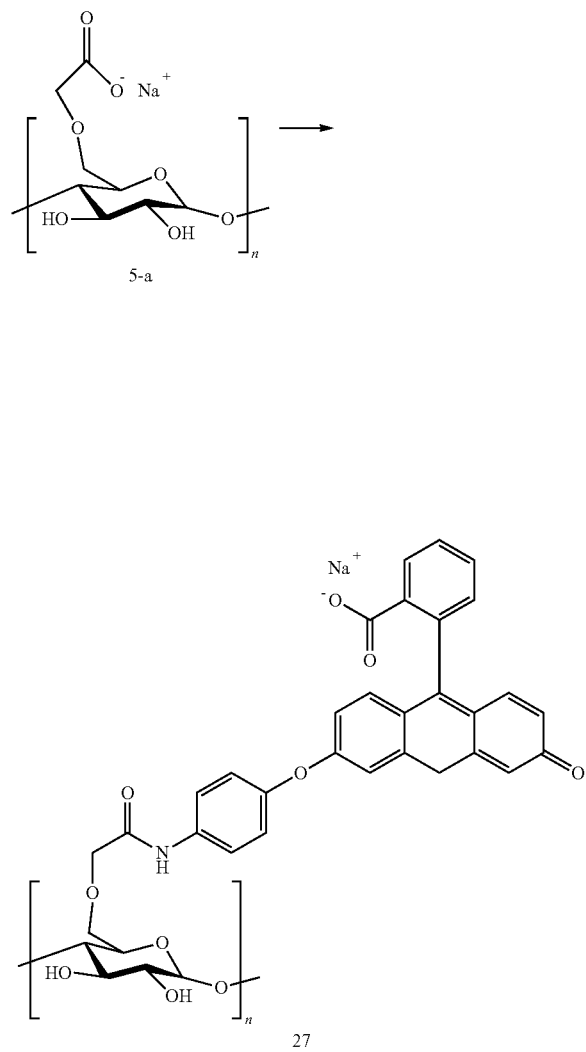

CMC-Cys (7) (10 mg, 0.029 mmol 1eq.) was stirred at RT for 1 hour with TCEP (16.8 mg, 0.058 mmol, 4 eq.) in DI water (1 mL) in order to de-couple any unwanted disulphide bonds. The solid was filtered and washed with water (10 mL×3), freeze-dried and then washed again with DMF (10 mL×3). Fluorescein diacetate-5-maleimide (12-a) (11 mg, 0.029 mmol, 1 eq.) was dissolved in dry DMF (3 mL) and added to the CMC-CYS under a nitrogen atmosphere. The reaction was stirred at RT overnight and was protected from the light. The product was washed with water (3×100 mL) and DMF (1×100 mL) yielding an opaque waxy solid (28) (0.017 g, 85%). FTIR (vmax/cm$^{-1}$) 3365 (β-H), 2971/2910, (N—H, CH) 2883 (SH), 1728 (COOH, acid), 1677 (CONH, amide), 1640 (HNCO, peptide), 1598 (HNCOO, CMC), 1409, 1371 (COO), 1307 (ar. C=C bending), 1216, 1019 (CN, tertiary amine); Solubility insoluble in water, pH9 phosphate buffer and common laboratory solvents (acetone, methanol, ethanol, THF, DCM and DMF).

Example 29: Preparation of Polymer 29

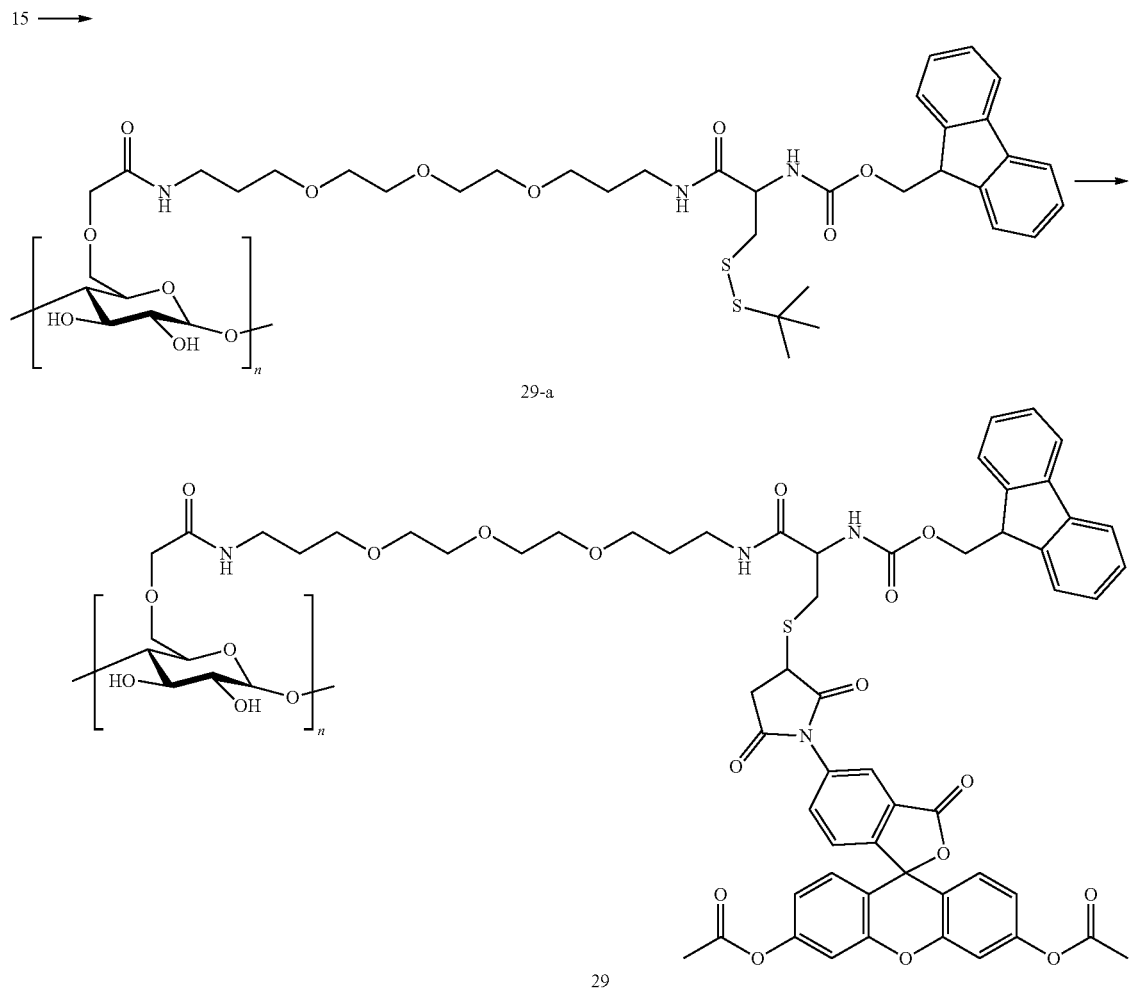

CMC-PEG-NH2 (15) (1.000 g, 2.27 mmol) was ground into a fine powder and mixed with DMF (15 mL) for 20 minutes. Fmoc-C(StBu)-OH (1.14 g, 2.639 mmol, 1.2 eq.), HBTU (2.59 g, 6.8181 mmol) and DIPEA (1.19 mL, 6.8181 mmol) were added with stirring at RT, overnight. The product was filtered and washed with DCM (5×20 mL) and methanol (5×20 mL) and then reduced in vacuo. The protected product was then StBu deprotected, repeating each de-protection step 3 times each before being reduced in vacuo yielding a white solid powder (29-a) (0.236 g, 5%). Solid State 13C NMR (10,000 MHz, CP MAS) 176.52 (C-8 of CMC proportion), 171.84 (C-8, C-19), 156.45, 142.32, 127.85-120.08 (C—Ar, Fmoc), 113.93, 103.26 (C-1), 82.60 (C-4), 74.50 (C-2, C-3, C-5), 69.92 (C-7), 61.45 (C-6), 54.93 (C-20), 49.52, 47.30, 41.58, 38.72-23.08 (C-9, C-10, C-11, C-12, C-13, C-14, C-15, C-16, C-17, C-18, C-20); FTIR (vmax/cm$^{-1}$) 3310 (β-H), 2915 (N—H, C—H), 2868 (S—H), 1731 (COOH, acid), 1650 (CONH, amide of coupled product), 1592 (HNCOO, CMC), 1538 (HNCOO, peptide), 1441, 1417, 1361 (COO), 1310 (ar. C=C bending), 1252 (amide CO stretch), 1031 (CN, tertiary amine), 841; EA Expected for deprotected product C:45.3%, H:7.5%, N:4.7%, S:7.1%, found C:47.1%, H:7.8%, N:6.7%, S:10.1% therefore coupling yield is 11%; Solubility insoluble in water and common laboratory solvents (acetone, methanol, ethanol, THF, DCM and DMF), soluble in pH9 phosphate buffer over time; Ellmans Test positive.

Intermediate (29-a) (75.4 mg, 0.147 mmol 3 eq.) was stirred at RT for 1 hour with TCEP (168.5 mg, 0.196 mmol, 4 eq.) in DI water (1 mL) in order to de-couple any unwanted disulphide bonds. The solid was filtered and washed with water (10 mL×3), freeze-dried and then washed again with DMF (10 mL×3). Fluorescein diacetate-5-maleimide (12-a) (25.0 mg, 0.049 mmol, 1 eq.) was dissolved in dry DMF (2 mL) and added to the CMC-PEG-NH—CYS (29-a) under a nitrogen atmosphere. The reaction was stirred at RT overnight and was protected from the light. The reaction mixture was reduced in vacuo, the product was washed five times with water (~75 mL) and freeze-dried yielding an off-white powder (29) (63.0 mg, 44%). Solid State 13C NMR (10,000 MHz, CP MAS) 176.38 (C-8 of CMC proportion), 171.00 (C-8, C-19, C-38), 153.12 (C-22), 141.67, 135.49-, 119.80 (C—Ar, Fmoc, Fluorescein), 102.43 (C-1), 81.92 (C-4), 74.47 (C-2, C-3, C-5), 70.30 (C-7), 68.61, 61.45 (C-6), 46.73 (C-42), 36.47-29.48 (C-9, C-10, C-11, C-12, C-13, C-14, C-15, C-16, C-17, C-18, C-20); FTIR (vmax/cm$^{-1}$)

3315 (β-H), 2911 (N—H, C—H), 2869 (S—H), 1922, 1720 (COOR, conjugated ester, fluorescein), 1647 (CONH, amide of coupled product), 1591 (HNCOO, CMC), 1542 (CONH, peptide), 1420, 1366/1309, (Ar. C=C bending), 1248 (C—O stretching), 1213, 1050 (CN, tertiary amine), 842, 581(ar. CH bending); EA Expected C:51.1%, H:5.8%, N:3.7%, S:2.1%, found C:42.8%, H:7.0%, N:4.0%, S:0.5% therefore coupling yield is 24%.
Example 30: Preparation of Polymer 30 (Fiber)
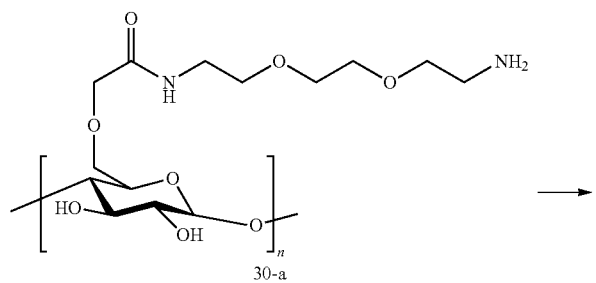
30-a
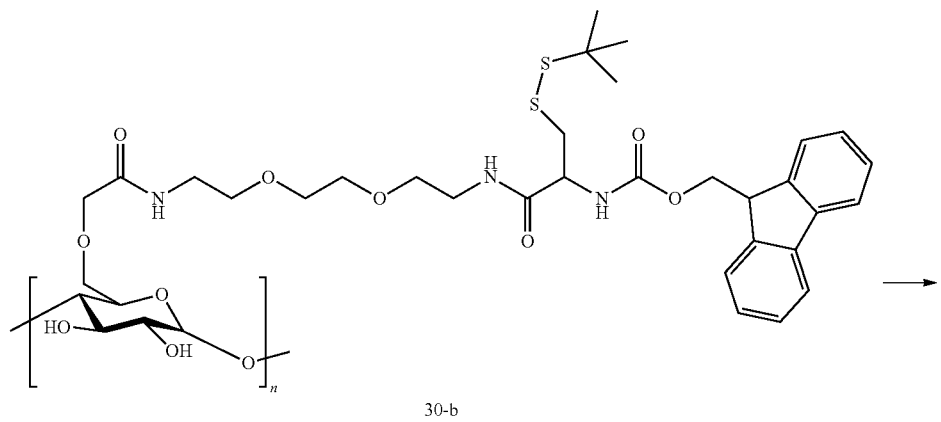
30-b

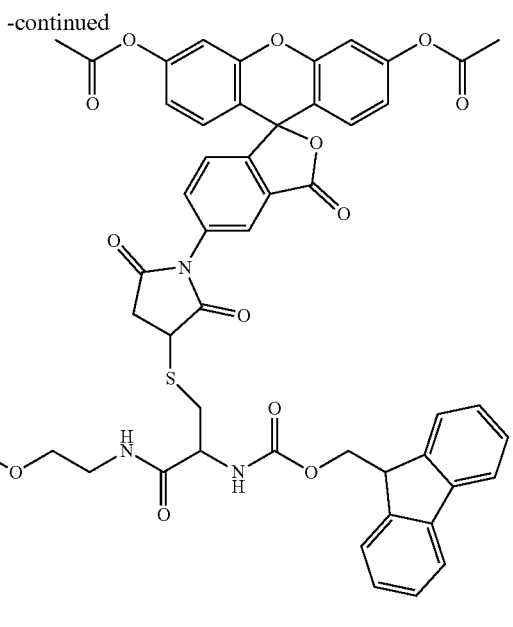

30

NaCMC fibers of DoS 0.3 (2.0 g, 8.33 mmol) were dispersed in a solution of ethanol: de-ionized water (80:20 v/v) (180 mL) to give a 1% suspension. Dowex 650C monosphere ion exchange resin was added with stirring for 30 minutes. The monospheres were removed by filtration before tetrabutylammonium hydroxide (TBAH) 40% (aq) was added in 0.1 mL aliquots until the pH was 8-9 (3.0 mL, 1.16 mmol). The resulting solution was stirred for 30 minutes before being reduced in vacuo. The film-like material was dissolved in dry DMF (100 mL) under a nitrogen atmosphere, stirring and gentle heating was required overnight resulting in a viscous gel-like solution with a uniform texture. The solution was cooled to approx. 4° C. and CMP-I (1.48 g, 5.8 mmol) was added with vigorous stirring. 2,2'-(ethylenedioxy)bis(ethylamine) (1.36 g, 9.17 mmol) was added to the reaction, along with dry triethylamine (3 mL). The reaction was kept at 4° C. and stirred for a minimum of 3 hours, after which the solid was filtered and washed with 99% acetone (3×100 mL) and DCM (3×100 mL), sonication was performed for 1 minute during each wash cycle to encourage the fiber clumps to disentangle and release any contaminant. The product was reduced in vacuo to yield a white fibrous solid (30-a) (1.8 g, 60%). Solid State 13C NMR (10,000 MHz, CP MAS) 176.93 (C-8 of CMC proportion), 171.96 (C-8), 153.41, 142.40, 104.11, (C-1), 96.80, 83.55 (C-4), 74.18 (C-2, C-3, C-5),69.39 (C-7), 61.89 (C-6), 40.48 (Broad, C-10, C-11, C-12, C-13, C-14); FTIR (vmax/cm$^{-1}$) 3325 (β-H), 2872 (N—H, C—H), 1648 (CONH, amide of coupled product), 1589 (HNCOO, CMC), 1543, 1408, 1367 (CHO), 1314, 1265 (amide CO stretch), 1022 (CN, tertiary amine), 896; EA expected C:41.7%, H:7.0%, N:2.3%, found C:42.6%, H:6.3%, N:2.9% therefore coupling yield is 127%; Solubility insoluble in water and common laboratory solvents (acetone, methanol, ethanol, THF, DCM and DMF), soluble in pH9 phosphate buffer and PBS over time; Kaiser Test positive, 3.08μ·mol amine.

CMC-PEG-NH2 in fiber form (30-a) (1.0 g, 2.86 mmol) was mixed with DMF (30 mL) for 20 minutes. Fmoc-C(StBu)-OH (1.5 g, 3.5 mmol), HBTU (3.09 g, 8.14 mmol) and DIPEA (1.10 mL, 8.57 mmol) were added with stirring at RT, overnight. The product was filtered and washed with DCM (5×50 mL), methanol (5×50 mL), again with DCM (5×50 mL) and then reduced in vacuo yielding a white solid powder (30-b) (1.23 g, 59%). NOTE: The protected product was not Fmoc or StBu deprotected at this stage. Solid State 13C NMR (10,000 MHz, CP MAS) 176.38 (small peak, C-8 of CMC proportion), 171.93 (C-8, C-15), 156.28 (C-20), 141.73, 127.61-120.01 (C—Ar, Fmoc), 104.17 (C-1), 96.81, 87.27, 82.86 (C-4), 74.29 (C-2, C-3, C-5), 69.17 (C-7), 62.17 (C-6), 60.00 (C-21), 54.22 (C-16), 46.87 (C-22), 46.87, 39.36-29.49 (C-10, C-11, C-12, C-13, C-14, C-17, C-19); FTIR (vmax/cm$^{-1}$) 3339 (β-H), 2872 (N—H, C—H), 1736 (COOH, acid), 1648(CONH, amide of coupled product), 1549 (HNCOO, CMC), 1419, 1363 (COO), 1201, 1031 (CN, tertiary amine), 841; EA expected C:44.6%, H:6.7%, N:1.6%, S:2.5%, found C:46.0%, H:6.5%, N:2.2%, S: not enough material available; Solubility insoluble in water and common laboratory solvents (acetone, methanol, ethanol, THF, DCM and DMF), soluble in pH9 phosphate buffer over time; Ellmans Test positive.

CMC-PEG-Cys(Fmoc)StBu in fiber form (30-b) (0.5965 g, 1.265 mmol) was stirred at RT for 30 min with TCEP (1.45 g, 5.060 mmol, 4 eq.) in DI water (3 mL) in order to de-couple any unwanted disulphide bonds. The solid was filtered and washed with water (10 mL×3), freeze-dried and then washed again with DMF (10 mL×3). Fluorescein diacetate-5-maleimide (12-a) (0.125 g, 0.240 mmol, 1eq.) was dissolved in dry DMF (15 mL) and added to the CMC-PEG-NH—CYS under a nitrogen atmosphere. The reaction was stirred at RT overnight and was protected from the light. The reaction mixture was reduced in vacuo, the product was washed with DCM (3×50 mL), Methanol (3×50 mL) and reduced in vacuo. The off-white solid fibers were then washed with water (5×75 mL) with gentle heating, stirring and sonication before being filtered and lyophilised yielding off-white solid fibers (30) (1.10 g, 72%). Solid State 13C NMR (10,000 MHz, CP MAS) 174.88 (C-8 of CMC proportion), 172.30 (C-8, C-15, C-34), 141.36, 129.34-126.65 (C—Ar, Fmoc, Fluorescein), 104.58 (C-1), 86.94, 82.52 (C-4), 78.56-72.96 (C-2, C-3, C-5, C-7), 69.74, 61.45, 60.35 (C-6), 38.69-21.02 (C-9, C-10, C-11, C-12, C-13, C-14); FTIR (vmax/cm$^{-1}$) 3315 (β-H), 2868 (N—H, C—H), 1728 (COOR, conjugated ester, fluorescein), 1647 (CONH, amide of coupled product), 1542 (CONH, amide of peptide coupling, NHCOO CMC), 1419, 1364 (Ar. C=C bending), 1264 (C—O stretching), 1152 (OCHR), 1018 (CN tertiary amine), 879; EA expected C:50.9%, H:6.9%, N:5.5%, 5:1.0%; found C:30.8%, H:8.6%, N:1.3%, S: <0.3% therefore coupling yield is 24%.

Example 30: Preparation of Polymer 31

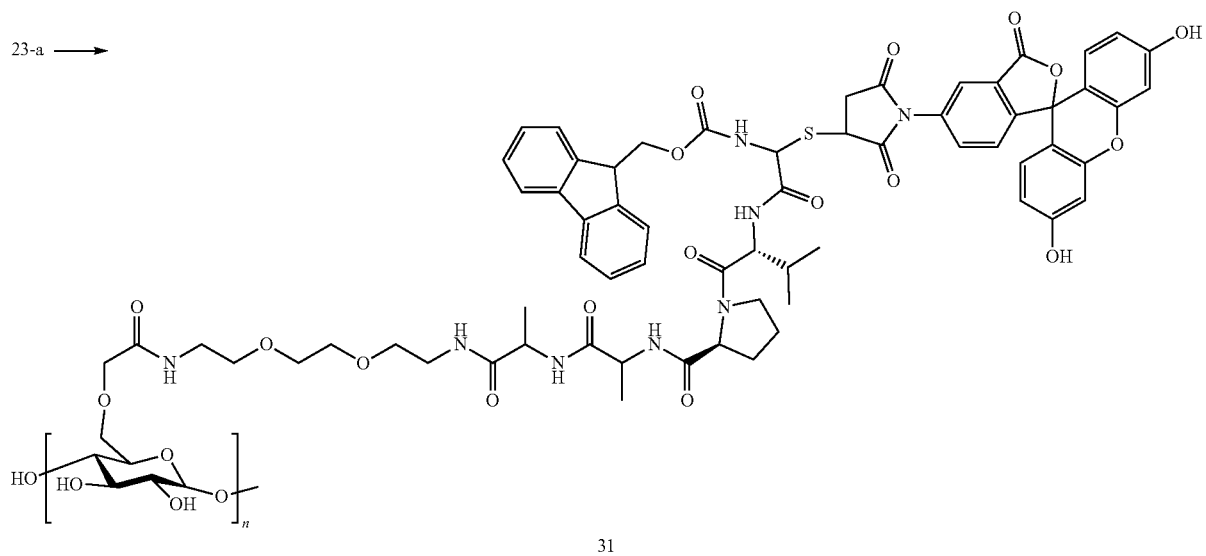

31

CMC-PEG-NH-AAPVC(Fmoc)StBu in powder form (23-a) (525 mg, 439 mmol) was stirred at RT for 30 min with TCEP (503.4 mg, 0.1756 mmol, 4 eq.) in DI water (23 mL) in order to de-couple any unwanted disulphide bonds. The solid was filtered and washed with water (50 mL×3), methanol (50 mL×3), ethanol (50 mL×3) and then again with water (50 mL×3), it was then freeze-dried and then washed again with DMF (50 mL×3). Fluorescein-5-maleimide (25 mg, 59 mmol, 0.1 eq.) was dissolved in dry DMF (70 mL) and added to the CMC-PEG-NH-AAPVC(Fmoc) under a nitrogen atmosphere. The reaction was stirred at RT for 3 hours and was protected from the light. The reaction mixture was reduced in vacuo, the product was washed with DCM (3×50 mL), methanol (3×50 mL), DI water (3×50 mL), again with DCM 3×50 mL) and again with methanol (3×50 mL) and methanol (3×50 mL) and reduced in vacuo yielding an off-white solid (31) (436 mg, 68%). Solid State 13C NMR (10,000 MHz, CP MAS) 176.70 (C-8 of CMC proportion, C-39, C-41), 171.39 (C-8, C-15, C-18, C-21, C-26, C-30, C-45), 153.37 (C-33, C-51), 142.19 (C-36, C-37, C—Ar), 127.57-120.48 (C—Ar), 103.85, (C-1), 102.63 (C—Ar), 97.55, 82.31 (C-4), 74.34 (C-2, C-3, C-5, C-7), 69.85 (C-23), 60.80 (C-6, C-27), 52.23-48.37 (C-16, C-19, C-25, C-35), 42.10 (C-9, C-14, C-38), 38.70-25.05 (C-9, C-10, C-11, C-12, C-13, C-14), 18.45 (C-17, C-20, C-29), 14.11; FTIR (vmax/cm$^{-1}$) 3340/3294 (β-H), 2914/2862 (N—H, C—H), 1737 (COOH, acid), 1645 (CONH, amide of coupled product/COOR, conjugated ester, fluorescein), 1593 (HNCOO, CMC), 1543 (CONH, peptide), 1414, 1375 (COO), 1343 (ar. C=C bending), 1262 (C—O stretching), 1230, 1056 (CN, tertiary amine/OCHR), 897, 841, 764, 556 (ar. CH bending); EA expected C:53.4%, H:6.0%, N:5.4%, S:1.5%, found C:47.1%, H: 6.7%, N: 4.1%, S: 0.8% therefore coupling conversion is 52%.

Example 32: Preparation of Polymer 32

23-a ⟶

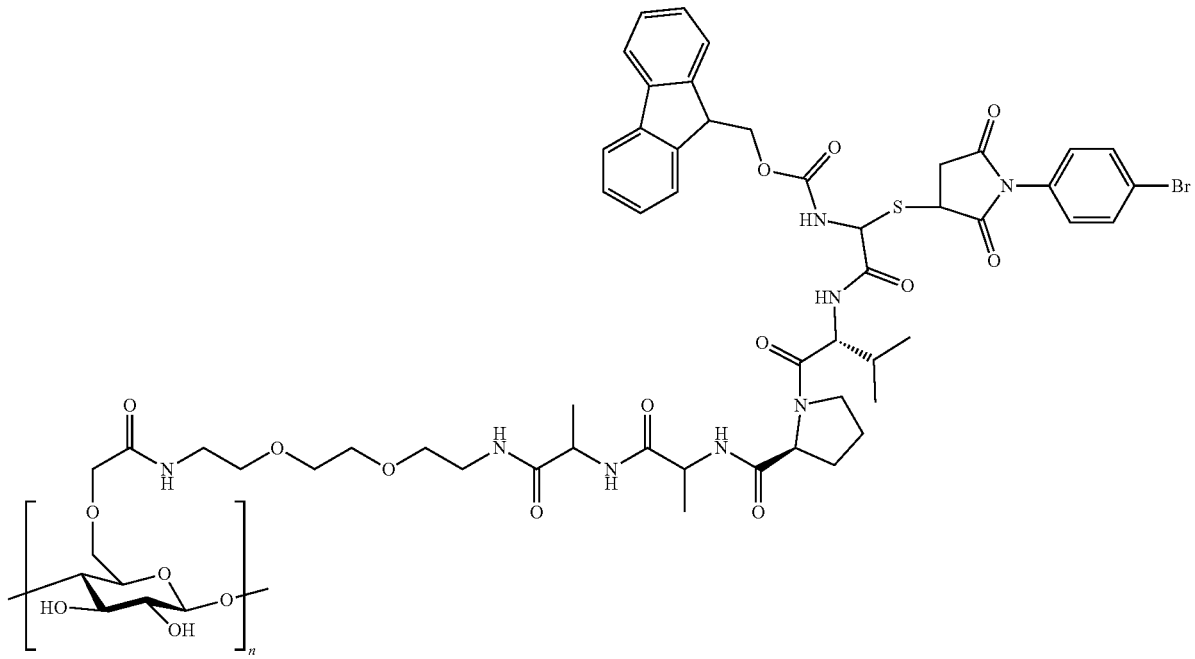

32

CMC-PEG-NH-AAPVC(Fmoc)StBu in powder form (23-a) (175 mg, 146 mmol) was stirred at RT for 30 min with TCEP (168 mg, 585 mmol, 4 eq.) in DI water (23 mL) in order to de-couple any unwanted disulphide bonds. The solid was filtered and washed with water (50 mL×3), methanol (50 mL×3), ethanol (50 mL×3) and then again with water (50 mL×3), it was then freeze-dried and then washed again with DMF (50 mL×3). N-Bromophenyl Maleimide (37 mg, 0146 mmol, 1eq.) was dissolved in dry DMF (20 mL) and added to the CMC-PEG-NH-AAPVC(Fmoc) under a nitrogen atmosphere. The reaction was stirred at RT for 3 hours and was protected from the light. The reaction mixture was reduced in vacuo, the product was washed with DCM (3×50 mL), methanol (3×50 mL), DI water (3×50 mL), again with DCM 3×50 mL) and again with methanol (3×50 mL) and methanol (3×50 mL) and reduced in vacuo yielding an off-white solid (32) (129 mg, 69%). Solid State 13C NMR (10,000 MHz, CP MAS) 171.16 (C-8, C-15, C-18, C-21, C-26, C-30, C-38, C-39), 153.33 (C-32), 142.03, 127.45-113.03 (C—Ar, Fmoc, Fluorescein), 102.74 (C-1), 97.09, 82.15 (C-4), 74.39 (C-2, C-3, C-5, C-7), 69.84, 61.21, 57.42 (C-6, C-31), 47.91 (C-16, C-19, C-27), 38.76-22.56 (C-9, C-10, C-11, C-12, C-13, C-14) 18.33-14.16 (C-17, C-20, C-29); FTIR (vmax/cm$^{-1}$) 3322 (β-H), 2901/2872 (N—H, C—H), 2103, 1788 (COOH, acid), 1644 (CONH, amide of coupled product/COOR, conjugated ester, fluorescein), 1594 (HNCOO, CMC), 1544/1514 (CONH, peptide), 1349/1304 (ar. C=C bending), 1251 (C—O stretching), 1230, 1025 (CN, tertiary amine/OCHR), 898, 843, 738, 556 (ar. CH bending); EA expected C:50.0%, H:6.1%, N:6.1%, S:1.8%, Br: 4.3% found C:46.3%, H: 6.7%, N: 5.2%, S: 0.33%, Br: none detected, therefore coupling conversion is 17%.

Example 33
Protease/Enzyme Cleavage of Peptides

The activity of wound specific proteases, including other proteases such as trypsin, chymotrypsin and thermolysin was assayed. Trypsin cleaves P1-P1' wherein P1 is Lys or Arg, and P1' is non-specific (except when followed by proline). Chymotrypsin cleaves P1-P1' wherein P1 is any aromatic amino residue, Trp, Tyr or Phe, and P1' is non-specific. Thermolysin is a metalloendopeptidase which cleaves P2-P1-P1'-P2' wherein P1 is non-specific, P1' is Leu, Phe, Ile, Val, Met, Ala and P2' is not Pro.

Esterases hydrolyze the ester linkages of carboxylic acid esters and it therefore behaves differently to proteases, which specifically hydrolyze amino acid sequences. The substrate used for enzymatic assays is CMC-PEG-NH-Phe-Phe-Lys (Dabsyl) and the enzymatic activity was determined using a UV-visible based method. The Phe-Phe-Lys (Dabsyl) sequence should be hydrolyzed by chymotrypsin. Trypsin, was used as a negative control since it should not cleave this sequence.

The activity of the enzymes on the substrate CMC-PEG-NH-Cys-maleimide fluorescein diacetate was analyzed using confocal fluorescence microscopy. The solid particles were first viewed alone and then after the addition of esterase solution (~50 units/mL). The microscopy images demonstrate the increase in fluorescence observed when the enzyme solution was added to the sample. The advantage of using this method is that one can visualize the particles and observe a difference in the fluorescence intensity on addition of an enzyme solution, which confirmed the coupling of the fluorescein diacetate to the CMC polymer. Alternately, multi-plate readers may be used to assess the cleavage of the substrates and the results quantified with Michaelis-Menton kinetics.

In one experiment, the effect of esterase on CMC-PEG-NH-Cys-maleimide-fluorescein diacetate powder was measured. First, CMC-PEG-NH-Cys-maleimide-fluorescein diacetate powder, (0.2 mg) was dispersed in PBS (320 µL). Sonication, vortex mixing and gentle heating were required in order to disperse the compound. 40 µL of substrate suspension was added to the wells of a 96-well plate, then either weak esterase solution (58 U/mL), strong esterase solution (116 U/mL) or PBS (negative control) was added (40 µL per well). A cycle period of 5 minutes over 2 hours was selected for fluorescence measurements.

It was of interest to use two different strengths of esterase solution so that any difference in rate of reaction could be analyzed. The change in fluorescence intensity was calculated by deducting the zero time-point reading (baseline) from each subsequent time-point.

Increased fluorescence was observed in samples incubated with weak (58 U/mL) and strong (116 U/mL) esterase solutions, which increased over time. The strong esterase solution showed an increase of 3.5 times the rate of the weak esterase solution before it reached saturation point at around 30 mins (intensity of 45000 units).

Effect of Spacer Length

In order to investigate the effect of a longer PEG chain length on the esterase assay, fluorescence measurements were recorded for 77 (CMC-'longer' PEG-NH-Cys (Fmoc)-maleimide fluorescein diacetate). In this test, 4 replicates were performed per sample and cycles of one minute over a time period of two hours were recorded. As with the shorter substrate, incubating the longer substrate (77) with the esterase lead to detection of fluorescence. The 116 U/mL (strong) esterase samples peaked after 40 minutes; the 58 U/mL (weak) esterase samples peaked after 80 minutes. The rate of the 116 U/mL esterase reaction was twice that of the 58 U/mL sample, therefore doubling the enzyme concentration caused a doubling of the rate. The rates of reaction were significantly lower than that of the shorter PEG linker equivalent. This reduction was expected since the loading of the peptide onto the CMC was lower.

Incubating the fiber format CMC-PEG-NH-Cys(Fmoc)-maleimide fluorescein diacetate (82) with esterase also generates similar results, wherein both esterase solutions (58 and 116 U/mL) lead to increased fluorescence with time and greater rate of generation of the fluorescent products at greater enzyme concentrations.

Cleavage of CMC-PEG-NH-AAPVC-maleimide fluorescein (powder, alginate fibre & hydrocolloid form) with elastase: the AAPV peptide sequence is a substrate for elastase, with predicted cleavage sites at P1 of Ala and Val. For the compounds which contained this AAPV sequence, an elastase assay was performed in a similar manner to the esterase assays. Three forms of substrates were tested: (a) powder form; (b) wet spun alginate with the compound in fiber format, and (c) hydrocolloid gel containing either 0.8% or 8% of the compound.

Incubation of the compound alone with elastase showed a clear increase in fluorescence over time. The same experiment was also performed to assess the effect of adding elastase solution on a hydrocolloid gel with 0.8% and 8% loading of CMC-PEG-NH-AAPVC-maleimide fluorescein, powder format. The results showed an increase in fluorescence over time for the modified CMC loaded hydrocolloid gels when compared to the control (hydrocolloid gel alone). The higher loading level (8%) was considerably more fluorescent than the lower loading (0.8%) sample. Two different enzyme strengths were tested; in this case there was only a slight increase in the fluorescence of samples when the strong elastase solution (0.5 mg/mL) was used compared to the weak elastase solution (0.1 mg/mL). This suggests that elastase was in excess even at 0.1 mg/mL and that use of modified CMC has a more significant effect on the fluorescence response.

LC-MS analysis of Cleaved Fragments

An experiment was set up in attempt to characterize the fragments produced when adding elastase to CMC-PEG-NH-AAPVC-maleimide fluorescein, powder format. Elastase (0.5 mg/mL in PBS) was added to 78 and incubated at 37° C.; aliquots were collected over several time-points (1 minute to 3 hours) and were preserved by immediately freezing in liquid nitrogen. HPLC was performed on each defrosted aliquot to separate the fragments and then mass spectrometry was performed to analyze their mass. The analysis confirmed the presence of the expected fragments cleaved during incubation with elastase. As predicted, cleavage sites were at P1 of Ala and Val. In addition there was some evidence of Pro fragments, this would suggest that an additional cleavage site at the P1 position of Pro. This result is in line with the increase in fluorescence recorded during the fluorimeter assays and further builds the evidence that the system is able to detect specific enzymes and give a detectable signal.

Example 34

Cell Studies—Biocompatibility of Medical Devices

An important aspect to consider when designing a medical device is its biological safety and other factors such as cytotoxicity, sensitization, hemocompatibility, pyrogenicity, implantation, genotoxicity, carcinogenicity, reproductive and developmental toxicity, biodegradation, etc. The study of the interactions between new materials and cells grown in-vitro can give a good indicator of the toxicity of these materials, and therefore an array of these methods are used (Eisenbrand et al., *Food Chem. Toxicol.* 2002, 40, 193-236). A suitable cell type must be selected in order to make the test appropriate for the area of the body and function related to the device's end use. The method may be quantitative or purely visual, and modern techniques allow a sophisticated viewpoint of cell interactions, such as the use of time-lapse video imaging of cells via a microscope.

Cells of Relevance to Wound Healing: fibroblast cells are important in the wound healing process. They begin to migrate towards the wound bed approximately 24 hours after the injury during the late stages of the inflammatory phase. They modify the wound environment throughout the proliferation and epithelialisation phases by production of mediators including proteases like the MMPs. Finally fibroblast levels reduce back to normal levels at the remodeling stage and once the new wound extracellular matrix has achieved sufficient strength (Bainbridge et al., *J. Wound Care* 2013, 22, 407-408). Fibroblasts are therefore a suitable cell line to use when mimicking the wound healing process.

In vitro Methodology Used: two in vitro cell methods were used in order to screen the peptide modified CMC materials for an initial idea of their biocompatibility.

Source and Culture of Human Dermal Fibroblasts: human dermal fibroblasts had previously been isolated and stored under appropriate conditions.

Cultures of normal fibroblasts had been obtained with informed consent from patients. Patients with diabetes, systemic immunosuppression or with evidence of local infection were excluded from the study. Three patient cell lines were available for this study: Patients A, F and G. A 6 mm biopsy was taken from the patient's thigh. Cultures were established by a single-cell suspension technique following enzymatic degradation of the specimens. Briefly, tissue was incubated overnight with Dispase (2 mg/mL; Boehringer Mannheim, Lewes, UK) to separate epidermal tissue from the dermal tissue. Dermal tissue specimens were then disaggregated overnight utilizing bacterial *Clostridium histolyticum* A collagenase (1 mg/mL; Boehringer Mannheim). Fibroblast cultures were maintained in Fibroblast-Serum Containing Medium (F-SCM) containing Dulbecco's Modified Eagle's Medium (DMEM) supplemented with L-glutamine (2 mM), non-essential amino acids (lx), antibiotics (100 U/mL penicillin G; 100 mg/mL streptomycin sulphate; 0.25 mg/mL amphotericin B) and 1% (v/v) foetal calf serum (FCS). The cultures were maintained at 37° C. in a 5% $CO_2$ humidified atmosphere. At confluency fibroblasts were trypsinized and re-seeded (1.5×105 cells per T75 flask).

Fibroblast Scratch Assay Methodology:

The scratch assay is a technique in which a confluent mono-layer of fibroblasts is grown on a flat surface, then this surface is 'scratched' or 'wounded' to create a channel separating two areas of fibroblast cells. The sample solution is added onto the top of the cells and the channel is monitored over time using confocal microscopy in order to see how the cells respond (Liang et al., *Nat. Protocols* 2007, 2, 329-333). If the surrounding area containing the sample is amenable to cells, the cells will proliferate and migrate to fill the channel during the time-period; if the sample is not amenable then the cells will not migrate and will die.

Human dermal fibroblast cells were seeded into 24-well tissue culture plates (2×104 cells per well), cultured to 80-90% confluence and the monolayers were wounded by scratching along the surface of the tissue culture plastic with a 200 μL pipette tip. Monolayers were washed with PBS and the compounds added at 0.66 mg/mL or 0.066 mg/mL in DMEM. The cells were then re-fed with F-SCM and incubated under standard culture conditions on the motorized, heated and gassed stage of a confocal microscope with Cell-IQ system.

Images were collected every 20 minutes and movies created utilizing the Cell-IQ software. Assays were completed in triplicate for each cell line; Patient A, F and G.

Collagen Matrix Model Methodology:

A collagen matrix model is an in vitro tool which represents the dermis during the reorganization phase of healing. Here, a series of fibroblast populated collagen lattices (FPCLs) were used to compare the peptide modified celluloses against a control in terms of their effect on the reorganization of the collagen matrices. Under normal conditions one would expect to see the FPCLs reduce in diameter due to fibroblast re-organization, which shows that the cellular processes are proceeding as normal and 'healing', can occur (Carlson et al., *Wound Repair Regen.* 2004, 12, 134-147).

Fibroblasts derived from culture by trypsinisation were utilized to construct the fibroblast populated collagen lattices (FPCLs). Type I rat-tail collagen was purchased from First Link. 1.5×105 fibroblasts (in 750 μL F-SCM) were added to 60 mm bacteriological plates containing 2×DMEM (40 parts 10×DMEM, 10 parts NaHCO3 (7.5% (w/v)), 4 parts L-glutamine (200 mM), 4 parts non-essential amino acids (100×), 140 parts H2O and 5 parts NaOH (1 M); 3 mL), 0.1M NaOH (750 μL), FCS (750 μL), 2.25 mL of type I collagen (1.7 mg/mL) and the test compounds (0.66 mg/mL). The plates were incubated at 37° C. for 60 minutes to allow collagen polymerization. They were then detached from the edge of the plate and 2 mL of F-SCM was added. FPCLs were maintained at 37° C. in a 5% $CO_2$ humidified atmosphere.

A circular shape was retained during the FPCL reorganization process, allowing the diameter of the FPCL to be measured at days 3 and 7. For each sample, experiments were performed on cells from three different patient samples (n=3).

Seven modified CMC materials were tested along with CMC powder and CMC fiber as a baseline (Table 3).

TABLE 3

Compounds analyzed during In vitro cell testing

| Compound Description and Number | Form |
|---|---|
| CMC-PEG-NH$_2$, 12 | powder |
| CMC-longer PEG-NH$_2$, 83 | powder |
| CMC-PEG-NH$_2$, 81 | fibre |
| CMC-PEG-NH-Cys-Mal-Fluoresceindiacetate, 74 | fibre |
| CMC-PEG-NH-AAPVC-Mal-Fluorescein, 78 | powder |
| CMC-PEG-NH-AAPVC-Mal-bromophenol, 80 | powder |
| Unmodified CMC | Powder |

Figure 5:
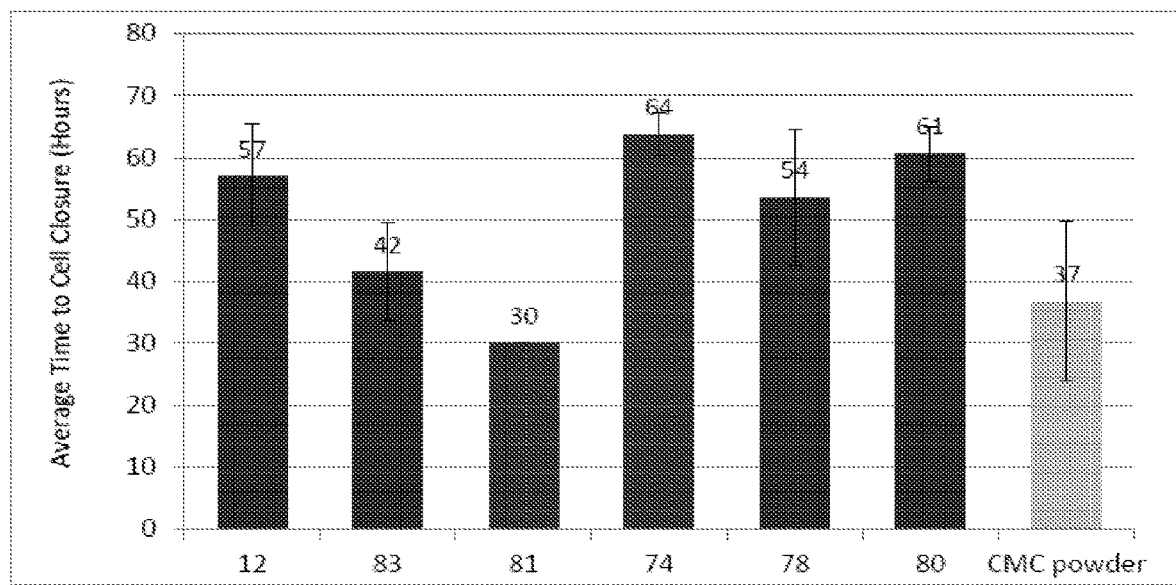
FIG. 5 shows average time to closure during scratch model tests (Error bars show SD) for cell lines from Patients A, F and G. The red bars highlight samples in fiber form; the blue bars represent samples in powder form.
Figure 6A:
FIG. 6A shows fibroblast proliferation as observed at 1 hour based on confocal micrographs for 12, CMC-PEG-NH2 powder, Patient A, 0.066 mg/mL scratch assay. Red dotted lines represent the scratch area, fibroblast proliferation can be observed between T=1 h (no cells present in the channel) and T=68 h (cells fill the channel).
Figure 6B:
FIG. 6B shows fibroblast proliferation as observed at 30 hours based on confocal micrographs for 12, CMC-PEG-NH2 powder, Patient A, 0.066 mg/mL scratch assay. Red dotted lines represent the scratch area, fibroblast proliferation can be observed between T=1 h (no cells present in the channel) and T=68 h (cells fill the channel).
Figure 6C:
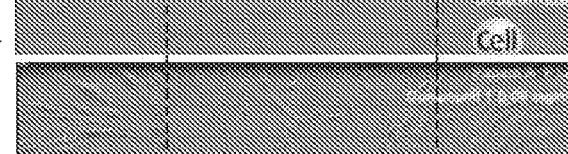
FIG. 6C shows fibroblast proliferation as observed at 50 hours based on confocal micrographs for 12, CMC-PEG-NH2 powder, Patient A, 0.066 mg/mL scratch assay. Red dotted lines represent the scratch area, fibroblast proliferation can be observed between T=1 h (no cells present in the channel) and T=68 h (cells fill the channel).
Figure 6D:
FIG. 6D shows fibroblast proliferation as observed at 68 hours based on confocal micrographs for 12, CMC-PEG-NH2 powder, Patient A, 0.066 mg/mL scratch assay. Red dotted lines represent the scratch area, fibroblast proliferation can be observed between T=1 h (no cells present in the channel) and T=68 h (cells fill the channel).
Figure 7A:
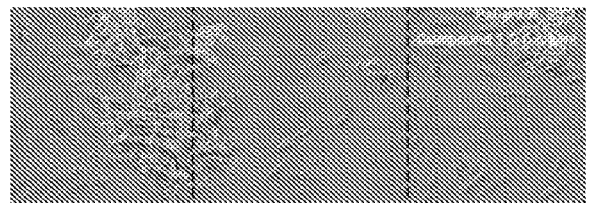
FIG. 7A shows fibroblast proliferation as observed at 1 hour based on confocal micrographs for 12, CMC-PEG-NH2 powder, Patient A, 0.66 mg/mL scratch assay. Red dotted lines represent the scratch area, fibroblast proliferation can be observed between T=1 h (no cells present in the channel) and T=68 h (cells fill the channel).
Figure 7B:
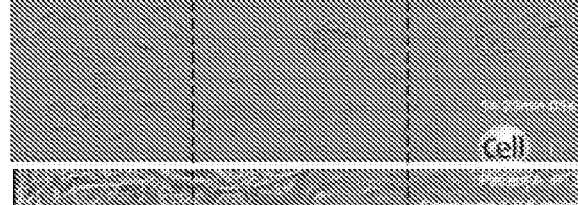
FIG. 7B shows fibroblast proliferation as observed at 30 hours based on confocal micrographs for 12, CMC-PEG-NH2 powder, Patient A, 0.66 mg/mL scratch assay. Red dotted lines represent the scratch area, fibroblast proliferation can be observed between T=1 h (no cells present in the channel) and T=68 h (cells fill the channel).
Figure 7C:
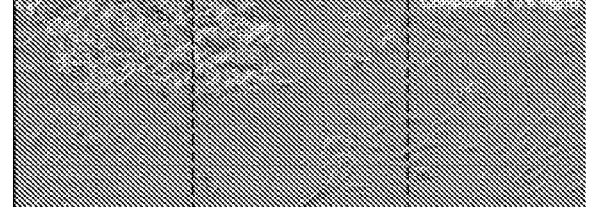
FIG. 7C shows fibroblast proliferation as observed at 50 hours based on confocal micrographs for 12, CMC-PEG-NH2 powder, Patient A, 0.66 mg/mL scratch assay. Red dotted lines represent the scratch area, fibroblast proliferation can be observed between T=1 h (no cells present in the channel) and T=68 h (cells fill the channel).
Figure 7D:
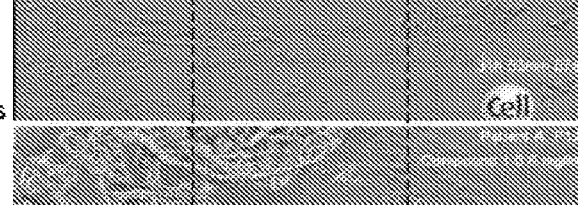
FIG. 7D shows fibroblast proliferation as observed at 68 hours based on confocal micrographs for 12, CMC-PEG-NH2 powder, Patient A, 0.66 mg/mL scratch assay. Red dotted lines represent the scratch area, fibroblast proliferation can be observed between T=1 h (no cells present in the channel) and T=68 h (cells fill the channel).

Results of Fibroblast Scratch Assay:

In general, the fibroblasts remained viable and proliferated to fill the scratch channel during the test period. The results (FIG. 5) show the time taken for the fibroblasts to completely close the scratch channel. As shown in FIG. 5, all samples closed the channel within 70 hours. The CMC powder sample was used as a reference as this is known to be safe for use in wound contact applications. The CMC-PEG-NH2 fiber was the only sample in which the scratch closed in a shorter time period than the control. The CMC-PEG-NH2 powder scratch closure time was roughly equivalent to the other modified CMC samples (~40-60 hours), suggesting that the cells may have some preference for the physical structure of the sample in fiber form.

The scratches for Patient A containing 0.066 mg/mL of 12, CMC-PEG-NH2 powder (FIG. 6) and Patient A containing 0.66 mg/mL of 12, CMC-PEG-NH2 powder (FIG. 7) both closed over time as the fibroblasts replicated and migrated into the channel. These images show that fibroblast cells are not affected by sample insolubility or the higher concentration of sample and are still able to thrive in and around the modified CMC. FIG. 6 and FIG. 7 are representative of the observations of nearly all of the tests performed across all samples and cell lines from patients A, F and G. Although CMC-longer PEG-NH2 powder (#83) generated anomalous results in one study, when the test was repeated with samples obtained from three different patients, the fibroblasts did proliferate and migrate.

Example 35: Collagen Matrix Model

Figure 8:
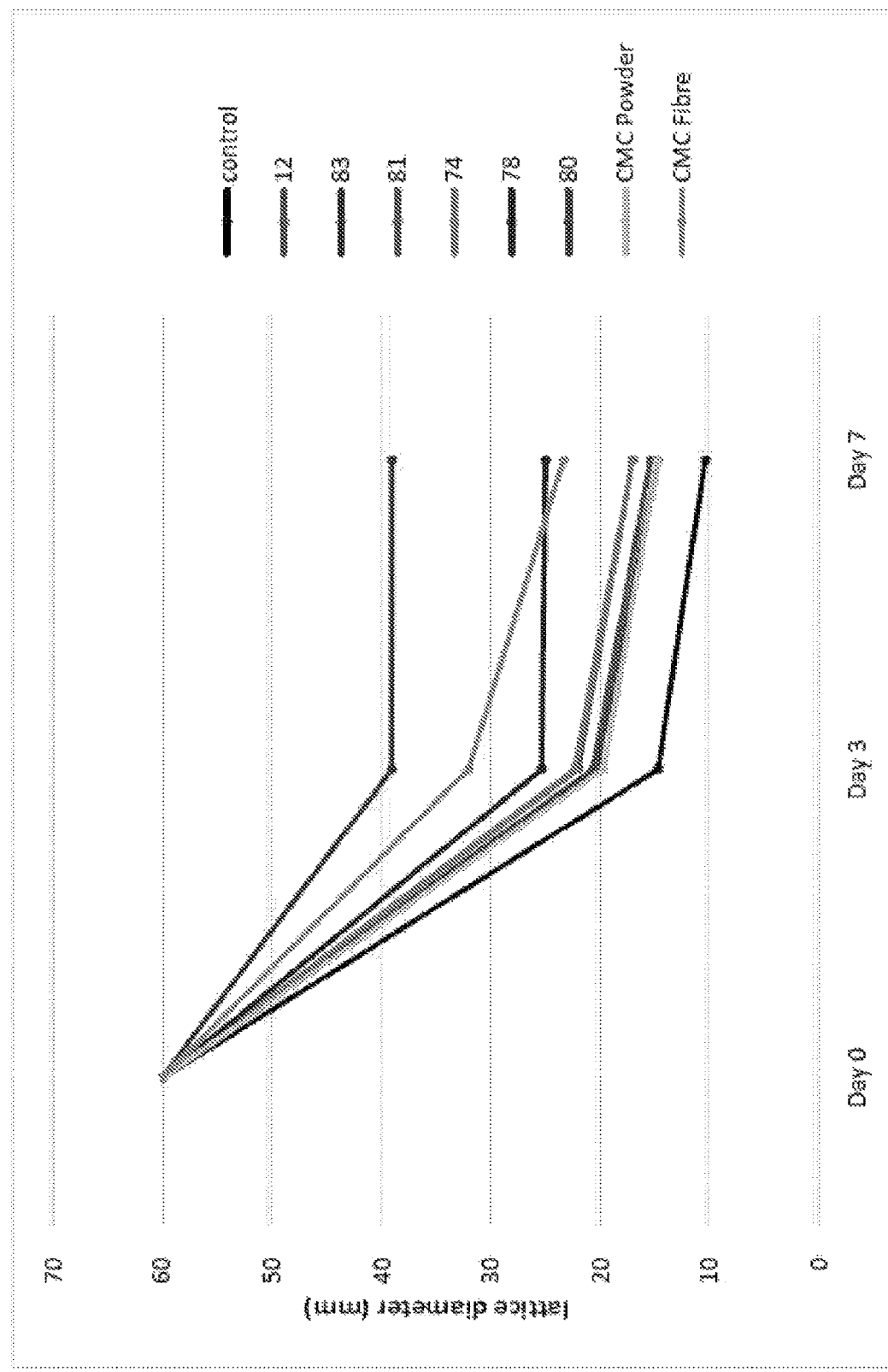
FIG. 8 shows results of studies with collagen matrix model, plot showing the lattice diameter over 7 days— Patient A.
Figure 9:
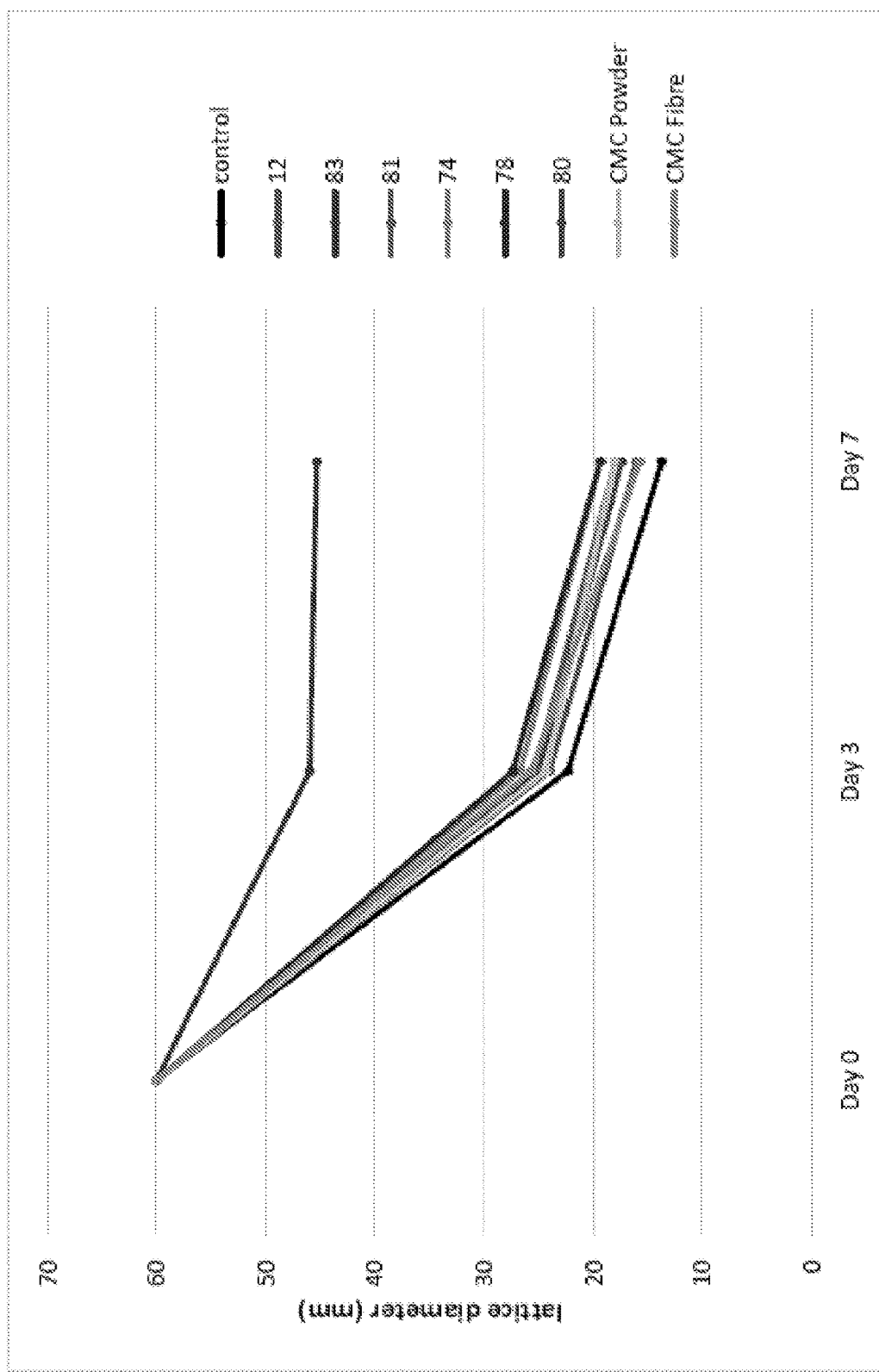
FIG. 9 shows results of studies with collagen matrix model, plot showing the lattice diameter over 7 days— Patient F.
Figure 10:
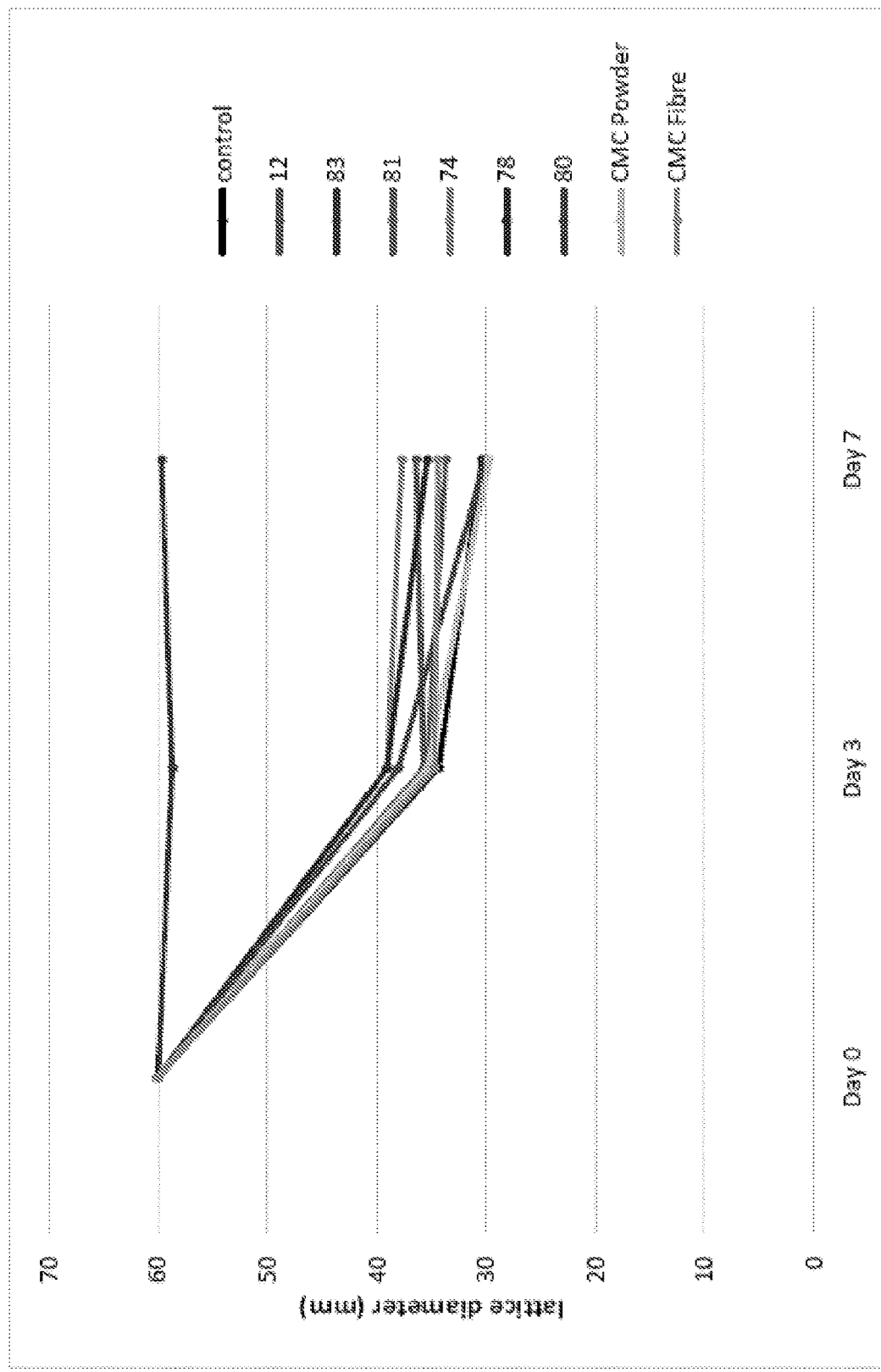
FIG. 10 shows results of studies with collagen matrix model, plot showing the lattice diameter over 7 days— Patient G.
Figure 11:
FIG. 11 shows results of studies with collagen matrix model, wherein photographs indicate the difference in lattice diameter at days 3 and 7— Patient A.
Figure 11:
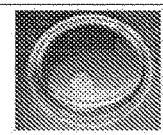
Figure 11:
Figure 11:
Figure 11:
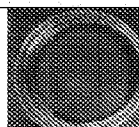
Figure 11:
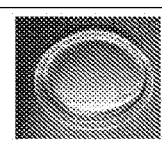
Figure 11:
Figure 11:
Figure 11:
Figure 11:
Figure 11:
Figure 11:
Figure 11:
Figure 11:
Figure 11:
Figure 11:
Figure 11:
Figure 11:
Figure 12:
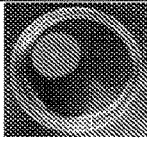
FIG. 12 shows results of studies with collagen matrix model, wherein photographs indicate the difference in lattice diameter at days 3 and 7— Patient F.
Figure 12:
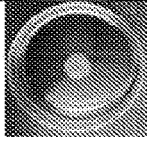
Figure 12:
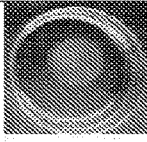
Figure 12:
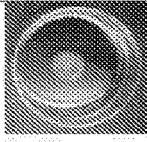
Figure 12:
Figure 12:
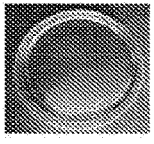
Figure 12:
Figure 12:
Figure 12:
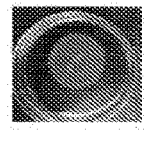
Figure 12:
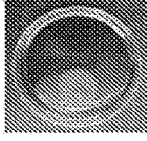
Figure 12:
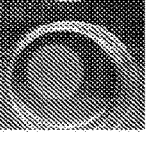
Figure 12:
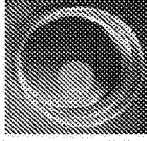
Figure 12:
Figure 12:
Figure 12:
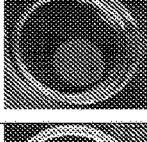
Figure 12:
Figure 12:
Figure 12:
Figure 13:
FIG. 13 shows results of studies with collagen matrix model, wherein photographs indicate the difference in lattice diameter at days 3 and 7— Patient G.
Figure 13:
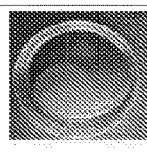
Figure 13:
Figure 13:
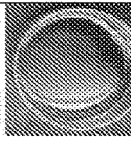
Figure 13:
Figure 13:
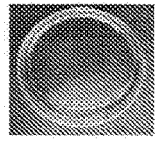
Figure 13:
Figure 13:
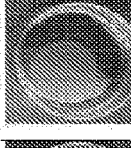
Figure 13:
Figure 13:
Figure 13:
Figure 13:
Figure 13:
Figure 13:
Figure 13:
Figure 13:
Figure 13:
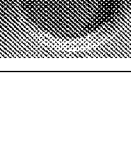
Figure 13:
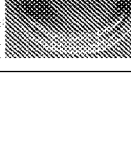

During the collagen matrix model studies, fibroblast cells remained viable across all samples. Compared to the control, only slightly less reorganization was observed for the modified CMC samples with the exception of 83, CMC-longer PEG-NH2 powder, which showed only limited fibroblast re-organization through the test compared to the other samples (FIG. 8, FIG. 9 and FIG. 10). A significant difference was observed between compound 83 (CMC-longer PEG-NH2 powder; lattice diameter of about 40 mm to 60 mm at day 7) and compound 12 (CMC-PEG-NH2 powder; lattice diameter of about 15 mm-35 mm at day 7), the results which are evident from FIGS. 8-10. The raw data, which is evident from the photographs in FIGS. 11-13, demonstrate the effect of each of compounds 12, 83, 81, 74, 78, 80, CMC powder and CMC fiber on the lattice diameter at days 3 and 7 in cell samples obtained from patients A (FIG. 11), B (FIG. 12), and C (FIG. 13), respectively.

Conclusion

The study demonstrates that modified CMC materials were not toxic to fibroblast cells. Also, there was no difference between the fiber and the powder formats, the longer or shorter PEG spacer linkers, or the addition of peptides and the detectable fragments. Fibroblasts survived in all cases during the collagen matrix model, reorganization was only slightly slower than the control for most of the samples, except for CMC-longer PEG-NH2 powder, 83, which exhibited an attenuated effect compared to other compounds.

Example 36 Liquid Crystal (LC) Studies

Liquid Crystal Experimental Set-up

A study was conducted during which CMC gel was placed over 5CB liquid crystal and the anchoring monitored over time using a polarizing microscope. In order to set up an LC study, a chamber needs to be created in order to enable the LC to be held within a set area and to allow visualization using a polarizing microscope. TEM grid confinement of 5CB was implemented in accordance with published studies (Nazarenko et al., *Physical Review E* 1999, 60, R3495-R3497; Brake et al., *Langmuir* 2003, 19, 6436-6442).

To create a 5CB-TEM grid experimental system, firstly the glass slide, used as a base is preferably free from impurities such as grease. Cleaning was performed using Piranha solution, a strong oxidizing agent which removes all organic matter from the glass. Due to the strong oxidizing nature of the piranha solution, appropriate safety precautions were taken to avoid contact with skin and also avoid explosion.

Concentrated sulphuric acid (~30 mL, 98% grade) was added to a vessel containing the glass to be cleaned, followed by slow addition of hydrogen peroxide (— 10 mL, 30%) and left at RT for 1 hour. The piranha solution was poured out and the glass washed thoroughly with water and alcohol. Finally the waste piranha solution was carefully neutralized. Next, the glass was coated with octadecyltrichlorosilane (OTS). OTS is a long chain self-assembling amphiphilic molecule that will coat the glass slide surface and make it hydrophobic. Thus, 5CB is aligned with homeotropic anchoring along the base of the chamber. TEM grids were placed onto the OTS coated glass to make the grid for the LC solutions to be held within. 5CB was added carefully to the TEM grids using a capillary tube to ensure that each grid is sufficiently filled, but not over-filled so as to create a dome of solution on top of the grid. On addition of 5CB to the TEM grid, 5CB alignment was checked using the crossed polarized lens of a light microscope. 5CB is homeotropic at this stage, which is due to the alignment of the LCs with the OTS coated glass slide.

Figure 14:
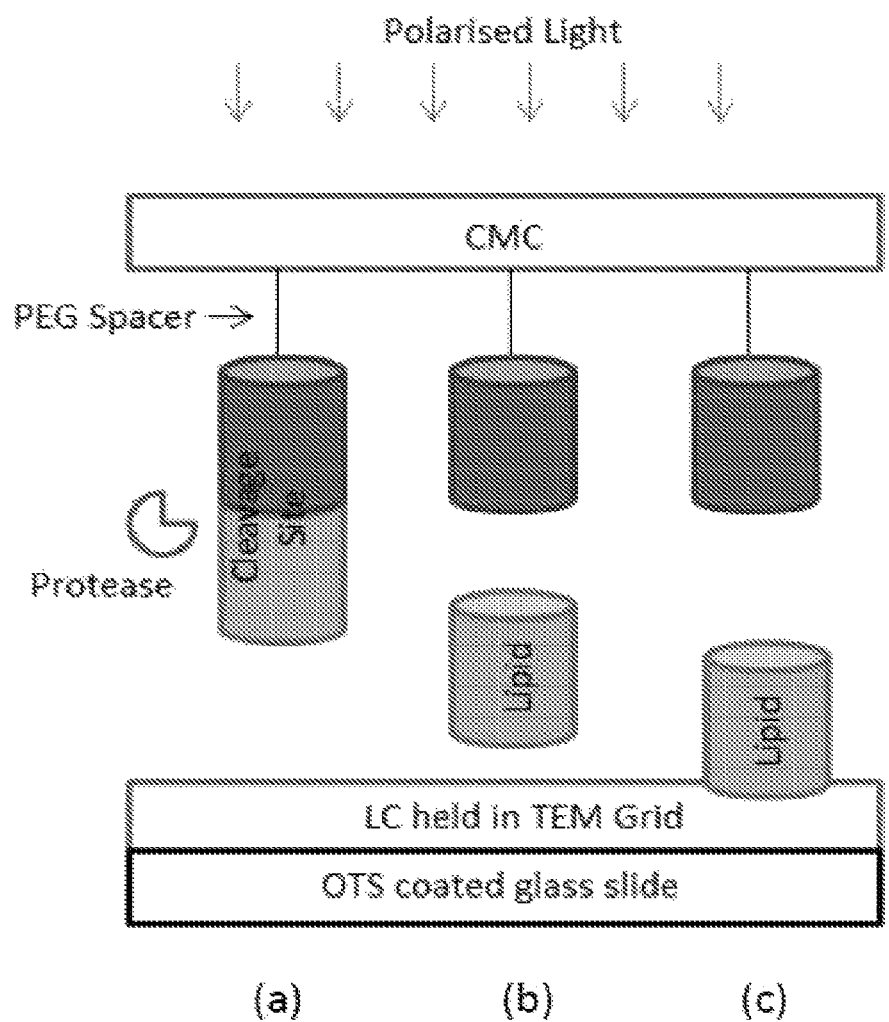
FIG. 14 shows a schematic diagram for a potential peptide modified CMC and LC system for detection of proteases, wherein (a) shows the initial system set up which would show homotropic LC alignment (dark if viewed under crossed polarized lenses), (b) shows the cleavage of the peptide releasing the lipid in progress, (c) shows the cleaved lipid in contact with LCs, which would initiate planar LC realignment (colored if viewed under crossed polarized lenses).
Figure 15A:
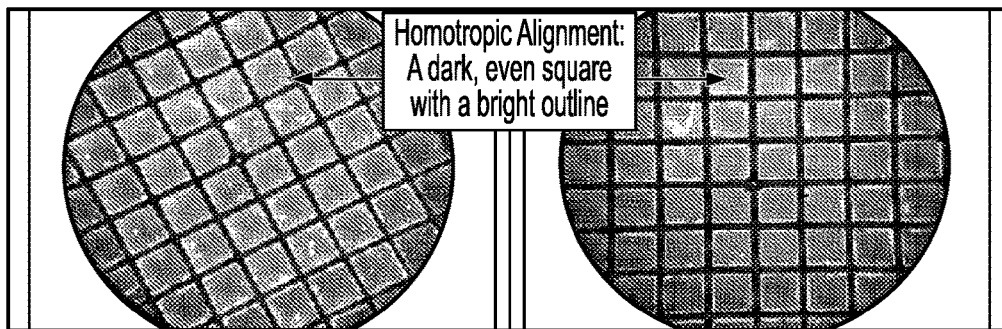
FIG. 15A shows micrographs of liquid crystal 4'-n-pentyl-4-cyano-biphenyl (5CB) filled TEM (Transmission Electron Microscopy) grids upon application of CMC gel and prior to application of CMC hydrogel-homeotropic LC alignment.
Figure 15B:
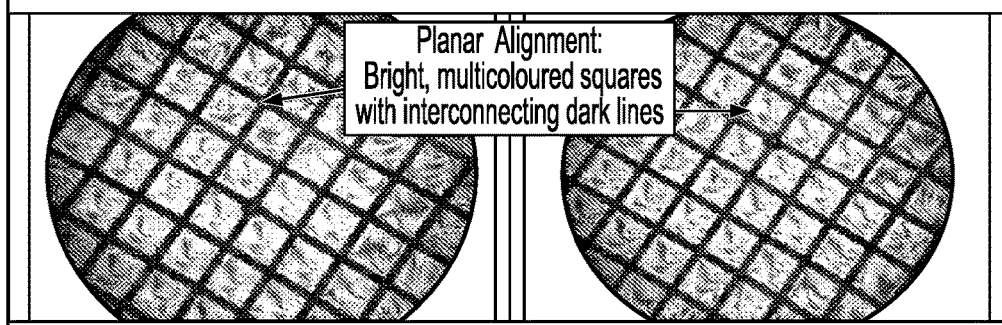
FIG. 15B shows the 5CB filled TEM grids after application of CMC hydrogel at T=0; change to planar LC alignment.
Figure 15C:
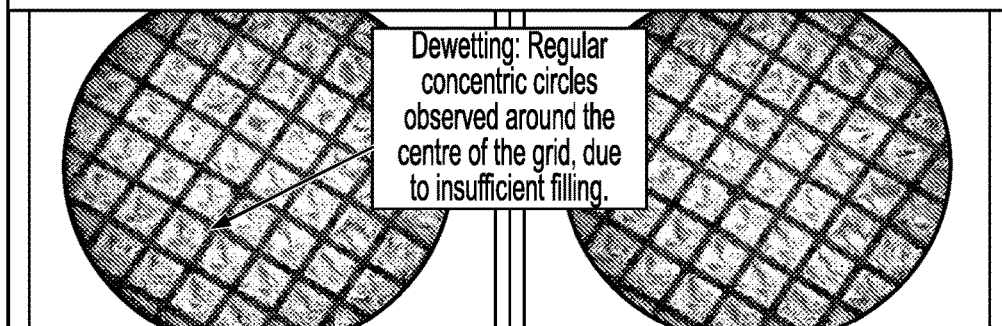
FIG. 15C shows the 5CB filled TEM grids after application of CMC hydrogel at T=2 minutes (planar LC alignment) (left panel) and after application of CMC hydrogel at T=5 minutes (planar LC alignment) (right panel).
Figure 15D:
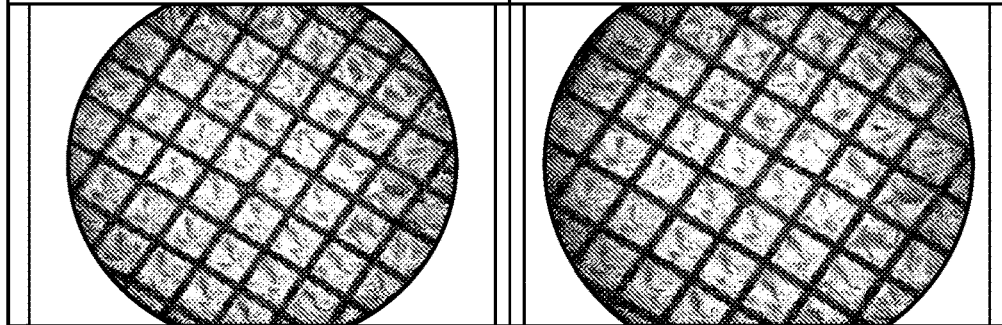
FIG. 15D shows the 5CB filled TEM grids after application of CMC hydrogel at T=10 minutes (planar LC alignment retained) (left panel) and after application of CMC hydrogen at T=90 minutes (planar LC alignment retained) (right panel).

The principle of enzyme detection relies upon the change of LC orientation, upon release of a lipid, for example DLPC. A potential system using peptide modified CMC and LCs in this way is shown in FIG. 14. To this end, FIG. 15 shows micrographs showing 5CB filled TEM grids upon application of CMC gel.

Other Embodiments

The preceding examples can be repeated by substituting the generically or specifically described reactants and/or operating conditions of the disclosed technology for those used in the preceding examples.

From the foregoing description, one skilled in the art can easily ascertain the essential characteristics of the disclosed technology and, without departing from the spirit and scope thereof, can make various changes and modifications to the disclosed technology to adapt it to various usages and conditions.

Unless otherwise defined, all technical and scientific terms used herein have the same meaning as commonly understood by one of ordinary skill in the art. Although methods and materials similar or equivalent to those described herein can be used in the practice or testing of the disclosed technology, suitable methods and materials are described in the foregoing paragraphs. In addition, the materials, methods, and examples are illustrative only and not intended to be limiting. In case of conflict, the present specification, including definitions, will control.

All United States patents and published or unpublished United States patent applications cited herein are incorporated by reference. All published foreign patents and patent applications cited herein are hereby incorporated by reference. All published references, documents, manuscripts, scientific literature cited herein are hereby incorporated by reference. All identifier and accession numbers pertaining to NCBI, GENBANK, EBI, PUBMED databases that are cited herein are hereby incorporated by reference.

While preferred embodiments of the disclosed technology have been shown and described herein, it will be obvious to those skilled in the art that such embodiments are provided by way of example only. Numerous variations, changes, and substitutions will now occur to those skilled in the art. It should be understood that various alternatives to the embodiments of the disclosed technology described herein may be employed in practicing the disclosed technology. It is intended that the following claims define the scope of the disclosed technology and that methods and structures within the scope of these claims and their equivalents be covered thereby.

What is claimed is:

1. A wound dressing material comprising:

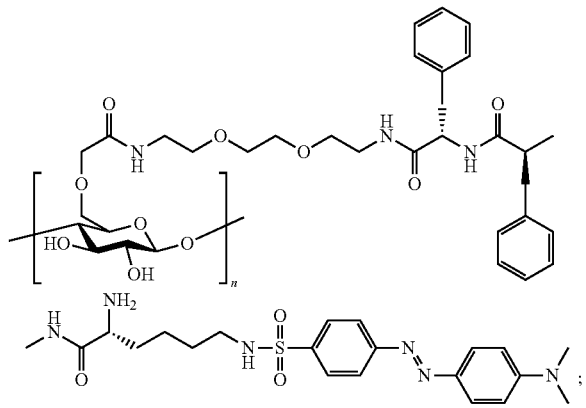

wherein n=200-4000.

* * * * *